United States Patent
Bigge et al.

(10) Patent No.: US 6,534,522 B2
(45) Date of Patent: Mar. 18, 2003

(54) SUBTYPE-SELECTIVE NMDA RECEPTOR LIGANDS AND THE USE THEREOF

(75) Inventors: Christopher F. Bigge, Ann Arbor, MI (US); Gian Luca Araldi, Washington, DC (US); Sui Xiong Cai, Foothill, CA (US); Anthony P. Guzikowski, Eugene, OR (US); Donald Lamunyon, Tualatin, OR (US); Nancy C. Lan, South Pasadena, CA (US); Zhang-Lin Zhou, Irvine, CA (US); John F. W. Keana, Eugene, OR (US)

(73) Assignees: Warner-Lambert Company, Morris Plains, NJ (US); Cocensys, Incorporated, Irvine, CA (US)

( * ) Notice: Subject to any disclaimer, the term of this patent is extended or adjusted under 35 U.S.C. 154(b) by 0 days.

(21) Appl. No.: 09/779,024

(22) Filed: Feb. 7, 2001

(65) Prior Publication Data

US 2001/0051633 A1 Dec. 13, 2001

Related U.S. Application Data

(62) Division of application No. 09/091,592, filed as application No. PCT/US96/20746 on Dec. 20, 1996, now Pat. No. 6,218,404.
(60) Provisional application No. 60/009,185, filed on Dec. 22, 1995.

(51) Int. Cl.[7] .................. C07D 401/12; A61K 31/47
(52) U.S. Cl. .................. 514/307; 546/139; 546/148
(58) Field of Search .............. 514/307; 546/139, 546/148

(56) References Cited

U.S. PATENT DOCUMENTS

| | | | |
|---|---|---|---|
| 3,255,196 A | 6/1966 | Debarre et al. | 260/212 |
| 3,311,624 A | 3/1967 | Ohnacker et al. | 260/212 |
| 3,632,767 A | 1/1972 | Gray et al. | 424/267 |
| 3,686,187 A | 8/1972 | Cole et al. | 260/212 |
| 4,567,186 A | 1/1986 | Lesher et al. | 514/300 |
| 4,567,187 A | 1/1986 | Banno et al. | 514/312 |
| 4,577,020 A | 3/1986 | Gall | 544/366 |
| 4,643,995 A | 2/1987 | Engel et al. | 514/210 |
| 4,902,695 A | 2/1990 | Ornstein | 514/307 |
| 4,942,169 A | 7/1990 | Sagimoto et al. | 514/318 |
| 5,011,834 A | 4/1991 | Weber et al. | 514/212 |
| 5,036,077 A | 7/1991 | Van Broeck et al. | 514/317 |
| 5,169,855 A | 12/1992 | Cain et al. | 514/319 |
| 5,192,751 A | 3/1993 | Thor | 514/82 |
| 5,192,799 A | 3/1993 | Tomino et al. | 514/469 |
| 5,202,346 A | 4/1993 | Butera et al. | 514/326 |
| 5,273,977 A | 12/1993 | Glase et al. | 514/277 |
| 5,352,683 A | 10/1994 | Mayer et al. | 514/289 |
| 5,466,698 A | 11/1995 | Glase et al. | 514/318 |
| 5,620,988 A | 4/1997 | Glase et al. | 514/307 |

FOREIGN PATENT DOCUMENTS

| | | |
|---|---|---|
| AU | 43438/85 | 6/1985 |
| BE | 860701 | 5/1978 |
| CA | 696999 | 11/1964 |
| DE | 2939292 | 4/1981 |
| DE | 3703435 | 8/1988 |
| DE | 4410822 | 9/1995 |
| EP | 149088 | 7/1985 |
| EP | 0235463 | 9/1987 |
| EP | 0308328 | 3/1989 |
| EP | 337136 | 10/1989 |
| EP | 0351282 | 1/1990 |
| EP | 0398578 | 11/1990 |
| EP | 0481853 | 4/1991 |
| EP | 0445701 | 9/1991 |
| EP | 0449186 | 10/1991 |
| EP | 488959 A | 6/1992 |
| EP | 0524846 | 1/1993 |
| EP | 572952 | 12/1993 |
| EP | 0648744 | 4/1995 |
| EP | 649838 | 4/1995 |
| FR | 2681319 | 3/1993 |
| GB | 1055548 | 1/1967 |
| GB | 2056435 | 3/1981 |
| JP | 61-115068 | 6/1986 |
| JP | 61-227565 | 10/1986 |
| JP | 04217945 | 8/1992 |
| JP | 04-312572 | 11/1992 |
| WO | WO 91/06297 | 5/1971 |
| WO | WO 88/02365 | 4/1988 |
| WO | WO 91/17156 | 11/1991 |
| WO | WO 92/02502 | 2/1992 |
| WO | WO 92/07831 | 10/1992 |
| WO | WO 92/18127 | 10/1992 |
| WO | WO 93/00313 | 1/1993 |
| WO | WO 93/15052 | 2/1993 |
| WO | WO 93/11107 | 6/1993 |
| WO | WO 93/02052 | 8/1993 |
| WO | WO 94/10166 | 5/1994 |
| WO | WO 94/13275 | 6/1994 |
| WO | WO 94/18172 | 8/1994 |

OTHER PUBLICATIONS

Stütz, A. et al., *Tetrahedron*, vol. 41 (23) pp. 5685–5696 (1985).

(List continued on next page.)

*Primary Examiner*—Zinna Northington Davis
(74) *Attorney, Agent, or Firm*—Fitzpatrick, Cella, Harper & Scinto

(57) ABSTRACT

The invention relates to subtype-selective NMDA receptor ligands and the use thereof for treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the overstimulation of the excitatory amino acids, treating anxiety, psychosis, convulsions, aminoglycoside antibiotics-induced hearing loss, migraine headache, chronic pain, Parkinson's disease, glaucoma, CMV retinitis, urinary incontinence, opioid tolerance or withdrawal, and inducing anesthesia, as well as for enhancing cognition.

8 Claims, No Drawings

OTHER PUBLICATIONS

Williams, C.H. et al., *Biochemical Pharmacology*, vol. 23, pp. 629–636 (1974).
Starshinova, L.A. et al., *Khim.–Farm. Zh.*, vol. 23 (10), pp. 1206–1209 (1989).
Praliev, K.D. et al., *Khim.–Farm. Zh.*, vol. 18(10), pp. 1203–1208 (1984).
M. Lauritzen, Acta. Neurol. Scand. 76 (Suppl. 113), 4–40 (1987).
De Lean et al., Am. J. Physiol. 235, E97–102 (1978).
W.U. Schmidt, et al., Amino Acids 1, 225–237 (1991).
T. Klockgether, L. Truski, Ann. Neurol. 34, 585–593 (1993).
Annu. Rev. Neurosci 17, 31–108 (1994).
R.W. Gifford, et al., Arch. Intern. Med. 153, 154–183, (1993).
Harper and Powers, Biochemistry 24, 7200–7213 (1985).
Sugihara et al., Biochem. Biophys Res. Commun. 185, 826–832 (1992).
C.F. Bigge, Biochem. Pharmacol. 45, 1547–1561 (1993).
M. Lauritzen et al., Brian Res. 475, 317–327 (1988).
J.E. Haley, et al., Brain Res. 518, 218–226 (1990).
Shaw et al., Brain Research 539, 164–168 (1991).
Marek et al., Brain Res. 547, 77–81 (1991).
Lufty et al., Brain Res. 616, 83–88 (1993).
P.H. Hutson, et al., Br. J. Pharmacol. 103, 2037–2044 (1991).
L.J. Bristow, et al., Br. J. Pharmacol. 108, 1156–1163 (1993).
Chemical Abstract, vol. 94, No. 15, 94:121260j (1984).
Chemical Abstracts, vol. 115, No. 23, 115:247459b (1991).
D. Lonsdale, Dev. Pharmacol. Ther. 4, 28–36 (1982).
B.V. Clineschmidt et al., Drug Dev. Res. 2, 147–163 (1982).
Rojas et al. Drug Dev. Res. 29, 222–226 (1993).
J.H. Kehne et al., Eur. J. Pharmacol. 193, 283–292 (1991).
J. Winslow et al., Eur. J. Pharmacol. 190, 11–21 (1990).
R. Dunn et al., Eur. J. Pharmacol. 214, 207–214 (1992).
E.W. Anthony, Eur. J. Pharmacol. 250, 317–324 (1993).
Ikeda et al., FEBS Lett. 313, 34–38 (1992).
D.L. Comins et al., J. Am. Chem. Soc. 116, 4719–4728 (1994).
DeGroat et al., J. Auton. Nerv. Sys. 3, 135–160 (1981).
Ishii et al., J. Biol. Chem. 268, 2836–2843 (1993).
Decker et al., J. Immunol. Methods 15, 61–69 (1988).
Harbert et al., J. Med. Chem. 23, 635–643 (1980).
Abou–Gharbia et al., J. Med. Chem. 30, 1818–1823 (1987).
N. Iwasaki et al., J. Med. Chem. 38, 496–507 (1995).
Kerrigan et al., J. Med. Chem. 38, 544–552 (1995).
Cook et al., J. Med. Chem. 38, 753–763 (1995).
J.N. Dumont, J. Morphol. 136, 153–179 (1972).
P.T. Francis, N.R. Sims, A.W. Procter, D.M. Bowen, J. Neurochem. 60(5), 1589–1604 (1993).
W. Danysz et al., J. Neuroal Trans. 7, 155–166, (1994).
A.A.P.J. Leaó, Neurophysiol. 7, 359–390 (1994).
D.W. Choi et al., J. Neuroscience 7, 357–368 (1987).
S.R. Skilling et al, J. Neuro Sci. 10, 1309–1318 (1990).
D.L. Comins et al., J. Org. Chem. 55, 2574–2576 (1990).
Way et al., J. Pharmacol. Exp. Ther. 167, 1–8 (1969).
Huidobro et al., J. Pharmacol. Exp. Ther. 198, 318–329 (1976).
L.D. Snell et al., J. Pharmacol. Exp. Ther. 235, 50–57 (1985).
Lutfy et al., J. Pharmacol. Exp. Ther. 256, 575–580 (1991).
Tiseo et al., J. Pharmacol. Exp. Ther. 264, 1090–1096 (1993).
Miledi and Parker, J. Physiol. 357, 173–183 (1984).
Miledi and Woodward, J. Physiol. 416, 601–621 (1989).
Landon and Robbins, Methods in Enzymology 124, 412–425 (1986).
Woodward et al., Mol. Pharmacol. 41, 89–103 (1992).
Curtis, et al., Nature 191, 1010–1011 (1961).
Moriyoshi, et al. Nature 354, 31–37 (1991).
Kutsuwada et al., Nature 358, 36–41 (1992).
Basile, et al., Nature Medicine, 2, 1338–1343, (1996).
Herman et al., Neuropsychopharmacology 13, 269–293 (1995).
Dickenson and Aydar, Neuroscience Lett. 121, 263–266 (1991).
Vera and Nadelhaft, Neuroscience Lett. 134, 135–138 (1991).
S.A. Lipton, P.A. Rosenberg, New Eng. J. Med. 330 (9), 613–622 (1994).
Org. Reactions 6, 151–206 (1951).
Dubuisson and Dennis, Pain 4, 161–174 (1977).
M. Fieser, L.F. Fieser, Reagents for Organic Synthesis 6, 183 (1977).
Kornetsky et al., Science 162, 1011–1012 (1968).
Sansalla et al., Science 243, 398–400 (1989).
Trujillo et al., Science 251, 85–87 (1991).
Monyer et al., Science 256, 1217–1221 (1992).
R.A. Sharma, W. Korytnyk, Tetrahedron Lett. 573–576 (1977).
D.L. Comins, et al., Tetrahedron Lett. 29, 773–776 (1988).
D.L. Comins, et al., Tetrahedron Lett. 32, 5697–5700 (1991).
S. Lipton, TINS 16(12), 527–532 (1993).
Carlsson et al., Trends Neurosci. 13, 272–276 (1990).
Tepley et al., *Biomagnetism*, eds. S. Williamson, L. Kaufmann, pp. 327–330, Plenum Press, New York (1990).
S.A. Glase et al., J. Med. Chem. 39, 3179–3187 (1996).
B.L. Chenard et al., J. Med. Chem. 34, 3085–3090 (1991).

SUBTYPE-SELECTIVE NMDA RECEPTOR LIGANDS AND THE USE THEREOF

This application is a divisional application of U.S. Pat. No. 09/091,592, filed Sep. 16, 1998, now U.S. Pat. No. 6,218,404, which is a national stage of PCT/US96/20746, filed on Dec. 20, 1996, which claimed the benefit of U.S. Provisional Appln. No. 60/009,185, filed on Dec. 22, 1995.

BACKGROUND OF THE INVENTION

1. Field of the Invention

This invention is related to 2-substituted piperidine analogs. The analogs are selectively active as antagonists of N-methyl-D-aspartate (NMDA) receptor subtypes. The invention is also directed to the use of 2-substituted piperidine analogs as neuroprotective agents for treating conditions such as stroke, cerebral ischemia, central nervous system trauma, hypoglycemia, anxiety, convulsions, aminoglycoside antibiotics-induced hearing loss, migraine headaches, chronic pain, glaucoma, CMV retinitis, psychosis, urinary incontinence, opioid tolerance or withdrawal, or neurodegenerative disorders such as lathyrism, Alzheimer's Disease, Parkinsonism and Huntington's Disease.

2. Related Background Art

Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-Aspartate (NMDA) receptor. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasms, hypoglycemia, cardiac arrest, status epilepticus, perinatal asphyxia, anoxia such as from drowning, pulmonary surgery and cerebral trauma, as well as lathyrism, Alzheimer's Disease, Parkinson's Disease and Huntington's Disease.

Excitatory amino acid receptor antagonists that block NMDA receptors are recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain and anxiety, and may be a significant causal factor in chronic neurodegenerative disorders such as Parkinson's disease [T. Klockgether, L. Turski, Ann. Neurol. 34, 585–593 (1993)], human immunodeficiency virus (HIV) related neuronal injury, amyotrophic lateral sclerosis (ALS), Alzheimer's disease [P.T. Francis, N. R. Sims, A. W. Procter, D. M. Bowen, J. Neurochem. 60 (5), 1589–1604 (1993)] and Huntington's disease. [See S. Lipton, TINS 16 (12), 527–532 (1993); S. A. Lipton, P. A. Rosenberg, New Eng. J. Med. 330 (9), 613–622 (1994); and C. F. Bigge, Biochem. Pharmacol. 45, 1547–1561 (1993) and references cited therein.]. NMDA receptor antagonists may also be used to prevent tolerance to opiate analgesia or to help control withdrawal symptoms from addictive drugs (Eur. Pat. Appl. 488,959A).

U.S. Pat. No. 5,352,683, discloses the treatment of chronic pain with a compound with is an antagonist of the NMDA receptor.

U.S. Pat. No. 4,902,695, discloses certain competitive NMDA antagonists that are useful for the treatment of neurological disorders, including epilepsy, stroke, anxiety, cerebral ischemia, muscular spasms, and neurodegenerative diseases such as Alzheimer's disease and Huntington's disease.

U.S. Pat. No. 5,192,751 discloses a method of treating urinary incontinence in a mammal which comprises administering an effective amount of a competitive NMDA antagonist.

Evidence indicates that the NMDA receptor comprises a class of such receptors with different subunits. Molecular cloning has revealed the existence of at least five subunits of the NMDA receptors designated NR1 & NR2A through 2D. It has been demonstrated that the co-expression of NR1 with one of the NR2 subunits forms a receptor with a functional ion channel. (*Ann. Rev. Neurosci.* 17:31–108(1994)). It is thought that NMDA receptors with different subunit composition generate the different NMDA receptor subtypes found in the mammalian brain.

An object of this invention is to provide novel—subtype-selective NMDA receptor ligands.

SUMMARY OF THE INVENTION

The invention relates to a subtype-selective NMDA receptor ligand having the Formula (I):

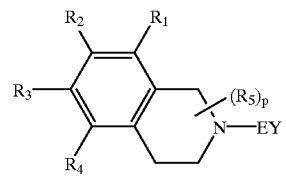

wherein $R_1$–$R_4$ are independently hydrogen, halo, haloalkyl, aryl, fused aryl, a heterocyclic group, a heteroaryl group, alkyl, alkenyl, alkynyl, arylalkyl, arylalkenyl, arylalkynyl, hydroxyalkyl, nitro, amino, cyano, cyanamido, $N(CN)_2$, guanidino, amidino, acylamido, hydroxy, thiol, acyloxy, azido, alkoxy, carboxy, carbonylamido, or alkylthiol;

E is $(CR_aR_b)_r$—$G_s$—$(CR_cR_d)_t$, wherein $R_a$, $R_b$, $R_c$ and $R_d$ are independently selected from the group consisting of hydrogen, alkyl, aryl, hydroxy or carboxy; G is oxygen, sulfur, sulfone, sulfoxide, carboxy ($CO_2$ or $O_2C$), carbonyl (CO), or $NR_e$, wherein $R_e$ is hydrogen, alkyl or aryl; r and t are independently 0, 1, 2, 3, 4, or 5; and s is 0 or 1;

$R_5$ is hydrogen, hydroxy, alkylcarboxy, optionally substituted aryl, optionally substituted aralkyl, optionally substituted aryloxyalkyl, optionally substituted benzyloxyalkyl, a heterocyclic group, a heterocyclic substituted alkyl group, heteroaryl, or a heteroaryl substituted alkyl group;

p is 0, 1, 2, or 3;

Y is hydrogen, hydroxy, $CH_3$, CN, $CO_2R$, sulfate, optionally substituted aryl, optionally substituted aryloxy, optionally substituted arylthioxy, optionally substituted aroyl, =—$Y_1$, =—$Y_1$ (which may be cis or trans, throughout) carbonylamido, hydrazino, oximo, amidino, optionally substituted heterocyclic group, optionally substituted heterocycloxy, optionally substituted heteroaryl, optionally substituted heteroaryloxy, optionally substituted cycloalkyl group, optionally substituted cycloalkoxy group, amino, amido, ureido, or guanidino; and $Y_1$ is hydrogen, alkyl, hydroxyalkyl, optionally substituted aralkyl, an optionally substituted aryl, optionally substituted cycloalkyl, aminoalkyl, amidoalkyl, ureidoalkyl, or guanidinoalkyl.

The invention also relates to a subtype-selective NMDA receptor ligand having the Formula (II):

wherein
$R_1$–$R_4$, E, Y and $Y_1$ are the same as described in formula I;
$R_5$ is hydrogen, lower alkyl, acyl or aryl;
p is 0, 1, 2 or 3; and
$R_6$ is hydrogen, hydroxy, alkylcarboxy, optionally substituted aryl, optionally substituted aralkyl, optionally substituted aryloxyalkyl, optionally substituted benzyloxyalkyl, a heterocyclic group, a heterocyclic substituted alkyl group, heteroaryl, or a heteroaryl substituted alkyl group; and The invention also relates to a subtype-selective NMDA receptor ligand having the Formula (IIa):

wherein
$R_1$–$R_4$, E, Y and $Y_1$ are the same as described in formula I;
$R_5$ is hydrogen, lower alkyl, acyl or aryl;
p is 0, 1, 2 or 3; and
$R_5$ is hydrogen, hydroxy, alkylcarboxy, optionally substituted aryl, optionally substituted aralkyl, optionally substituted aryloxyalkyl, optionally substituted benzyloxyalkyl, a heterocyclic group, a heterocyclic substituted alkyl group, heteroaryl, or a heteroaryl substituted alkyl group.

The invention also relates to a subtype-selective NMDA receptor ligand having the Formula (III):

wherein
W is an adamantyl group, an optionally substituted aryl group, or an optionally substituted heteroaryl group;
X is a bond, $(CH_2)_m$ carbonyl, oxygen, or NR;

E is the same as described in formula I;
Y is hydrogen, hydroxy, $CH_3$, CN, $CO_2R$; an aminoalkyl group, an amidoalkyl group, a ureidoalkyl group, or a guanidinoalkyl group;
R is hydrogen, alkyl, aminoalkyl, amidoalkyl, ureidoalkyl, or guanidinoalkyl;
$R_1$ is hydrogen, hydroxy, alkylcarboxy, optionally substituted aryl, optionally substituted aralkyl, optionally substituted aryloxyalkyl, optionally substituted benzyloxyalkyl, a heterocyclic group, a heterocyclic substituted alkyl group, heteroaryl, or a heteroaryl substituted alkyl group;
m is 0, 1, 2, or 3; and
p is 0, 1, 2, 3 or 4.
with the proviso, that when W is adamantyl or when p is greater than zero, or when the piperidine is substituted in the 3-position by W-X, then Y may also be optionally substituted aryl, optionally substituted aryloxy, optionally substituted arylthioxy, optionally substituted aroyl, $\equiv$—$Y_1$, $=$—$Y_1$, optionally substituted heterocyclic group, optionally substituted heterocycloxy, optionally substituted heteroaryl, optionally substituted heteroaryloxy, optionally substituted cycloalkyl group, optionally substituted cycloalkoxy group, amino, amido, ureido, or guanidino;
wherein
$Y_1$ is hydrogen, alkyl, hydroxyalkyl, optionally substituted aralkyl, optionally substituted aryl, optionally substituted cycloalkyl, aminoalkyl, amidoalkyl, ureidoalkyl, or guanidinoalkyl.

The invention also relates to a subtype-selective NMDA receptor ligand having the Formula (IV):

wherein
$R_1$–$R_5$ are independently hydrogen, halo, haloalkyl, aryl, fused aryl, a heterocyclic group, a heteroaryl group, alkyl, alkenyl, alkynyl, arylalkyl, arylalkenyl, arylalkynyl, hydroxyalkyl, nitro, amino, cyano, acylamido, hydroxy, thiol, acyloxy, azido, alkoxy, carboxy, carbonylamido, or alkylthiol; and
E, Y and $Y^1$ are the same as described in formula I.

The invention also relates to a subtype-selective NMDA receptor ligand having the Formula (V):

wherein
$R_1$–$R_4$, E, Y and $Y_1$ are the same as described in formula I.

The invention also relates to a subtype-selective NMDA receptor ligand having the Formula (VI):

wherein
- W is an adamantyl group, an optionally substituted aryl group, or an optionally substituted heteroaryl group;
- X is a bond, $(CH_2)_m$, oxygen, or NR;
- E, Y and $Y_1$ are the same as described in formula I;
- R is alkyl, hydroxy, an aminoalkyl group, an amidoalkyl group, a ureidoalkyl group, or a guanidinoalkyl group;
- $R_1$ is hydrogen, hydroxy, alkylcarboxy, optionally substituted aryl, optionally substituted aralkyl, optionally substituted aryloxyalkyl, optionally substituted benzyloxyalkyl, a heterocyclic group, a heterocyclic substituted alkyl group, heteroaryl, or a heteroaryl substituted alkyl group;
- m is 0, 1, 2, or 3; and
- q is 0, 1 or 2.

The invention also relates to a subtype-selective NMDA receptor ligand having the Formula (VII):

wherein
- W is an adamantyl group, an optionally substituted aryl group, or an optionally substituted heteroaryl group;
- X is a bond, $(CH_2)_m$ oxygen, or NR;
- E, Y and $Y_1$ are the same as described in formula I;
- R is alkyl, hydroxy, an aminoalkyl group, an amidoalkyl group, a ureidoalkyl group, or a guanidinoalkyl group;
- $R_1$ is hydrogen, hydroxy, alkylcarboxy, optionally substituted aryl, optionally substituted aralkyl, optionally substituted aryloxyalkyl, optionally substituted benzyloxyalkyl, a heterocyclic group, a heterocyclic substituted alkyl group, heteroaryl, or a heteroaryl substituted alkyl group;
- m is 0, 1, 2, or 3; and
- p is 0, 1 or 2.

The invention also relates to a subtype-selective NMDA receptor ligand having the Formula (VIII):

wherein
- W is an adamantyl group, an optionally substituted aryl group, or an optionally substituted heteroaryl group;
- X is a bond, $(CH_2)_m$, oxygen, or NR;
- E, Y and $Y_1$ are the same as described in formula I; R is alkyl, hydroxy, an aminoalkyl group, an amidoalkyl group, a ureidoalkyl group, or a guanidinoalkyl group;
- $R_1$ is hydrogen, hydroxy, alkylcarboxy, optionally substituted aryl, optionally substituted aralkyl, optionally substituted aryloxyalkyl, optionally substituted benzyloxyalkyl, a heterocyclic group, a heterocyclic substituted alkyl group, heteroaryl, or a heteroaryl substituted alkyl group;
- m is 0, 1, 2, or 3; and
- p is 0, 1 or 2.

The invention also relates to a subtype-selective NMDA receptor ligand having the Formula (IX):

wherein one of K and L is nitrogen and the other is CH; and

E, Y and $Y_1$ are the same as described in Formula I.

The invention also relates to a subtype-selective NMDA receptor ligand having the Formula (X):

wherein

E, Y and $Y_1$ are the same as described in formula I.

The invention also relates to a subtype-selective NMDA receptor ligand having the Formula (XI):

wherein

E, Y and $Y_1$ are the same as described in formula 1.

The invention also relates to a subtype-selective NMDA receptor ligand having the Formula (XII):

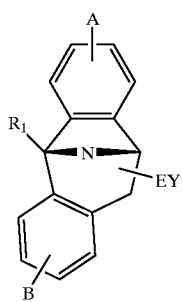

wherein
- A and B are one or more substituents which are independently hydrogen, halo, alkoxy, trifluoromethylthio, cyano, carboxy or hydroxy;
- $R_1$ is alkyl, alkenyl, aralkyl, cycloalkyl-alkyl, dialkylaminoalkyl, or hydroxyalkyl; and
- E, Y and $Y_1$ are the same as described in formula I.

The invention also relates to a subtype-selective NMDA receptor ligand having the Formula (XIII):

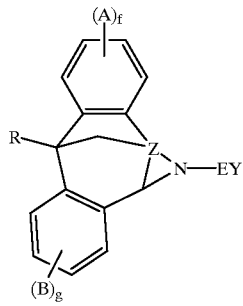

wherein
- R is hydrogen, $C_2$–$C_6$ acyl, $C_1$–$C_6$ alkyl, aryl, $C_1$–$C_6$ alkoxycarbonyl, $C_7$–$C_{10}$ aralkyl, $C_2$–$C_6$ alkenyl, $C_3$–$C_{15}$ dialkylaminoalkyl, $C_1$–$C_6$ hydroxyalkyl, $C_2$–$C_6$ alkynyl, $C_3$–$C_{15}$ trialkylsilyl, $C_4$–$C_{10}$ alkylcycloalkyl, or $C_3$–$C_6$ cycloalkyl;
- A and B are independently selected from the group consisting of a halogen such as chloro, fluoro, bromo, iodo, trifluoromethyl, azido, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, $C_5$–$C_6$ heterocycloalkyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro and $C_2$–$C_{15}$ dialkylsulfamoyl;
- Z represents a group selected from

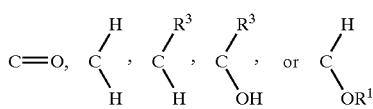

wherein $R^1$ is hydrogen, $C_1$–$C_6$ alkyl, $C_2$–$C_6$ alkenyl, aralkyl, $C_4$–$C_{15}$ dialkylaminoalkyl, heterocycloalkyl, $C_2$–$C_6$ acyl, aroyl, or aralkanoyl, and $R^3$ is $C_1$–$C_6$ alkyl, $C_2$–$C_6$ alkenyl, phenyl, aralkyl or $C_3$–$C_{15}$ dialkylaminoalkyl; and
- f and g are independently integers selected from 0 (X or Y is hydrogen, respectively), 1, 2, 3, or 4; and
- E, Y and $Y_1$ are the same as described in formual I.

The invention also relates to a subtype-selective NMDA receptor ligand having the Formula (XIV):

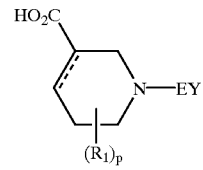

wherein
- $R_1$ is carboxy or an alkylester or amide thereof; alkyl carboxy or an alkyl ester or amide thereof; hydroxy or hydroxymethyl group;
- p is 0, 1 or 2;
- the dotted line represents a single or double bond;
- E, Y and $Y_1$ are the same as described in formula I.

The invention relates to a subtype-selective NMDA receptor ligand having the Formula (XV):

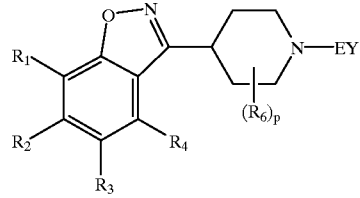

wherein
- $R_1$–$R_4$, E, Y and $Y_1$ are the same as described in formula I;
- $R_6$ is hydrogen, hydroxy, alkylcarboxy, optionally substituted aryl, optionally substituted aralkyl, optionally substituted aryloxyalkyl, optionally substituted benzyloxyalkyl, a heterocyclic group, a heterocyclic substituted alkyl group, heteroaryl, or a heteroaryl substituted alkyl group; and
- p is 0, 1, 2, or 3.

The invention relates to a subtype-selective NMDA receptor ligand having the Formula (XVI):

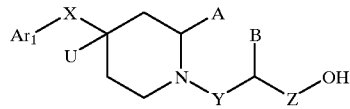

wherein $Ar_1$ is optionally substituted aryl or optionally substituted heteroaryl;
- X is O, $NR_1$ or $(CH_2)_n$ wherein n is 0, 1, 2, 3 or 4 and $R_1$ is hydrogen or a lower alkyl group having 1 to 6 carbon atoms;
- U is hydroxy or hydrogen;
- Y is $(CH_2)_m$ wherein m is 1, 2 or 3;
- Z is $(CHR_2)_z$ wherein z is 0, 1, 2, 3 or 4 and $R_2$ is hydroxy, hydrogen or a lower alkyl group having 1 to 6 carbon atoms; and
- A and B are each hydrogen or together are $(CH_2)_w$ wherein w is 0, 1, 2, 3 or 4.

Preferred substituents of $Ar_1$ include, for example, hydrogen, alkyl, a halogenated alkyl group such as a trifluoromethyl group, halogen, nitro, aryl, aralkyl, amino, a lower alkyl amino group or a lower alkoxy group.

The invention relates to a subtype-selective NMDA receptor ligand having the Formula (XVII):

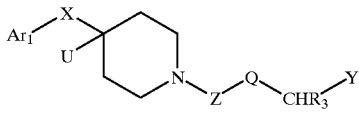

wherein $Ar_1$ is optionally substituted aryl or optionally substituted heteroaryl;

X is O, $NR_1$ or $(CH_2)_n$ wherein n is 0, 1, 2, 3 or 4 and $R_1$ is hydrogen or a lower alkyl group having 1 to 6 carbon atoms;

U is hydroxy or hydrogen;

Z is $(CHR_2)_z$ wherein z is 0, 1, 2, 3 or 4 and $R_2$ is hydroxy, hydrogen or a lower alkyl group having 1 to 6 carbon atoms;

Q is —CH=CH— or —C≡C—;

$R_3$ is hydrogen, hydroxy or hydroxy substituted lower alkyl having 1 to 6 carbon atoms; and Y is hydrogen, hydroxy, optionally substituted aryl or optionally substituted heteroaryl.

Preferred substituents of the aryl and heteroaryl groups include, for example, hydrogen, alkyl, a halogenated alkyl group such as a trifluoromethyl group, halogen, nitro, aryl, aralkyl, amino, a lower alkyl amino group or a lower alkoxy group.

The invention also relates to the quaternary ammonium salts of any one of the compounds above obtained by reacting the compound with a lower alkyl halide, preferable, methyl iodide or methyl sulfate.

The invention also relates to a method of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease, Parkinson's disease and Down's syndrome, treating or preventing the adverse consequences of the overstimulation of the excitatory amino acids, treating anxiety, psychosis, convulsions, chronic pain, glaucoma, CMV retinitis, urinary incontinence, and inducing anesthesia, as well as enhancing cognition, and preventing opiate tolerance and withdrawal symptoms, comprising administering to an animal in need of such treatment an effective amount of any one of the subtype-selective NMDA receptor ligands of the present invention, or a pharmaceutically acceptable salt thereof.

DETAILED DESCRIPTION OF THE INVENTION

The present invention relates to the discovery of new compounds which are subtype-selective ligands of the NMDA receptor. There are a number of subtypes of the NMDA receptor including NR1A/2A, NR1A/2B, NR1A/2C and NR1A/2D. The discovery of ligands which are selective for one or more of these subtypes allows for the treatment of various conditions mediated through binding to the NMDA receptor, while minimizing unwanted side effects.

Electrophysiological assays may be utilized to characterize the actions of potential subtype-selective ligands at NMDA receptors expressed in *Xenopus oocytes*. The ligand may be assayed at the different subunit combinations of cloned rat NMDA receptors corresponding to the four putative NMDA receptor subtypes (Moriyoshi et al., *Nature* (Lond.) 354:31–37 (1991); Monyer et al., *Science* (Washington, D.C.) 256:1217–1221 (1992); Kutsuwada et al., *Nature* (Lond.) 358:36–41 (1992); Sugihara et al., *Biochem. Biophys. Res. Comm.* 185:826–832 (1992)).

Using fixed saturating concentrations of agonists (glutamate 100 $\mu$M, glycine 1–10 $\mu$M depending on subunit combination), the inhibitory potency of a putative subtype-selective ligand may be assayed at the NMDA receptors assembled from NR1A/2A, NR1A/2B, NR1A/2C and NR1A/2D subunit combinations.

Preferably, the subtype selective NMDA receptor ligands are limited efficacy NMDA receptor antagonists. Such limited efficacy antagonists are attractive because such drugs have built-in safety margins; no matter how high the dosage only a certain fraction of the response can be blocked. This could be particularly important for analgesic, anticonvulsant, anti-psychotic, antimigraine headache, anti-parkinson's disease and antiglaucoma indications, where overdosage of full antagonists may result in sedation. It is also likely that limited efficacy NMDA receptor antagonists, particularly those showing subtype-selectivity, will not induce such profound memory deficits as full antagonists.

Certain of the subtype-selective NMDA receptor ligands are expected to be able to mediate either inhibition or potentiation of membrane current response. Which type of effect predominates appears to be dependent upon the subunit composition of the receptors and on the structure of the molecule. The 1A/2A and 1A/2B subtypes are mainly in the forebrain. The 1A/2C and 1A/2D are mainly in the cerebellum. In addition to the potential of developing subtype-selective drugs for the treatment of diseases associated with the overstimulation of the NMDA receptor with few side effects, it is also possible to develop drugs that selectively potentiate particular subtypes of NMDA receptors present in particular parts of the brain. Such drugs could show therapeutic potential as cognitive-enhancers in treatments of neurodegenerative conditions such as Alzheimer's disease. In addition, there is a potential for developing drugs that selectively potentiate some subtypes of NMDA receptors while simultaneously having inhibitory effects at other subtypes. Such compounds could be important for adjusting imbalances in subtype activity and may have therapeutic potential as psychotropic agents.

Compounds that are useful for treating or preventing the adverse consequences of stroke, hypoglycemia, neurodegenerative disorders, anxiety, epilepsy or psychosis, or that induce analgesia, will inhibit the currents across the membranes of the oocyte expressing various subtype NMDA receptors. However, if the compound potentiates currents across the oocyte membrane, then the compound is expected to be useful in enhancing cognition.

With respect to Formulae I–XVII, above:

Typical $C_{6-14}$ aryl groups include phenyl, naphthyl, phenanthryl, anthracyl, indenyl, azulenyl, biphenyl, biphenylenyl and fluorenyl groups.

Typical halo groups include fluorine, chlorine, bromine and iodine.

Typical $C_{1-4}$ alkyl groups include methyl, ethyl, propyl, isopropyl, butyl, sec.-butyl, and tert.-butyl groups. Also contemplated is a trimethylene group substituted on two adjoining positions on any benzene ring of the compounds of the invention.

Typical C$_{2-4}$ alkenyl groups include ethenyl, propenyl, isopropenyl, butenyl, and sec.-butenyl.

Typical C$_{2-4}$ alkynyl groups include ethynyl, propynyl, butynyl, and 2-butnyyl groups.

Typical arylalkyl groups include any of the above-mentioned C$_{1-4}$ alkyl groups substituted by any of the above-mentioned C$_{6-14}$ aryl groups.

Typical arylalkenyl groups include any of the above-mentioned C$_{2-4}$ alkenyl groups substituted by any of the above-mentioned C$_{6-14}$ aryl groups.

Typical arylalkynyl groups include any of the above-mentioned C$_{2-4}$ alkynyl groups substituted by any of the above-mentioned C$_{6-14}$ aryl groups.

Typical haloalkyl groups include C$_{1-4}$ alkyl groups substituted by one or more fluorine, chlorine, bromine or iodine atoms, e.g., fluoromethyl, difluoromethyl, trifluoromethyl, pentafluoroethyl, 1,1-difluoroethyl and trichloromethyl groups.

Typical hydroxyalkyl groups include C$_{1-4}$ alkyl groups substituted by hydroxy, e.g., hydroxymethyl, hydroxyethyl, hydroxypropyl and hydroxybutyl groups.

Typical alkoxy groups include oxygen substituted by one of the C$_{1-4}$ alkyl groups mentioned above.

Typical alkylthio groups include sulphur substituted by one of the C$_{1-4}$ alkyl groups mentioned above.

Typical acylamino groups include any C$_{1-6}$ acyl (alkanoyl) substituted nitrogen, e.g., acetamido, propionamido, butanoylamido, pentanoylamido, hexanoylamido as well as aryl-substituted C$_{2-6}$ substituted acyl groups.

Typical acyloxy groups include any C$_{1-6}$ acyloxy groups, e.g., acetoxy, propionoyloxy, butanoyloxy, pentanoyloxy, hexanoyloxy and the like.

Typical heterocyclic groups include tetrahydrofuranyl, pyranyl, piperidinyl, piperizinyl, pyrrolidinyl, imidazolindinyl, imidazolinyl, indolinyl, isoindolinyl, quinuclidinyl, morpholinyl, isochromanyl, chromanyl, pyrazolidinyl and pyrazolinyl groups.

Typical heteroaryl groups include any one of the following which may be optionally substituted with one or more alkyl, halo, or hydroxy groups: thienyl, benzo[b]thienyl, naphtho[2,3-b]thienyl, thianthrenyl, furyl, pyranyl, isobenzofuranyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl phenoxazinyl groups, 1,4-dihydroquinoxaline-2,3-dione, 7-amino isocoumarin, pyrido[1,2-a]pyrimidin-4-one, 1,2-benzoisoxazol-3-yl, benzimidazolyl, 2-oxobenzimidazolyl, 2-oxindolyl and 4-nitrobenzofurazan.

Where the heteroaryl group contains a nitrogen atom in a ring, such nitrogen atom may be in the form of an N-oxide, e.g., a pyridyl N-oxide, pyrazinyl N-oxide, pyrimidinyl N-oxide and the like.

Typical amino groups include —NH$_2$, —NHR$^{14}$, and —NR$^{14}$R$^{15}$, wherein R$^{14}$ and R$^{15}$ are C$_{1-4}$ alkyl groups as defined above.

Typical carbonylamido groups are carbonyl groups substituted by —NH$_2$, —NHR$^{14}$, and —NR$^{14}$R$^{15}$ groups as defined above.

When the group is an amidino or guanidino group, any one of the nitrogen atoms may be substituted, e.g.,

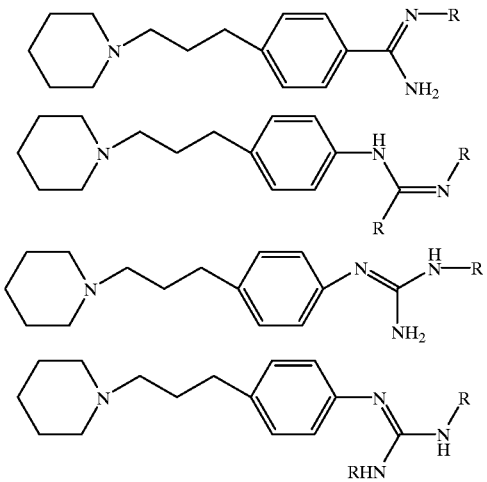

where each R is independently hydrogen, alkyl, or aryl.

Optional substituents on the aryl, aryloxy, arylthioxy, aroyl, heterocyclic, heterocycloxy, heteroaryl, heteroaryloxy, cycloalkyl, and cycloalkoxy groups listed above include any one of the typical halo, haloalkyl, aryl, fused aryl, heterocyclic, heteroaryl, alkyl, alkenyl, alkynyl, arylalkyl, arylalkenyl, arylalkynyl, hydroxyalkyl, nitro, amino, cyano, acylamido, hydroxy, thiol, acyloxy, azido, alkoxy, carboxy, carbonylamido, and alkylthiol groups mentioned above.

In the compounds having the above formulae, the group E is a linker group between the nitrogen, e.g., piperidine nitrogen, and the terminal group Y. Excluded from such Formulae are where two heteroatoms are adjacent to one another such that an unstable compound would be produced. Such adjacent heteroatoms include —O—O—, —O—S— (divalent sulfur), —N—S—(divalent sulfur), —S—O— (divalent sulfur), and —S—N—(divalent sulfur). Hydrazine groups (—N—N—) are contemplated as possible linkers. Preferably, the group E is an optionally substituted methylene linker. Most preferably, the group E is a methylene linker (CH$_2$)$_n$, wherein n is 1, 2, 3, 4, 5 or 6.

Preferably, the group Y is an N-hydroxyalkylpiperidinyl (e.g., hydroxypropyl) group, which is expected to provide a reduction in affinity to the a$_1$ receptor, thereby resulting in less hypotension when the compounds are administered to animals. See, Gifford, R. W. et al., Arch. Intern. Med. 153:154–183 (1993). Alternatively, a halo group such as a p-chlorophenyl group may be employed to give compounds having a prolonged in vivo activity.

Compounds having Formula I may be prepared by reaction of an appropriately substituted 1,2,3,4-tetrahydroisoquinoline with a suitable electrophile in an aprotic solvent such as toluene or acetonitrile. The starting 1,2,3,4-tetrahydroisoquinoline may be prepared by the Pictet-Spenger method described in Org. Reactions 6:151–206 (1951). Optionally, a base such as potassium carbonate or pyridine may be added. Examples of suitable electrophiles include, for example, an alkyl, alkenyl, alkynyl, aralkyl, aryloxyalkyl, or heteroaralkyl halide, sulfate, sulfonate, or isocyanate. Specific examples of such electrophiles include ethyl 3-bromoethoxyphenyl acetate, methyl 5-bromovalerate, ethyl 4-bromobutyrate, 3-butyn-1-methanesulfate, ethyl crotonate, 1-chloro-4-phenylbutane, 3-phenoxypropyl bromide, 4-chloro-4'- fluorobutyrophenone, 4-chlorobutyrophenone, 2-phenylethyl bromide, 1-bromo-3-phenylpropane, 3-phenoxypropyl bromide, g-bromo-phenetole, 3-phenoxypropyl bromide, 3-phenylpropyl bromide, 1,3-propanesulfone, phenylisocyanate, 4-nitrophenylisocyanate, allyl iodide, bromomethylcyclopropane, 3-bromo-1-propanol, and 5-bromovaleronitrile.

A general procedure for reaction of the piperidine-containing compound with an alkyl chloride, bromide, tosylate or mesylate involves forming a mixture of a free base of the amino derivative and an alkyl chloride or bromide in toluene, acetonitrile, DMF, acetone or ethanol, in the presence of NaI. The reaction may be refluxed for 1–10 h then cooled to room temperature, filtered and washed with hexane. The filtrate is evaporated, and the residue chromatographed over silica gel to give the product. If the product is a solid, it may be crystallized, for example, from hexane or hexane-ethyl acetate. If the product is an oil, it may be dissolved in acetone and 4N HCl solution in 1,4-dioxane or concentrated HCl may be added until the mixture becomes strongly acidic (pH<2). It may then be rota-evaporated, and co-evaporated until a solid residue is obtained. The solid may then be recrystallized from acetone to give the hydrochloride. Alternatively, the hydrobromide or other acid addition salts may be prepared by substitution of, for example, HBr or maleic acid for HCl.

Examples of compounds having Formula I include those having the Formula (Ia):

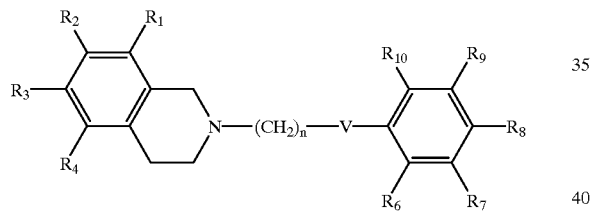

wherein $R_1$–$R_4$ and $R_6$–$R_{10}$ are independently hydrogen, halo, haloalkyl, aryl, fused aryl, a heterocyclic group, a heteroaryl group, alkyl, alkenyl, alkynyl, arylalkyl, arylalkenyl, arylalkynyl, hydroxyalkyl, nitro, amino, cyano, acylamido, hydroxy, thiol, acyloxy, azido, alkoxy, carboxy, carbonylamido, or alkylthiol;

n is 1, 2, 3, or 4; and

V is $CH_2$, oxygen, sulfur, or carbonyl (CO).

Other examples include those having the Formula (Ib):

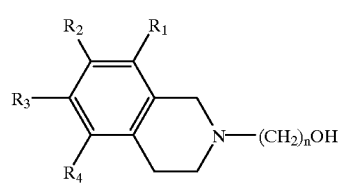

wherein $R_1$–$R_4$ are the same as described for formula Ia; and
n is 1, 2, 3, 4, 5, or 6.

Other examples include those having the Formula (Ic):

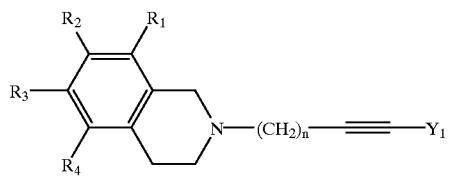

wherein $R_1$–$R_4$ are the same as described for formula Ia; and
$Y_1$ is alkyl, optionally substituted aryl, hydroxyalkyl, or optionally substituted alkaryl.

Other examples include those having the Formula (Id):

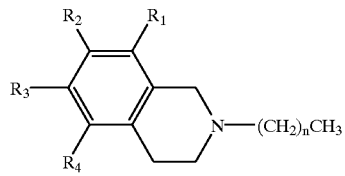

wherein $R_1$–$R_4$ are the same as described for formula Ia; and
n is 1, 2, 3, 4, 5, or 6.

Particular examples of compounds having Formula I include

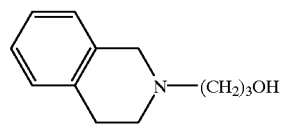

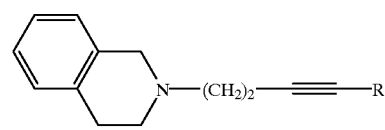

R = H, Ph;

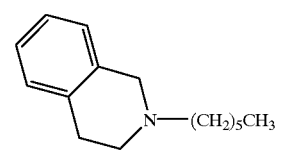

and

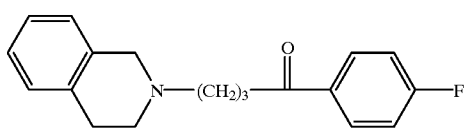

Compounds having Formula II may be prepared by reaction of an appropriately substituted 1,2,3,4-tetrahydro-9H-pyrido[3,4-b]indole with an electrophilic reagent as mentioned above. The starting 1,2,3,4-tetrahydro-9H-pyrido[3,4-b]indoles may be prepared according to Abou-Gharbia et al., *J. Med. Chem.*, 30:1818–1823 (1987) and Habert et al., *J. Med. Chem.*, 23:635–643 (1980).

Particular examples of compounds having Formula II include 2-(2-phenoxyethyl)-1,2,3,4-tetrahydro-9H-pyrido[3,4-b]indole, 2-(3-phenoxypropyl)-1,2,3,4-tetrahydro-9H-pyrido[3,4-b]indole, 2-(3-phenylpropyl)-1,2,3,4-tetrahydro-9H-pyrido[3,4-b]indole and 2-(3-hydroxypropy)-1,2,3,4-tetrahydro-9H-pyrido[3,4-b]indole.

Compounds having Formula IIa can be prepared similar to II. Particular examples of compounds having Formula IIa are

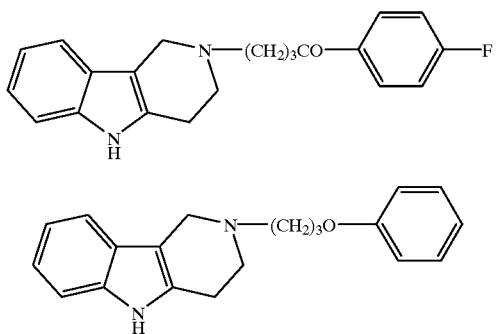

With regard to Formula III when p is >0, then the compounds may exist as a mixture of cis and trans isomers. The invention is directed to such cis and trans isomers as well as the individual enantiomers and diastereomeric mixtures.

When r is zero, G is NH and s is one, the N-amino piperidine compounds may be prepared according to Scheme 1:

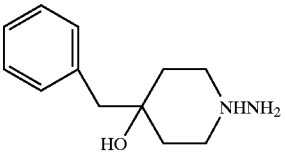

The N-amino piperidines may then be N-alkylated with one of the electrophiles listed above to give the compound of Formula III.

Also with regard to Formula III, when $R_1$ is an optionally substituted 2-aryloxyalkyl or an optionally substituted 2-benzyloxyalkyl-piperidine, the compounds may be prepared according to Scheme 2:

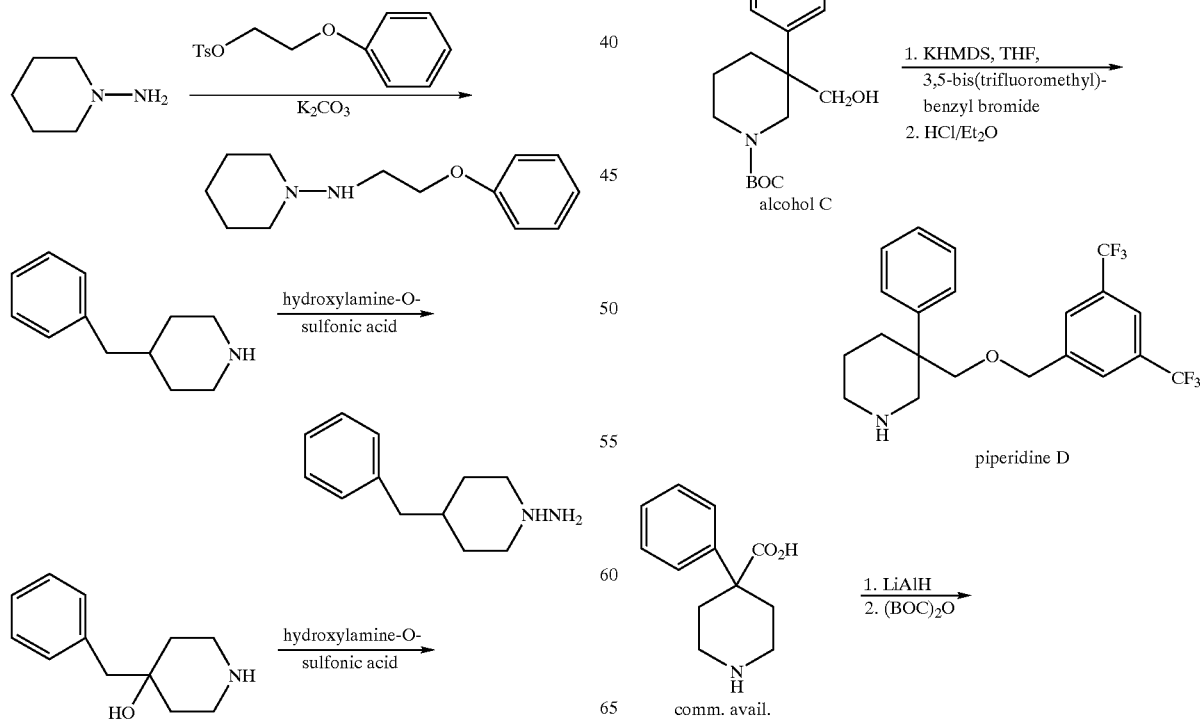

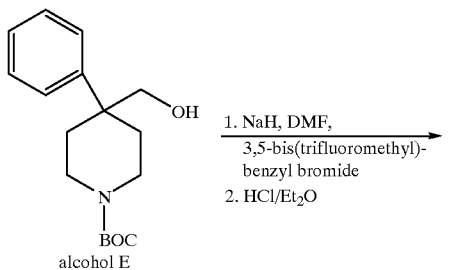

alcohol E

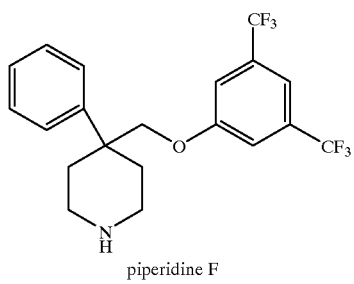

piperidine F

Scheme 2 may be generalized so that malonate A might be any of a variety of aryl or substituted benzyl malonates, for example, those shown below, leading to the corresponding derivatives in the scheme. Each of those piperidines may be alkylated with one or the other of the electrophilic reagents mentioned above.

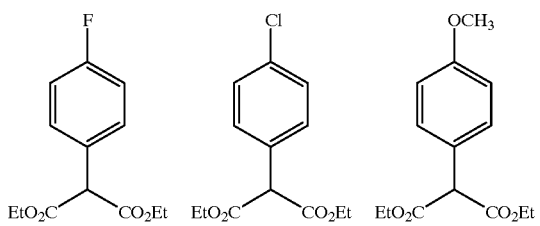

Scheme 3 depicts a route to some 2-substituted and 2,3-disubstituted-4-benzyl-4-hydroxypiperidines. A variety of electrophilic acylating agents may be used such that the final product 6 may have different substituents on the nitrogen atom. Also note that a variety of Grignard reagents or other nucleophiles can be used in the step 2→3 so that the final product 6 may contain various substituents at the 2-position. Also note that a variety of alkylating agents can be used in the step 3→4 so that the final product 6 will contain various substituents at the 3-position. Finally, the Grignard reagent in the step 4→5 can be used. Also note that a variety of Grignard reagents can be used so that the final product 6 will contain various substituents at the 4-position. Alkylating agents may also include $PhOCH_2Br$ and $PhCH_2OCH_2Br$, for example. These would introduce oxygen atoms in the substituents at the various positions. Additionally, a high degree of stereocontrol can be achieved with the likely relative stereochemical outcomes shown.

Scheme 3

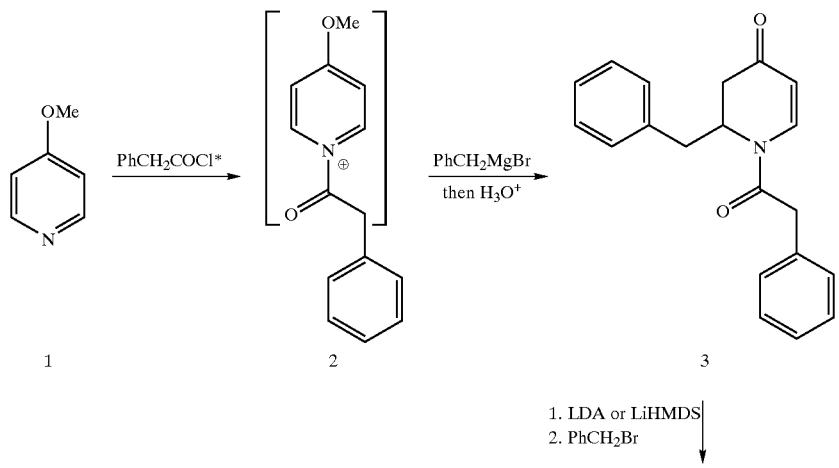

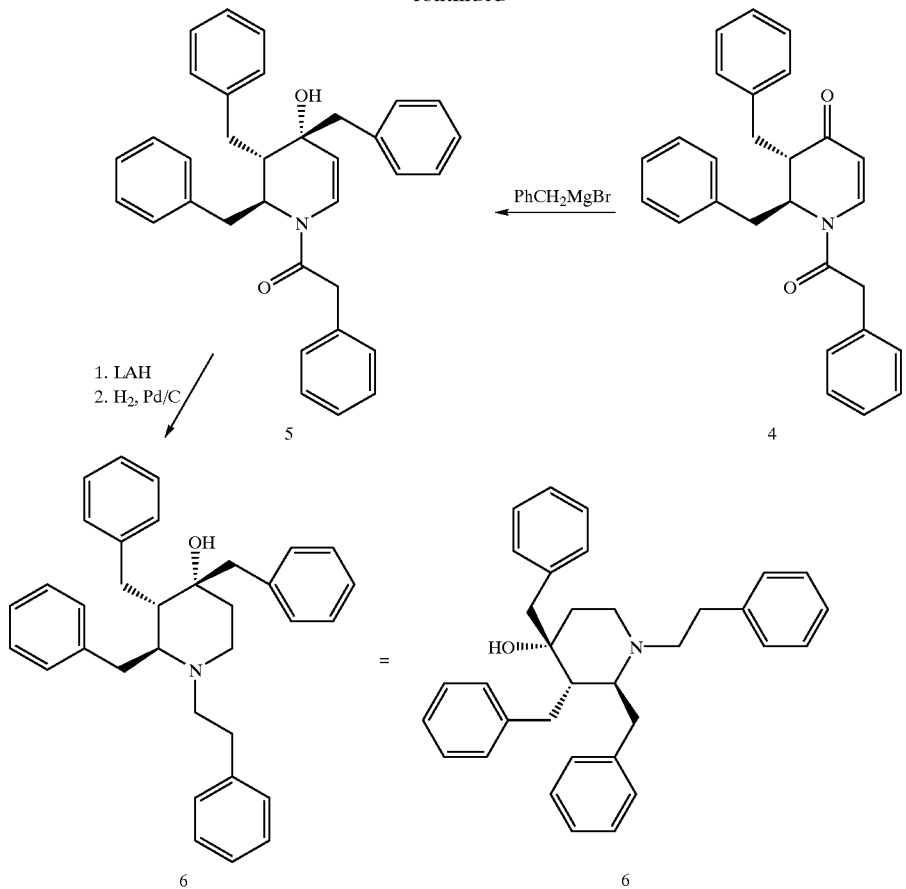

* Other commercially available electrophilic acylating agents which may be used in the first step of Scheme 3 include Ph(CH$_2$)$_2$COCl and PhOCH$_2$COCl.

Other variations of this versatile synthetic approach are also possible (See, Scheme 4). Again, the benzyl group was originally introduced as a Grignard reagent so that can be varied (see 2→3 above). The cuprate reagent can be varied as well as the final benzyl Grignard reagent. The net result of this chemistry is the preparation of 2,4,4,6-tetrasubstituted N-alkylpiperidines.

Scheme 4

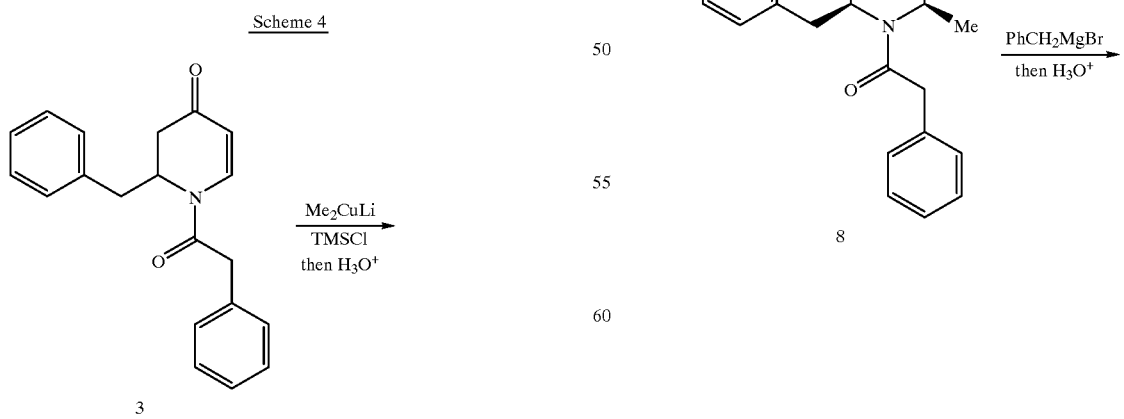

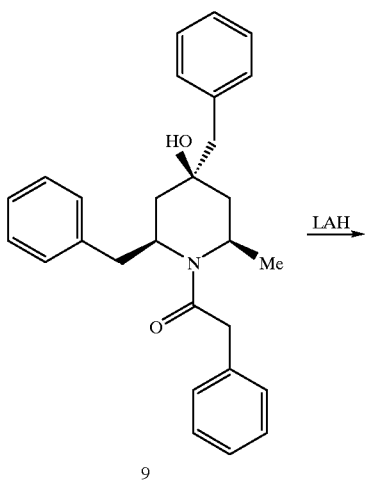
9
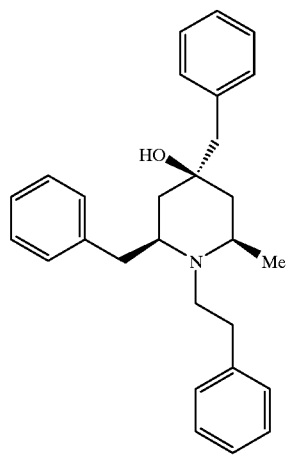
10
One can also take advantage of the ortho lithiation of methoxy pyridines described by Comins, D. L., et al., *Tetrahedron Lett.* 29 (1988). Routes to novel piperidines are illustrated in Scheme 5 below.
Scheme 5
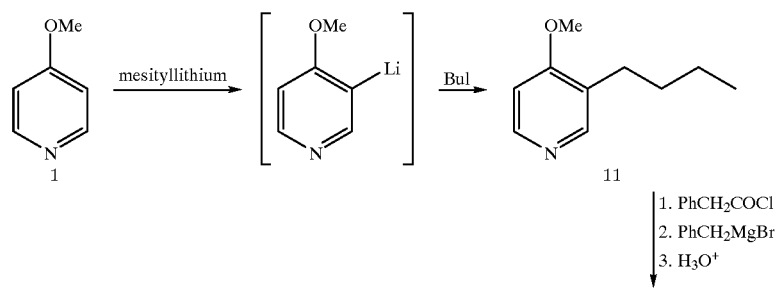
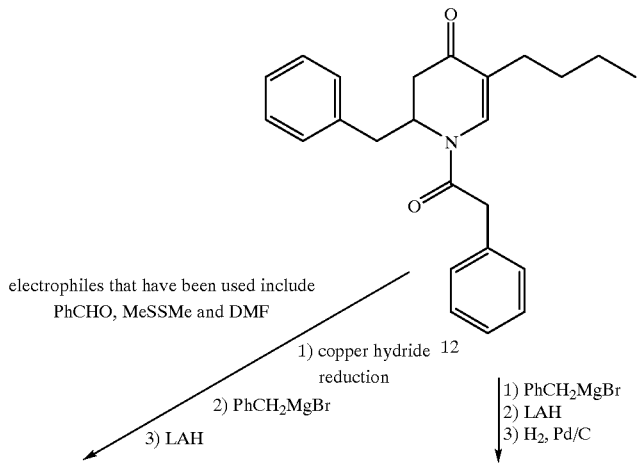

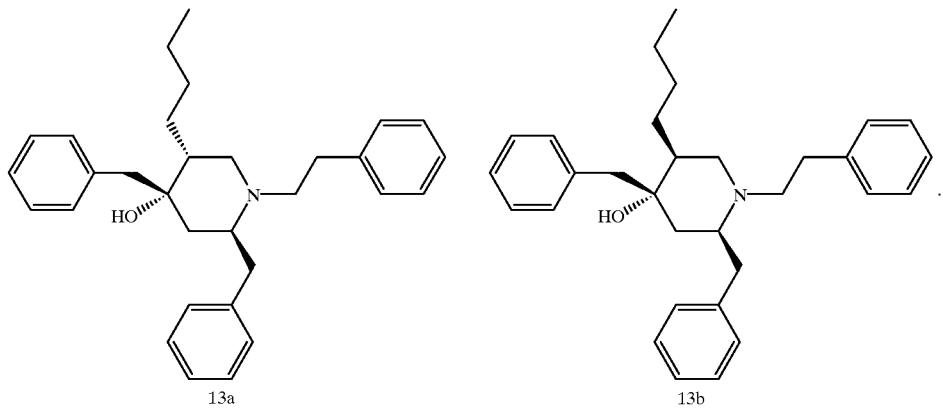

By choosing benzyl chloroformate as the initial electrophilic N-acylating agent, one can prepare a family of piperidines without a substituent on the nitrogen atom (Scheme 6). N-Phenoxycarbamates can be removed by catalytic hydrogenation with $PtO_2$ in ethanol (see Comins, D. L. et al., Tet. Lett. 32:5697 (1991)).

Carbamates formed from other chloroformates can be removed from 2,3-dihydro-4-pyridones by treatment with bases such as sodium methoxide in methanol under reflux. Then, the electrophilic reagents mentioned above may be used to alkylate these piperidine nitrogens. Also note that a variety of electrophilic reagents can be used so that the final products 13 will contain various substituents at the 5-position.

Scheme 6

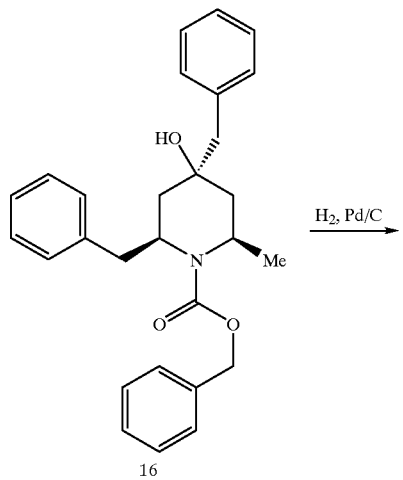

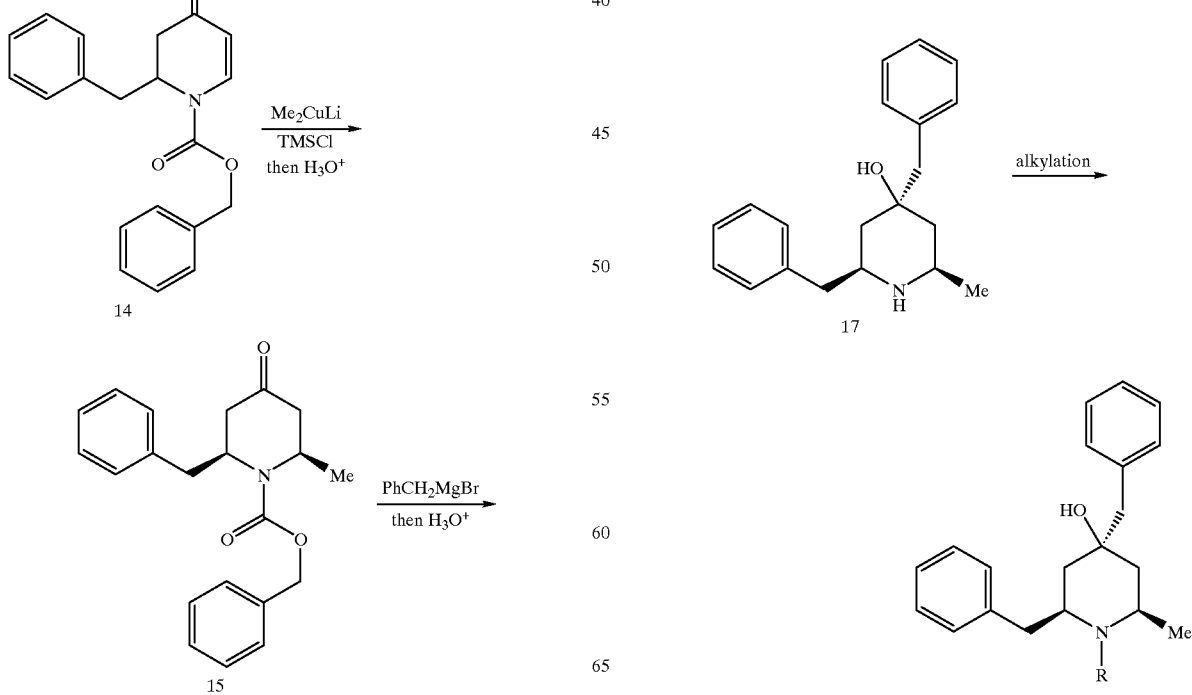

All of the above combinations can be readily made without the hydroxy substituent at C-4 of the piperidine as shown below via Wittig olefination of the piperidone followed by reduction (Scheme 7).
Scheme 7
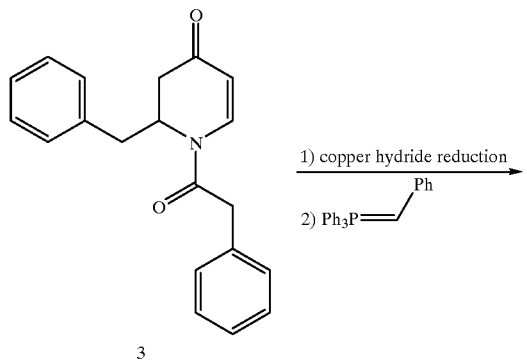
3
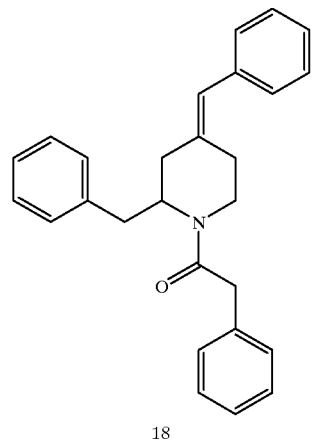
18
19
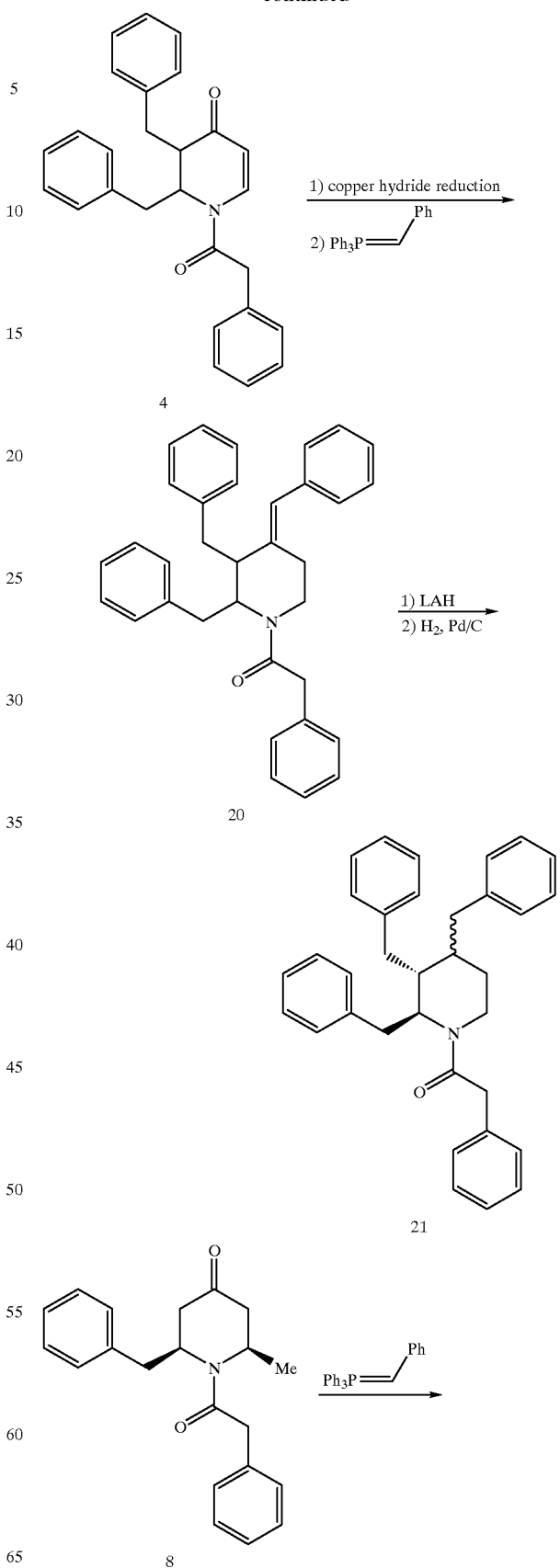
4
20
21
8

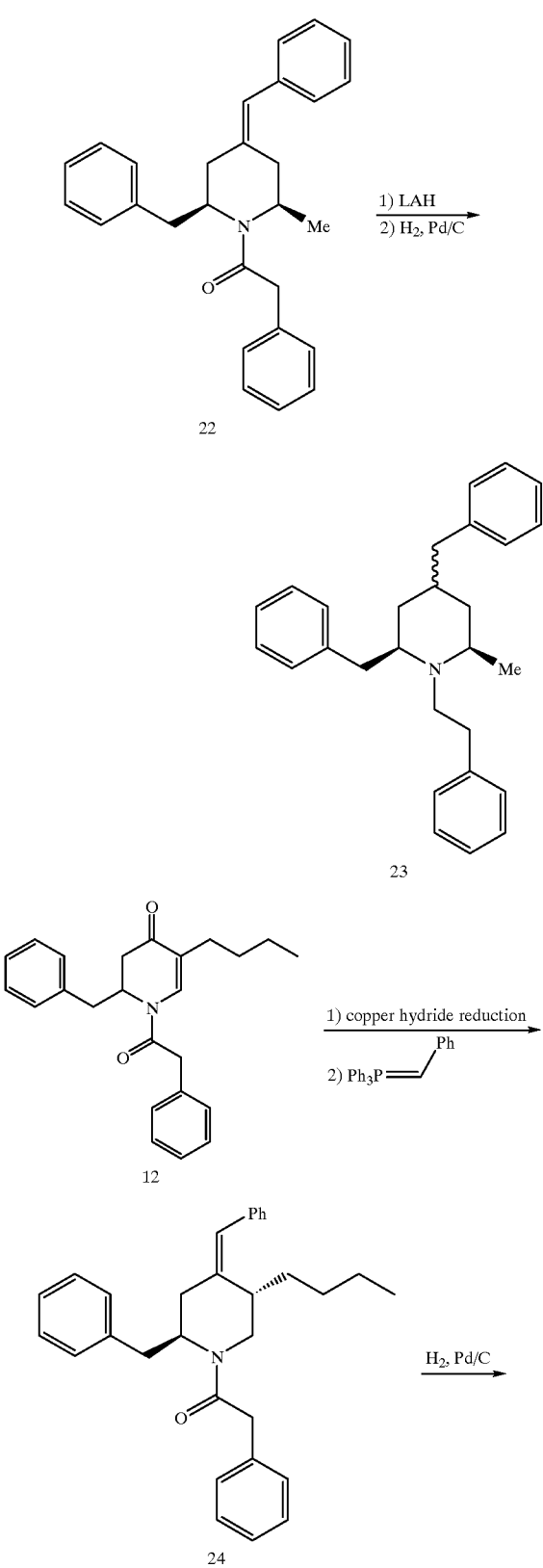
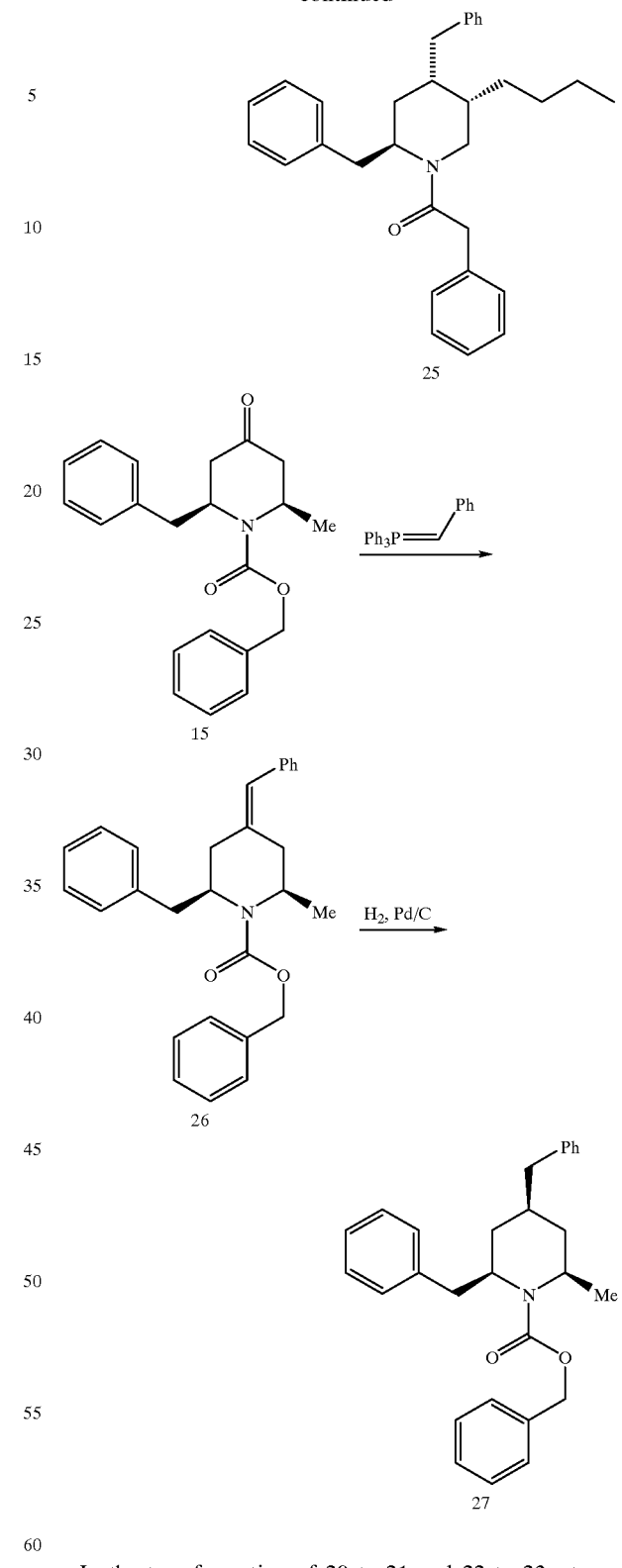
In the transformation of 20 to 21 and 22 to 23, stereo-control of the hydride reductions may be achieved by substituting other hydride reagents in place of LAH.

See, Comins, D. L., et al., *J. Org. Chem.* 55:2574 (1990), Comins, D. L., et al., *Tetrahedron Lett.* 29 (1988), and Comins, D. L., et al., *J. Am. Chem. Soc.* 116:4719 (1994).

An example of compounds having Formula III include those having Formula IIIa:

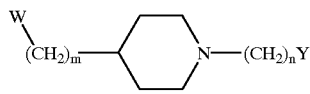

where in

W is an adamantyl group or an optionally substituted aryl group;

Y is $CH_3$, CN, $CO_2R$, carboxamido, an optionally substituted cycloalkyl group or an optionally substituted heterocycloalkyl group;

R is alkyl, an aminoalkyl group, an amidoalkyl group, a ureidoalkyl group, or a guanidinoalkyl group;

n is 0, 1, 2, 3, 4, 5, or 6; and m is 0, 1, 2, 3;

with the proviso, that when W is adamantyl, then Y may also be optionally substituted aryl, optionally substituted aryloxy, SAr, COAr, hydroxy, =—$Y_1$, =—$Y_1$, a heterocyclic group, a heteroaryl group, a cycloalkyl group, an amino group, an amido group, a ureido group, or a guanidino group; wherein $Y_1$ is hydrogen, alkyl, hydroxyalkyl, an optionally substituted aralkyl group, an optionally substituted aryl group, an aminoalkyl group, an amidoalkyl group, a ureidoalkyl group, or a guanidinoalkyl group.

Generally, when Y is an aminoalkyl or guanidinoalkyl, n must be greater than 1.

In general, compounds having Formula III may be prepared by reaction of an appropriately substituted piperidine with one of the electrophilic reagents mentioned above. Where W is an adamantyl group, the compounds may be prepared as shown in Scheme 8. Preferably, such adamantyl groups are 1-adamantyl.

Scheme 8

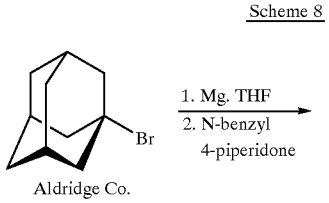

Aldridge Co.

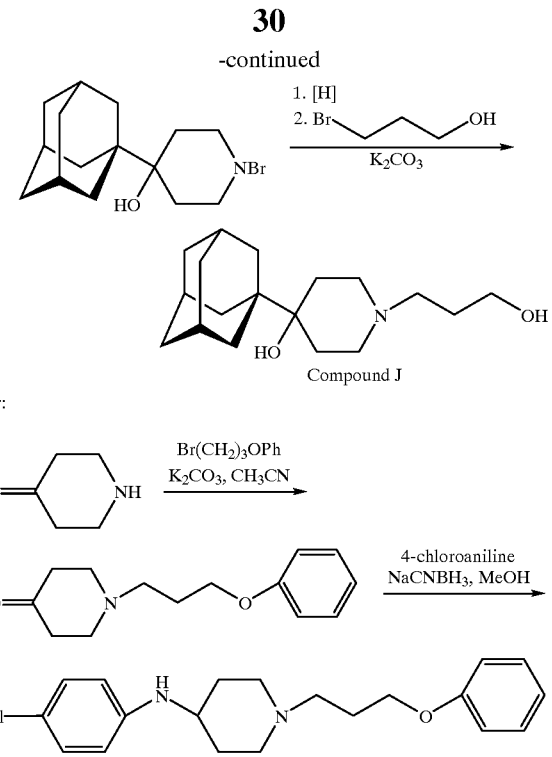

Compound J or:

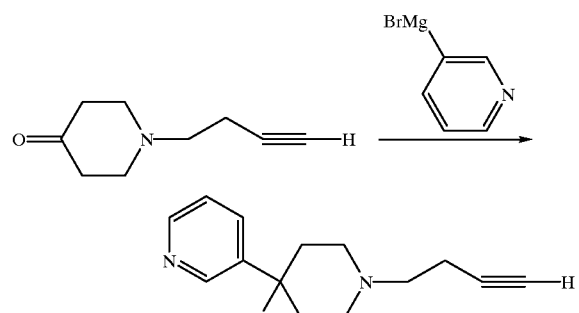

Where W is a heteroaryl group, the compounds may be prepared using an aryl lithium or grignard reagent as shown in Scheme 9.

Scheme 9

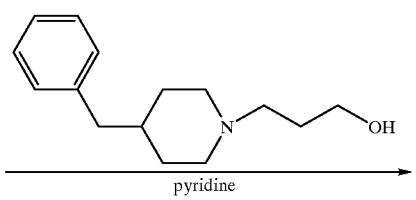

Where Y is a 7-substituted isocoumarin, the compounds may be prepared as set forth in Scheme 10.

Scheme 10

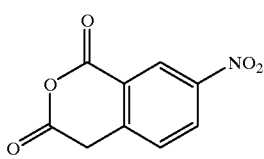

pyridine

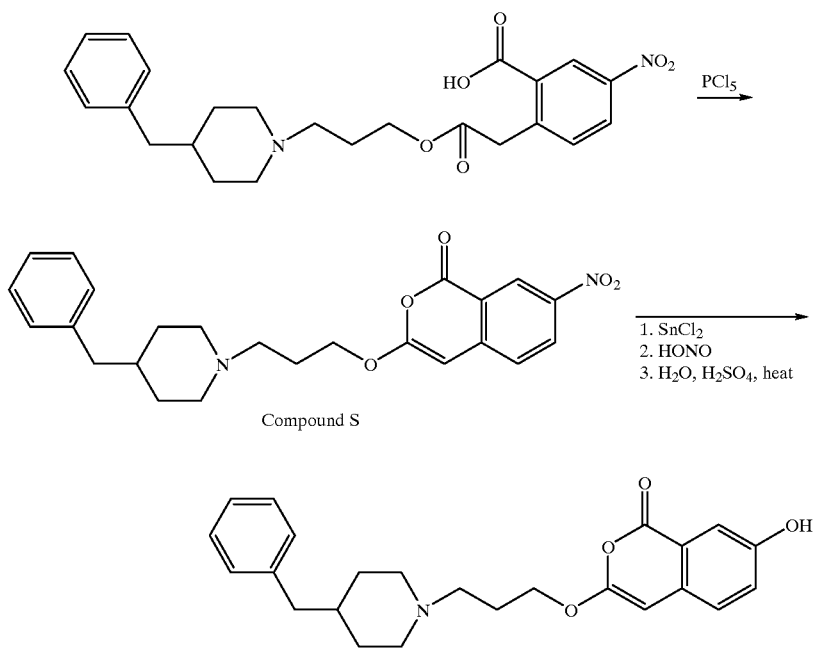

Compound S

See, Kerrigan et al., *J. Med. Chem.* 38:544 (1995) for methods of making such 7-substituted isocoumarins wherein the 7-substituent may be an amino group, a nitro group, or amido group.

Where Y is an optionally substituted cycloalkyl group or optionally substituted heterocycloalkyl group, and r, s and t are 0, the compounds may be prepared as shown in Scheme 11.

Scheme 11

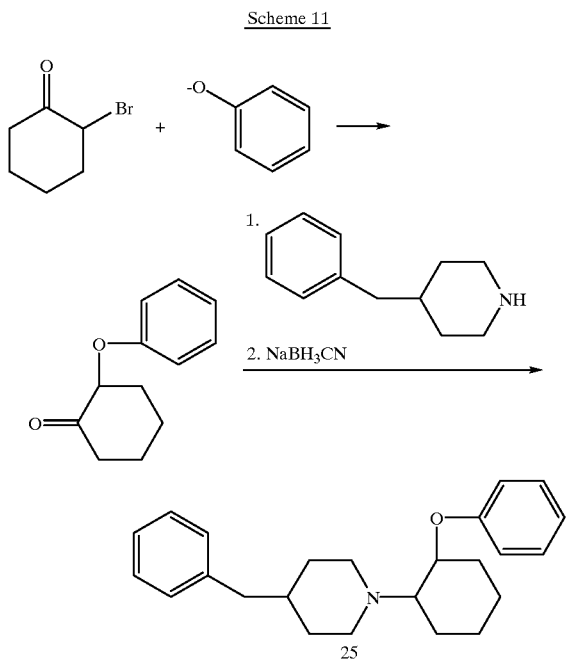

Other cyclized analogs include compounds such as 33–36.

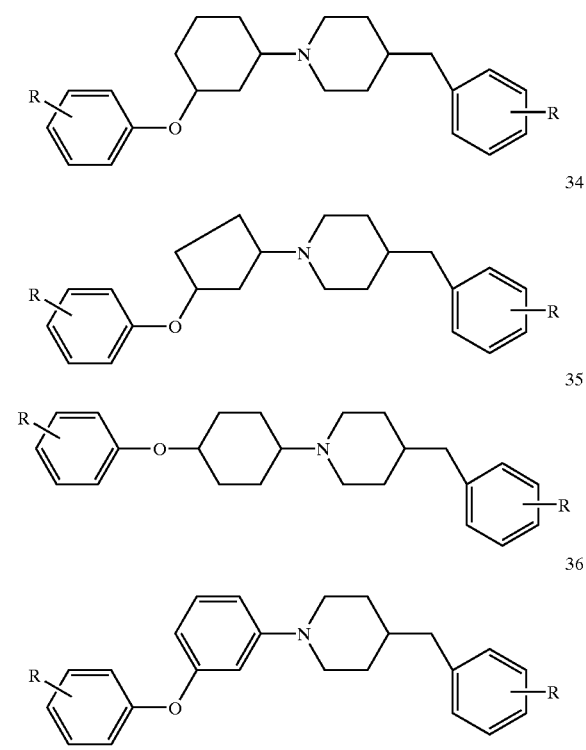

Another example of compounds within the scope of Formula III includes compounds having the Formula IIIb:

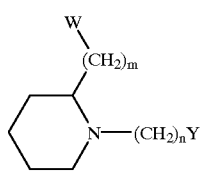

wherein
W is an adamantyl group or an optionally substituted aryl group;
Y is $CH_3$, CN, $CO_2R$, carboxamido, an optionally substituted cycloalkyl group or an optionally substituted heterocycloalkyl group;
R is alkyl, an aminoalkyl group, an amidoalkyl group, a ureidoalkyl group, or a guanidinoalkyl group;
n is 0, 1, 2, 3, 4, 5, or 6; and
m is 0, 1, 2, or 3;
with the proviso, that when W is adamantyl, then Y may also be optionally substituted aryl, optionally substituted aryloxy, SAr, COAr, hydroxy, ≡—$Y_1$, ═—$Y_1$, a heterocyclic group, a heteroaryl group, a cycloalkyl group, an amino group, an amido group, a ureido group, or a guanidino group; wherein
$Y_1$ is hydrogen, alkyl, hydroxyalkyl, an optionally substituted aralkyl group, an optionally substituted aryl group, an aminoalkyl group, an amidoalkyl group, a ureidoalkyl group, or a guanidinoalkyl group.

Another example includes compounds having the Formula IIIc:

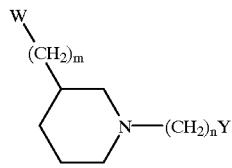

wherein
W is an adamantyl group or an optionally substituted aryl group;
Y is $CH_3$, CN, $CO_2R$, carboxamido, an optionally substituted cycloalkyl group, an optionally substituted heterocycloalkyl group, optionally substituted aryl, optionally substituted aryloxy, SAr, COAr, hydroxy, ≡—$Y_1$, ═—$Y_1$, a heterocyclic group, a heteroaryl group, an amino group, an amido group, a ureidoalkyl group, a guanidinoalkyl group, or O—N═$CR_1R_2$, where $R_1$ and $R_2$ are independently aryl or lower alkyl;
R is alkyl, an aminoalkyl group, an amidoalkyl group, a ureidoalkyl group, or a guanidinoalkyl group;
$Y_1$ is hydrogen, alkyl, hydroxyalkyl, an optionally substituted aralkyl group, an optionally substituted aryl group, an aminoalkyl group, an amidoalkyl group, a ureidoalkyl group, or a guinidinoalkyl group;
n is 0, 1, 2, 3, 4, 5, or 6; and
m is O, 1, 2, or 3;
with the proviso, that when W is adamantyl, then Y may also be optionally substituted aryl, optionally substituted aryloxy, SAr, COAr, hydroxy, ≡—$Y_1$, ═—$Y_1$, a heterocyclic group, a heteroaryl group, a cycloalkyl group, an amino group, an amido group, a ureido group, or a guanidino group; wherein
$Y_1$ is hydrogen, alkyl, hydroxyalkyl, an optionally substituted aralkyl group, an optionally substituted aryl group, an aminoalkyl group, an amidoalkyl group, a ureidoalkyl group, or a guanidinoalkyl group.

Another example includes compounds having the Formula IIId:

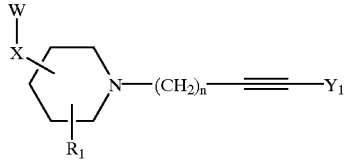

wherein
W is an adamantyl group or an optionally substituted aryl group;
X is a bond, $(CH_2)_m$, oxygen, or NR;
$Y_1$ is hydrogen, alkyl, hydroxyalkyl, an aminoalkyl group, an amidoalkyl group, a ureidoalkyl group, or a guanidinoalkyl group;
$R_1$ is hydrogen, hydroxy, halo, alkylcarboxy, optionally substituted aryl, optionally substituted aralkyl, optionally substituted aryloxyalkyl, optionally substituted benzyloxyalkyl, a heterocyclic group, a heterocyclic substituted alkyl group, heteroaryl, or a heteroaryl substituted alkyl group;
n is 0, 1, 2, 3, 4, 5, or 6; and
m is 0, 1, 2, or 3;
with the proviso that when W is an adamantyl group, then $Y_1$ may further be an optionally substituted aralkyl group, or an optionally substituted aryl group.

Where the compounds having Formula IIId terminate with an alkyne ($Y_1$=hydrogen), a propargylalcohol (Y=hydroxyalkyl), or propargylamine ($Y_1$=aminoalkyl) residue, they may be prepared according to Scheme 12.

Scheme 12

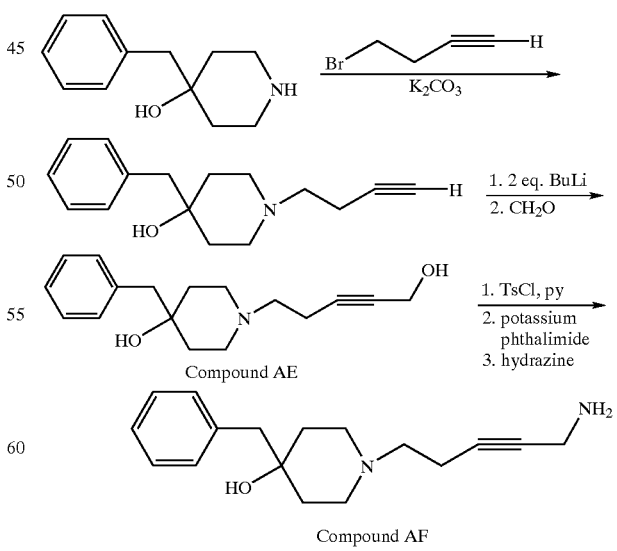

Another example includes compounds having the Formula IIIe:

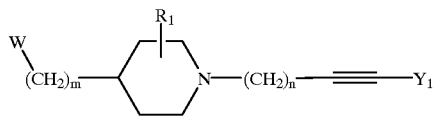

wherein

W is an adamantyl group or an optionally substituted aryl group;

$Y_1$ is hydrogen, alkyl, hydroxyalkyl, an aminoalkyl group, an amidoalkyl group, a ureidoalkyl group, or a guanidinoalkyl group;

$R_1$ is hydrogen, hydroxy, halo, alkylcarboxy, optionally substituted aryl, optionally substituted aralkyl, optionally substituted aryloxyalkyl, optionally substituted benzyloxyalkyl, a heterocyclic group, a heterocyclic substituted alkyl group, heteroaryl, or a heteroaryl substituted alkyl group;

n is 0, 1, 2, 3, 4, 5, or 6; and m is 0, 1, 2, or 3;

with the proviso that when W is an adamantyl group, then $Y_1$ may further be an optionally substituted aralkyl group, or an optionally substituted aryl group.

Another example includes compounds having the Formula IIIf:

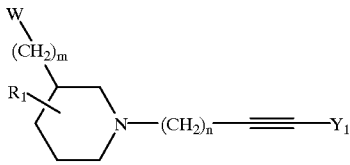

wherein

W, $Y_1$, $R_1$, n and m are the same as described in Formula IIIe;

with the proviso that when W is an adamantyl group, then $Y_1$ may further be an optionally substituted aralkyl group, or an optionally substituted aryl group.

Another example includes compounds having the Formula IIIg:

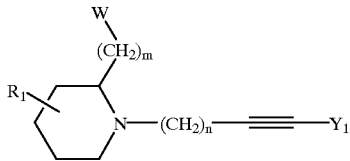

wherein

W, $Y_1$, $R_1$, n and m are the same as described in Formula IIIe;

with the proviso that when W is an adamantyl group, then $Y_1$ may further be an optionally substituted aralkyl group, or an optionally substituted aryl group.

Another example includes compounds having the Formula IIIh:

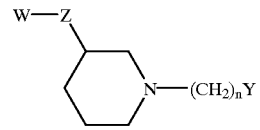

wherein

W is an adamantyl group or an optionally substituted aryl group;

Y is optionally substituted aryl, optionally substituted aryloxy, SAr, COAr, hydroxy, $\equiv\!\!-\!Y_1$, $=\!\!-\!Y_1$, a heterocyclic group, a heteroaryl group, a cycloalkyl group, an amino group, an amido group, a ureido group, or a guanidino group;

$Y_1$ is hydrogen, alkyl, hydroxyalkyl, an aminoalkyl group, an amidoalkyl group, a ureidoalkyl group, or a guanidinoalkyl group;

Z is $(CH_2)_m$, oxygen, sulfur, or NR;

m is 0, 1, 2, or 3; and n is 1, 2, 3, 4, 5, or 6.

Examples of compounds having Formula IIIh include 3-benzyl-1-(3-phenoxypropyl)piperidine, 3-benzyl-1-(2-phenoxyethyl)piperidine, 3-benzyl-1-(2-phenethyl) piperidine, 3-benzyl-1-[2-(3-trifluoromethyl)phenethyl] piperidine, 3-benzyl-1-[2-(4-aminophenyl)ethyl]piperidine, 3-benzyl-1-[2-(4-chlorophenyl)ethyl]piperidine, 3-benzyl-1-[2-(4-fluorophenyl)ethyl]piperidine, and 3-benzyl-1-[2-(4-methoxyphenyl)ethyl]piperidine.

Another example includes compounds having the Formula (IIIi):

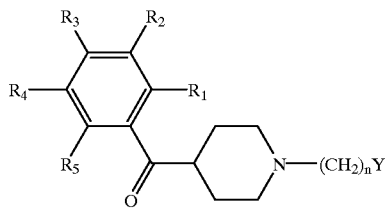

wherein $R_1$–$R_5$ are independently hydrogen, halo, haloalkyl, aryl, fused aryl, a heterocyclic group, a heteroaryl group, alkyl, alkenyl, alkynyl, arylalkyl, arylalkenyl, arylalkynyl, hydroxyalkyl, nitro, amino, cyano, acylamido, hydroxy, thiol, acyloxy, azido, alkoxy, carboxy, carbonylamido, or alkylthiol;

n is 1, 2, 3, 4, 5, or 6;

Y is optionally substituted aryl, optionally substituted aryloxy, SAr, COAr, hydrogen, hydroxy, $\equiv\!\!-\!Y_1$, $=\!\!-\!Y_1$, a heterocyclic group, a heteroaryl group, a cycloalkyl group, an amino group, an amido group, a ureido group, or a guanidino group; and $Y_1$ is hydrogen, alkyl, hydroxyalkyl, an optionally substituted aralkyl group, an optionally substituted aryl group, an aminoalkyl group, an amidoalkyl group, a ureidoalkyl group, or a guanidinoalkyl group.

Compounds having Formula IIIi may be prepared by reaction of the 4-benzoylpiperidine with one of the electrophiles listed above.

Another example includes compounds having Formula (IIIj):

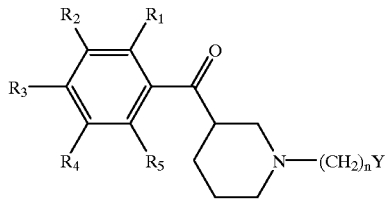

wherein $R_1$–$R_5$, n, Y and $Y_1$ are the same as described for formula IIIi.

Another example includes compounds having the Formula (IIIk):

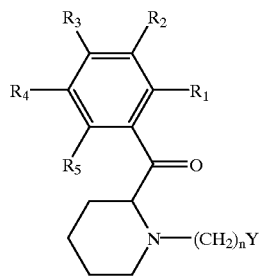

wherein $R_1$–$R_5$, n, Y and $Y_1$ are the same as described in formula IIIi.

Another example includes compounds having the Formula (IIIl):

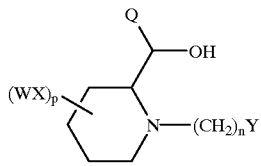

wherein

W is optionally substituted aryl;

Y is optionally substituted aryl, optionally substituted aryloxy, an optionally substituted aryloxy group, SAr, COAr, hydrogen, hydroxy, ≡—$Y_1$, =—$Y_1$, a heterocyclic group, a heteroaryl group, a cycloalkyl group, an amino group, an amido group, a ureido group, or a guanidino group;

$Y_1$ is hydrogen, alkyl, hydroxyalkyl, an optionally substituted aralkyl group, an optionally substituted aryl group, an aminoalkyl group, an amidoalkyl group, a ureidoalkyl group, or a guanidinoalkyl group;

Q is hydrogen, alkyl, aryl, aralkyl, a heterocyclic group, a heterocyclic substituted alkyl group, an aryl group, or an aralkyl group;

X is a bond, $(CH_2)_m$, oxygen, or sulfur;

m is 0, 1, 2, or 3;

n is 1, 2, 3, 4, 5, or 6; and p is 0 or 1.

Another example includes compounds having the Formula (IIIm):

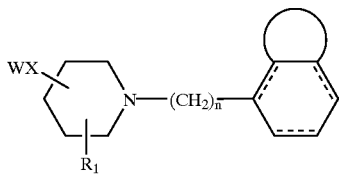

wherein

W is optionally substituted aryl;

X is a bond, $(CH_2)_m$, oxygen, sulfur, or NR;

R is alkyl, hydroxy, an aminoalkyl group, an amidoalkyl group, a ureidoalkyl group, or a guanidinoalkyl group;

$R_1$ is hydrogen, hydroxy, aryl, or aralkyl;

n is 1, 2, 3, 4, 5, or 6;

═ ─ ═ single or double bond; and

◯=carbon ring or heterocyclic ring, with the proviso that said carbon ring is not part of a naphthyl group.

Compounds having Fomula IIIm may be prepared by a Diels-Alder reaction as shown below:

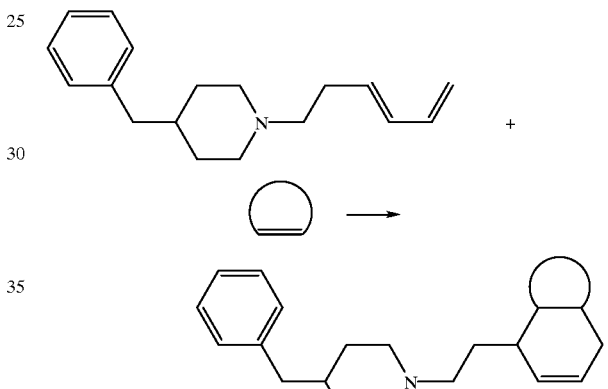

Another example includes compounds having the Formula (IIIn):

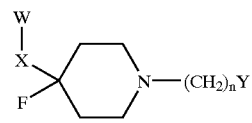

wherein

W is an adamantyl group or an optionally substituted aryl group;

X is a bond or $(CH_2)_m$;

Y is $CH_3$, CN, $CO_2R$; an optionally substituted aryl group, an optionally substituted aryloxy group, SAr, COAr, hydroxy, ≡—$Y_1$, =—$Y_1$, a heterocyclic group, a heteroaryl group, a cycloalkyl group, an amino group, an amido group, a ureido group, or a guanidino group;

$Y_1$ is hydrogen, alkyl, hydroxyalkyl, an optionally substituted aralkyl group, an optionally substituted aryl group, an aminoalkyl group, an amidoalkyl group, a ureidoalkyl group, or a guanidinoalkyl group R is alkyl, hydroxy, an aminoalkyl group, an amidoalkyl group, a ureidoalkyl group, or a guanidinoalkyl group;

n is 0, 1, 2, 3, 4, 5, or 6; and m is 0, 1, 2, or 3.

Compounds having Formula IIIn, where the group $R_1$ is fluoro, may be prepared by reaction of the corresponding hydroxy piperidine with diethylaminosulfur trifluoride as shown in Scheme 13.

Scheme 13

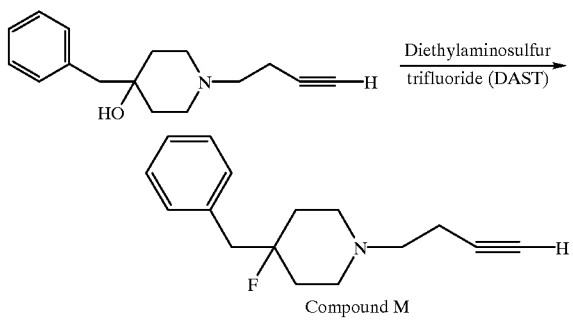

Compound M

See, Sharma, R. A.; Korytnyk, W.; *Tetrahedron Lett* 573 (1977); and Fieser, L. F.; Fieser, M. *Reagents for Organic Synthesis* 6:183 (1977).

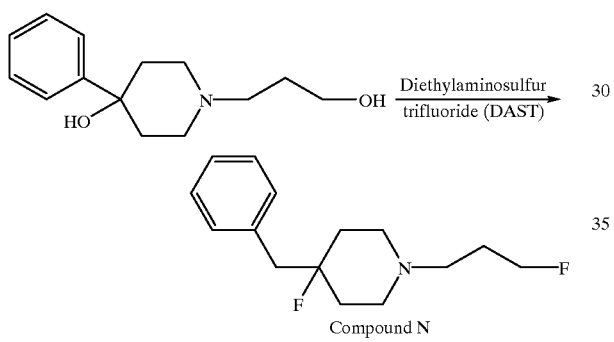

Compound N

An example of compounds having Formula IIIn includes:

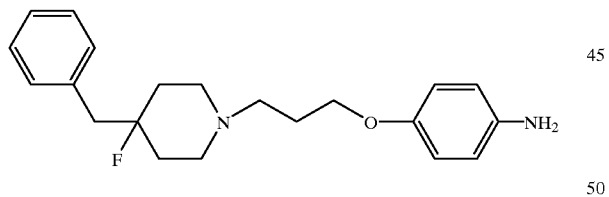

Another example includes compounds having the Formula (IIIo):

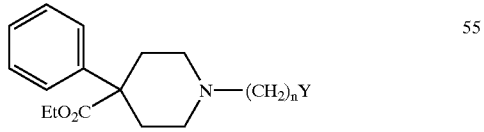

wherein

Y is hydrogen, hydroxy, $CH_3$, CN, $CO_2R$, optionally substituted aryl, optionally substituted aryloxy, optionally substituted arylthioxy, optionally substituted aroyl, $=-Y_1$, $=-Y_1$, optionally substituted heterocyclic group, optionally substituted heterocycloxy, optionally substituted heteroaryl, optionally substituted heteroaryloxy, optionally substituted cycloalkyl group, optionally substituted cycloalkoxy group, amino, amido, ureido, or guanidino;

$Y_1$ is hydrogen, alkyl, hydroxyalkyl, optionally substituted aralkyl, an optionally substituted aryl, aminoalkyl, amidoalkyl, ureidoalkyl, or guanidinoalkyl; and n is 0, 1, 2, 3, 4, 5 or 6.

Compounds having Formula IIIo may be prepared according to Scheme 14.

Scheme 14

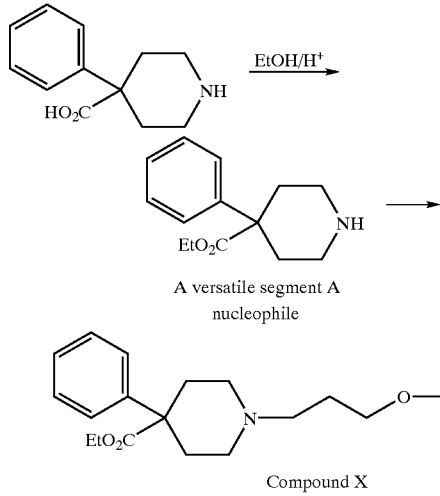

A versatile segment A nucleophile

Compound X

Particular examples of compounds having Formula III include:

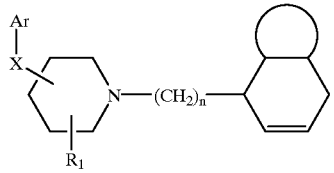

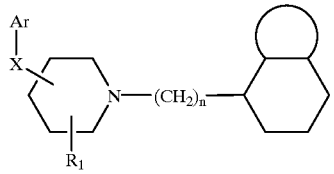

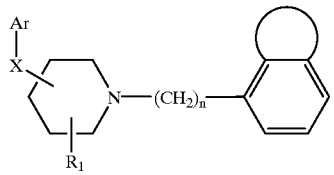

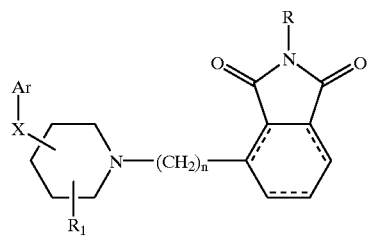

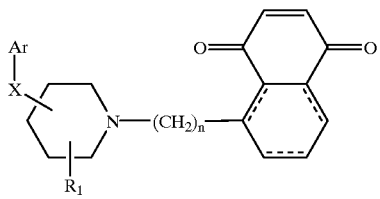
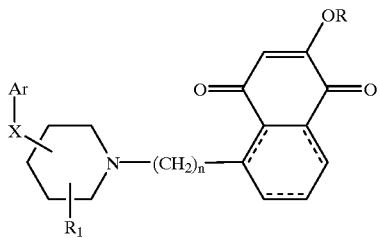
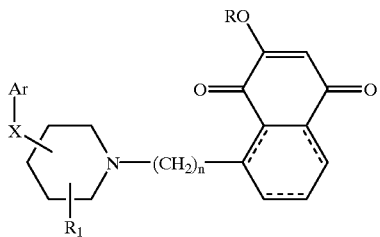
wherein n is 0, 1, 2, 3, 4, 5 or 6;
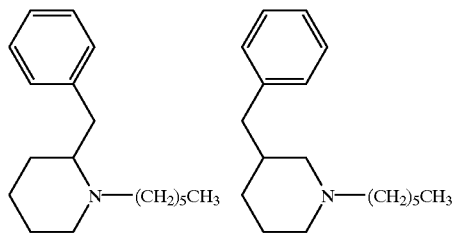
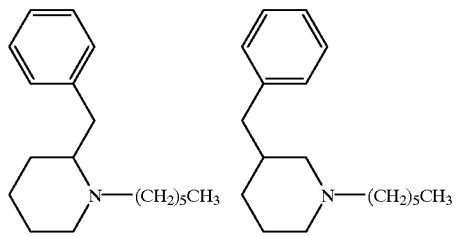
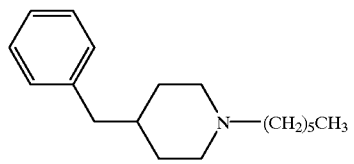
n = 1, 2;
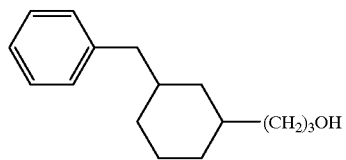
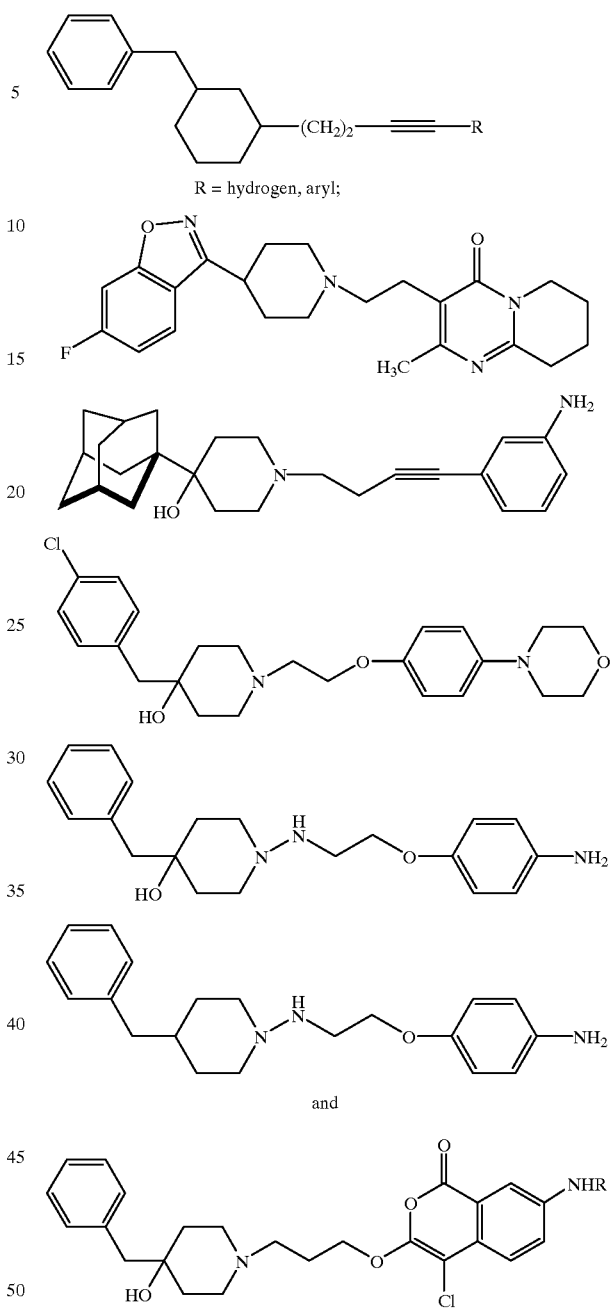
and
Scheme 15
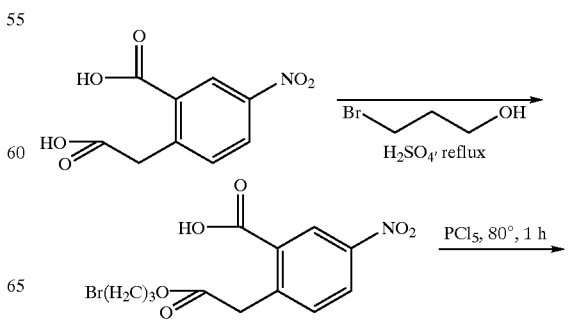

-continued

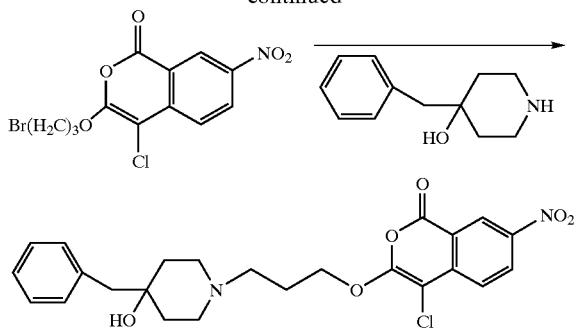

Method of Harper and Powers, *Biochemistry* 24:7200–7213 (1985).

Additional compounds having Formula III include 4-benzyl-1-(3-hydroxy-1-methylpropyl)piperidine, 4-benzyl-1-(2-hydroxyethyl)piperidine, 1-benzyl-3-hydroxy-3-phenylpiperidine, 3-hydroxy-3-phenyl-1-phenethylpiperi-dine, 3-hydroxy-3-phenyl-1-(phenylpropyl)piperidine, and 4-benzoyl-1-(3-hydroxypropyl)piperidine.

Examples of compounds having Formula IV include those having the Formula (IVa):

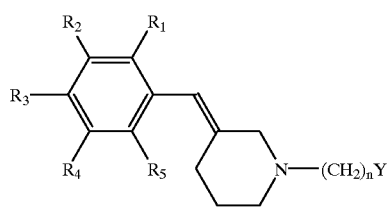

wherein
$R_1$–$R_5$ are independently hydrogen, halo, haloalkyl, aryl, fused aryl, a heterocyclic group, a heteroaryl group, alkyl, alkenyl, alkynyl, arylalkyl, arylalkenyl, arylalkynyl, hydroxyalkyl, nitro, amino, cyano, acylamido, hydroxy, thiol, acyloxy, azido, alkoxy, carboxy, carbonylamido, or alkylthiol;

n is 1, 2, 3, 4, 5, or 6;

Y is optionally substituted aryl, optionally substituted aryloxy, SAr, COAr, hydrogen, hydroxy, =—$Y_1$, =—$Y_1$, a heterocyclic group, a heteroaryl group, a cycloalkyl group, an amino group, an amido group, a ureido group, or a guanidino group; and $Y_1$ is hydrogen, alkyl, hydroxyalkyl, an optionally substituted aralkyl group, an optionally substituted aryl group, an aminoalkyl group, an amidoalkyl group, a ureidoalkyl group, or a guanidinoalkyl group.

Another example includes compounds having the Formula (IVb):

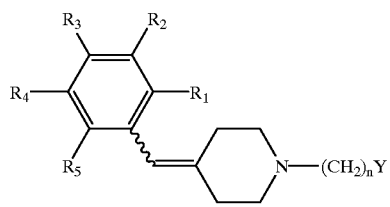

wherein
$R_1$–$R_5$, n, Y and $Y_1$ are the same described in formula IVa.

Compounds having Formula IV may be prepared by reaction of the corresponding piperidone with a Wittig reagent derived from a benzyl bromide. Alternatively, a benzyl grignard reagent may be reacted with the piperidone to give the hydroxybenzyl piperidine which may be dehydrated with sulfuric acid and heat.

Particular examples of compounds having Formula IV include 1-benzyl-4-(m-fluorobenzylidene)piperidine, 1-(3-hydroxypropyl)-4-benzylidenepiperidine, and 1-hexyl-4-benzylidenepiperidine.

Compounds having Formula V may be prepared according to Scheme 16 followed by reaction with one of the electrophiles mentioned above.

Scheme 16

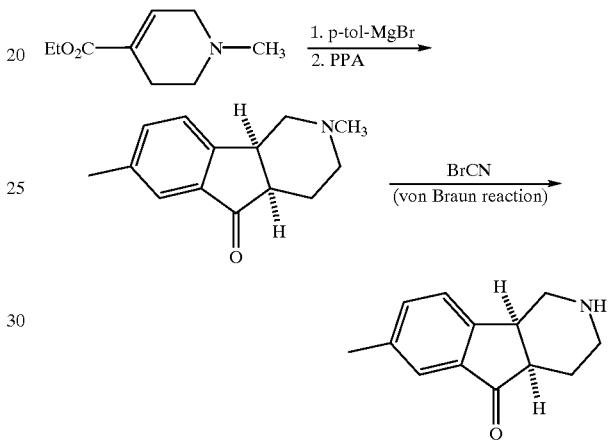

See, Cook et al., *J. Ned. Chem.* 38:754 (1995).

An example of compounds having Formula V include:

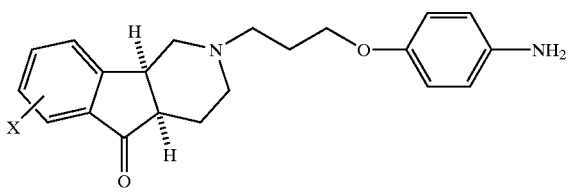

Compounds having Formula VI may be prepared according to Scheme 17.

Scheme 17

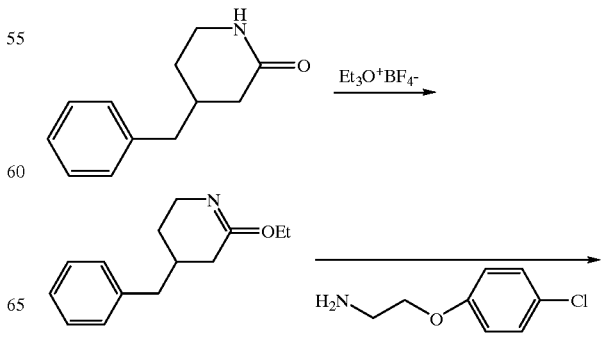

-continued
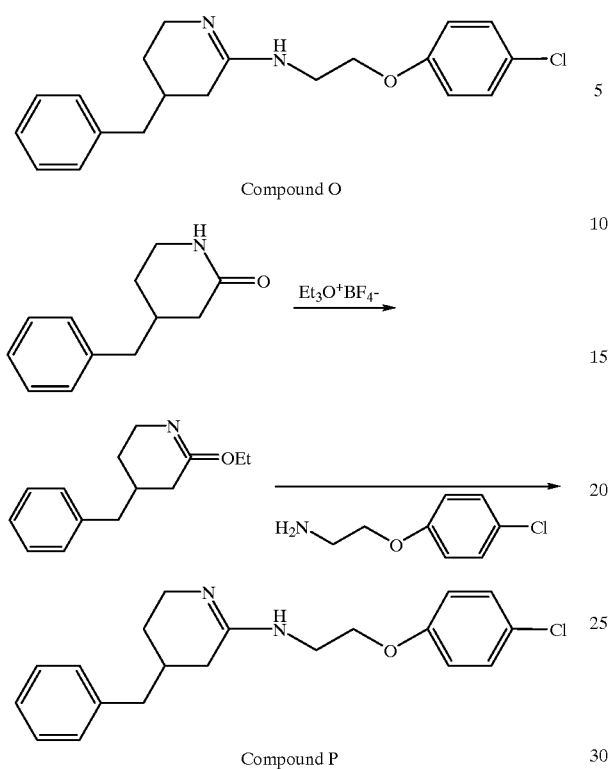
By varying the choice of the amine nucleophile, one can synthesize a family of amidines including the following:
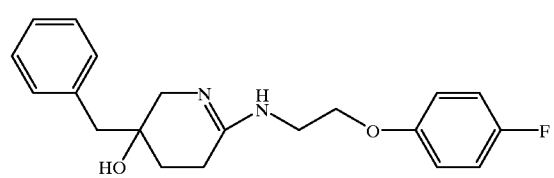
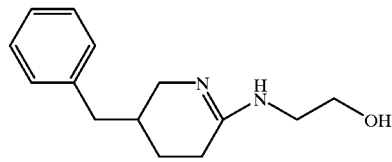
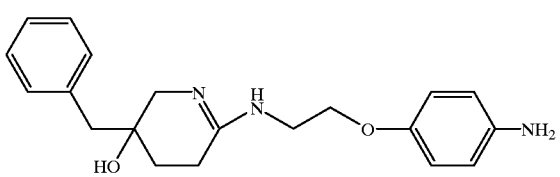
and
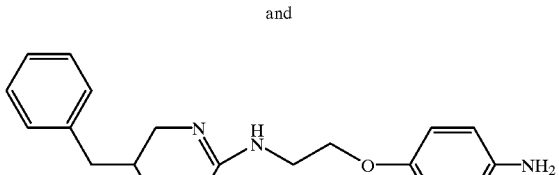
Compounds having Formula VII may be prepared according to Scheme 18.
Scheme 18
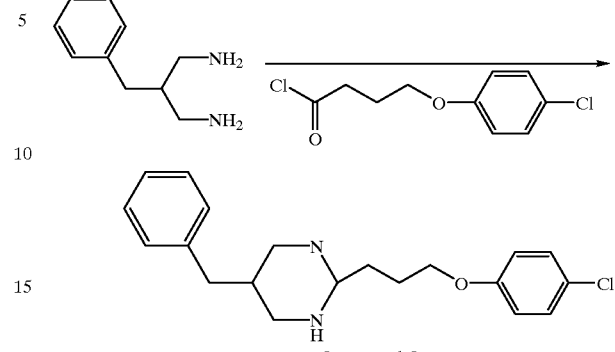
Examples of compounds having Formula VII include:
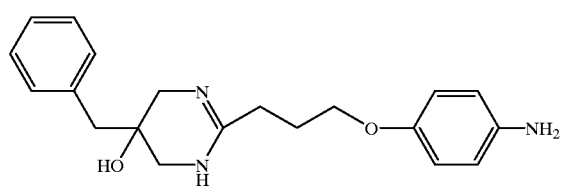
and
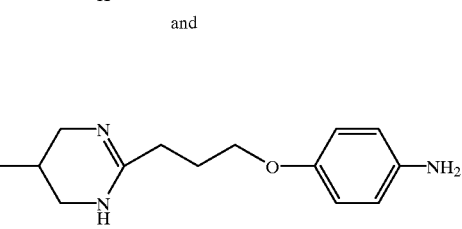
Compounds having Formula VIII may be prepared according to Scheme 19.
Scheme 19
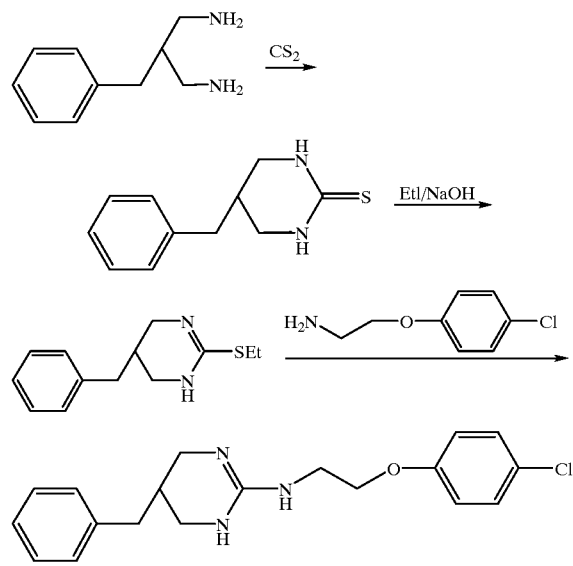

Examples of compounds having Formula VIII include:

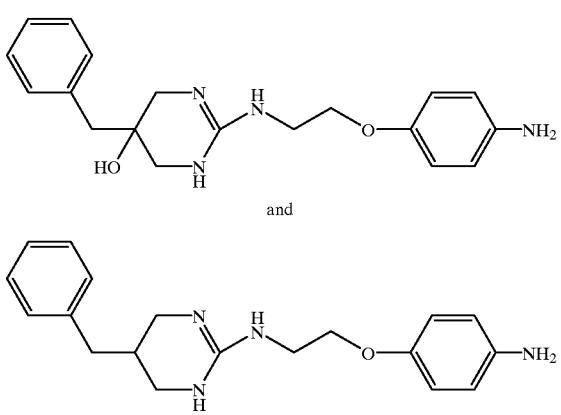

and

Compounds having Formula IX may be prepared according to Scheme 20.

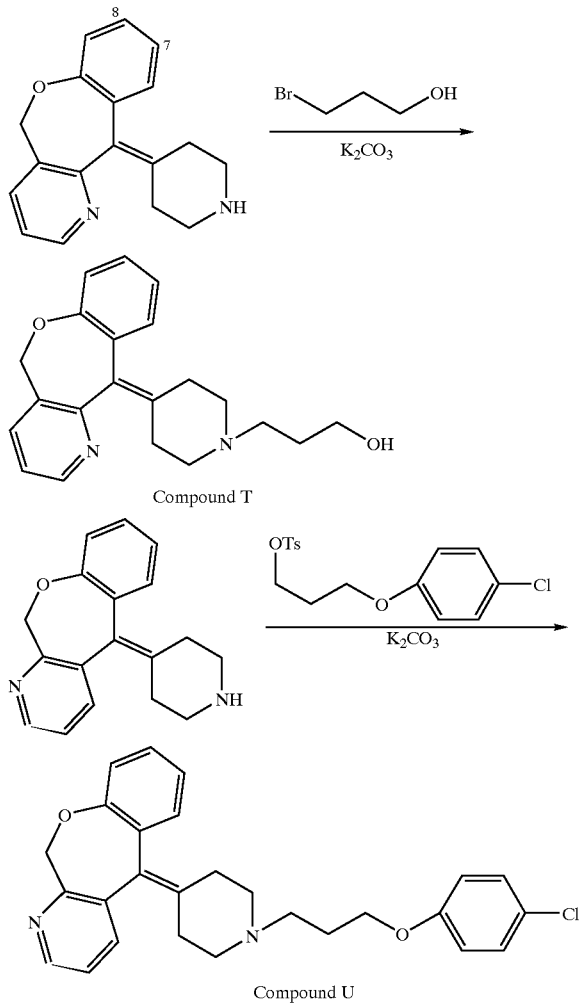

See, Iwasaki, N., et al., *J. Med. Chem* 38:496 (1995), who describe a variety of substituents in the 7-, 8- and 9-positions including fluoro, chloro, methoxy and nitro on the top left benzene ring.

Compounds having Formula X may be prepared according to Scheme 21.

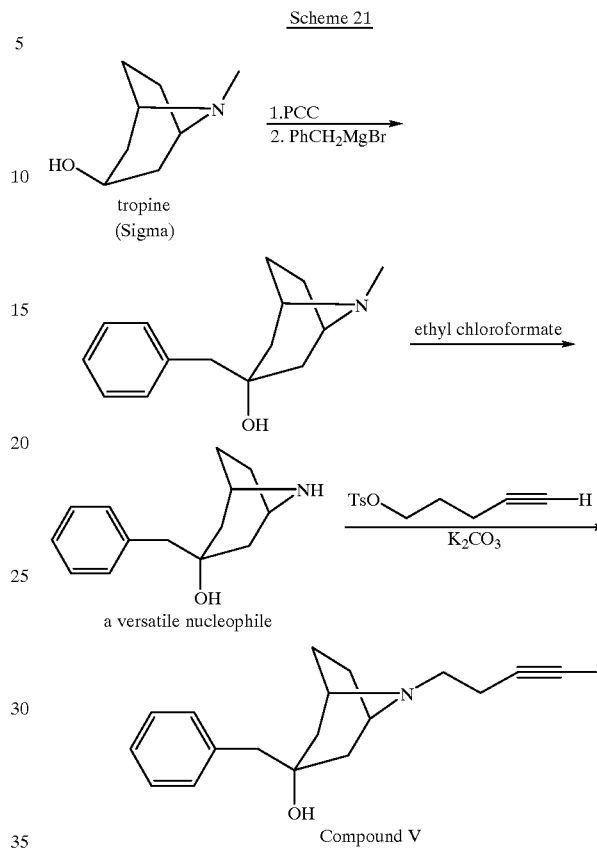

Compounds having Formula XI may be prepared according to Scheme 22.

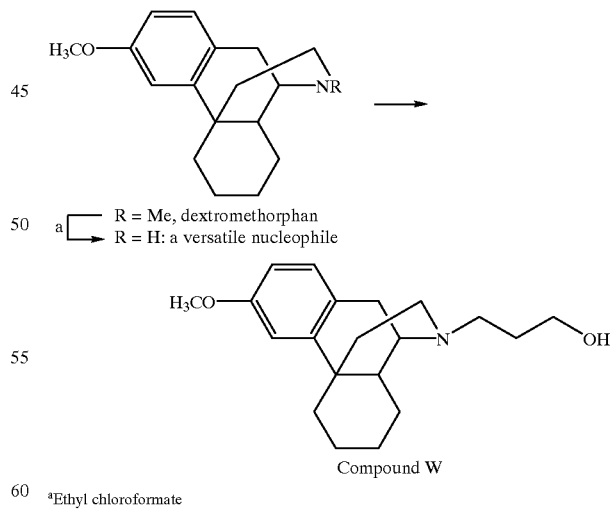

[a] Ethyl chloroformate

Compounds having Formula XII may be prepared by reaction of the corresponding 10,11-dihydro-5H-dibenzo[a,d]cyclohepten-5,10-imines with one of the electrophilic reagents listed above. Methods for preparing the starting 10,11-dihydro-5H-dibenzo[a,d]cyclohepten-5,10-imines are disclosed in U.S. Pat. No. 4,399,141, the disclosure of which is fully incorporated by reference herein.

Particular examples of compounds having Formula XIII include those having the Formula (XIIIa):

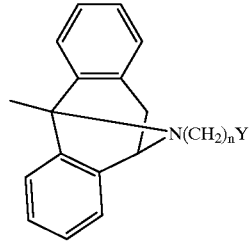

wherein

Y is hydrogen, hydroxy, $CH_3$, CN, $CO_2R$, optionally substituted aryl, optionally substituted aryloxy, optionally substituted arylthioxy, optionally substituted aroyl, $\equiv$—$Y_1$, $=$—$Y_1$, optionally substituted heterocyclic group, optionally substituted heterocycloxy, optionally substituted heteroaryl, optionally substituted heteroaryloxy, optionally substituted cycloalkyl group, optionally substituted cycloalkoxy group, amino, amido, ureido, or guanidino; $Y_1$ is hydrogen, alkyl, hydroxyalkyl, optionally substituted aralkyl, an optionally substituted aryl, aminoalkyl, amidoalkyl, ureidoalkyl, or guanidinoalkyl; and n is 0, 1, 2, 3, 4, 5, or 6.

Compounds having Formula XIII may be prepared by reaction of the corresponding 10,5-(iminomethano)-10,11-dihydro-5H-dibenzo[a,d]-cycloheptenes (IDDCs) with one of the electrophilic reagents listed above. Methods for preparing the starting IDDCs are disclosed in U.S. Pat. No. 5,011,834, the disclosure of which is fully incorporated by reference herein.

Particular examples of compounds having Formula XIV include those having the Formula (XIVa):

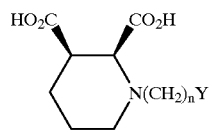

wherein

Y, $Y_1$ and n are the same as described for formula XIIIa.

Another example includes those having the Formula (XIVb):

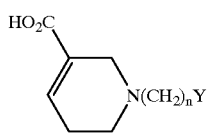

wherein

Y, $Y_1$ and n are the same as described in formula XIIIa.

Another example includes those compounds having the Formula (XIVc):

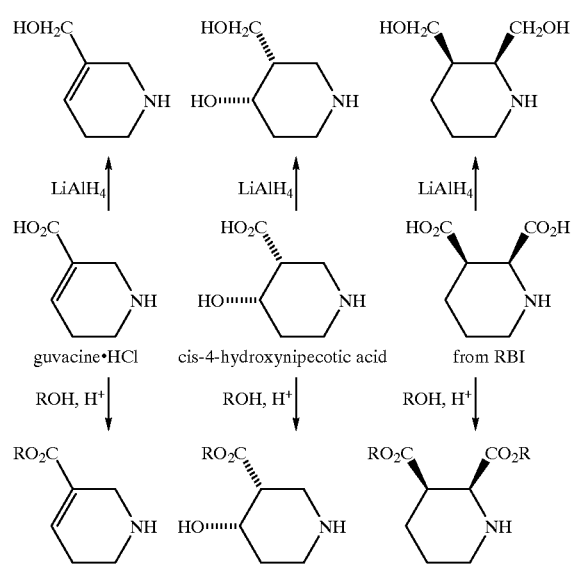

wherein

Y, $Y_1$ and n are the same as described in formula XIIIa.

Compounds having Formula XIV may be prepared as shown in Scheme 23. These compounds may be derived from guvacine or 4-hydroxynipecotic acid and reacted with one of the electrophiles listed above to give the desired product.

Scheme 23

RBI is Research Biochemicals International, Inc.

Compounds having Formula XV may be prepared by reaction of an appropriate nitrogen electrophile with a suitable electrophile XEY. Particular examples of compounds having Formula XV are

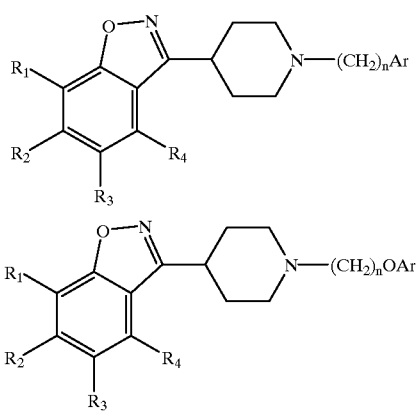

Examples of compounds of Formula XVI include those having the Formula (XVIa):

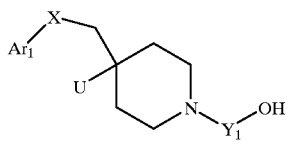

wherein $Y_1$ is $(CHR_2)_n$ wherein n is 0, 1, 2, 3 or 4; and $Ar_1$, X, U and $R_2$ are as previously described by Formula XVI.

Other examples include those having Formula (XVIb):

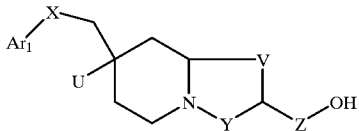

wherein

V is $(CH_2)_q$ wherein q is 1, 2 or 3 and $Ar_1$, X, U, Y and Z are previously described for Formula XVI.

The N-(hydroxyalkyl)piperidines of Formula XVI are selective antagonists of the NR1A/NR2B subtype NMDA receptors. They have good in vivo activity and some have a long half life in vivo. These compounds have relatively low activity at the alpha 1 receptor and therefore potentially have an enhanced side effect profile. In addition the compounds of Formula XVI have good water solubility which is advantageous for formulating an aqueous solution for iv administration.

Examples of compounds of Formula XVII include those having the Formula (XVIIa):

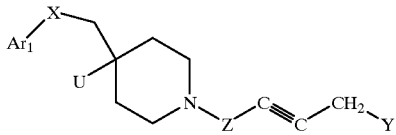

wherein $Ar_1$, X, U, Z and Y are as previously described for Formula XVII.

Certain of the compounds of the present invention are expected to be potent anticonvulsants in animal models and will prevent ischemia-induced nerve cell death in the gerbil global ischemia model after administration.

The compounds of the present invention are active in treating or preventing neuronal loss, neurodegenerative diseases, chronic pain, are active as anticonvulsants and inducing anesthesia. They are also useful for treating epilepsy and psychosis. The therapeutic and side effect profiles of subunit-selective NMDA receptor antagonists and agonists should be markedly different from the more non-selective types of inhibitors. The subtype-selective ligands of the present invention are expected to exhibit little or no untoward side effects caused by non-selective binding with other receptors, particularly, the PCP and glutamate binding sites associated with the NMDA receptor. In addition, selectivity for different NMDA receptor subtypes will reduce side effects such as sedation that are common to non-subtype-selective NMDA receptor antagonists. The compounds of the present invention are effective in treating or preventing the adverse consequences of the hyperactivity of the excitatory amino acids, e.g., those that are involved in the NMDA receptor system, by preventing the ligand-gated cation channels from opening and allowing excessive influx of $Ca^{++}$ into neurons, as occurs during ischemia.

Neurodegenerative diseases that may be treated with the compounds of the present invention include those selected from the group consisting of Alzheimer's disease, amyotrophic lateral sclerosis, Huntington's disease, Parkinson's disease and Down's syndrome.

The compounds of the present invention find particular utility in the treatment or prevention of neuronal loss associated with multiple strokes which give rise to dementia. After a patient has been diagnosed as suffering from a stroke, the compounds of the present invention may be administered to ameliorate the immediate ischemia and prevent further neuronal damage that may occur from recurrent strokes.

Moreover, the compounds of the present invention are able to cross the blood/brain barrier, which makes them particularly useful for treating or preventing conditions involving the central nervous system.

The compounds of the invention find particular utility in treating or preventing the adverse neurological consequences of surgery. For example, coronary bypass surgery requires the use of heart-lung machines, which tend to introduce air bubbles into the circulatory system that may lodge in the brain. The presence of such air bubbles robs neuronal tissue of oxygen, resulting in anoxia and ischemia. Pre- or post-surgical administration of the compounds of the present invention will treat or prevent the resulting ischemia. In a preferred embodiment, the compounds of the invention are administered to patients undergoing cardiopulmonary bypass surgery or carotid endarterectomy surgery.

The compounds of the present invention also find utility in treating or preventing chronic pain. Such chronic pain may be the result of surgery, trauma, headache, arthritis, pain from terminal cancer or degenerative diseases. The compounds of the present invention also find particular utility in the treatment of phantom pain that results from amputation of an extremity. In addition to treatment of pain, the compounds of the invention are also expected to be useful in inducing anesthesia, either general or local anesthesia, for example, during surgery.

The subunit-selective NMDA receptor antagonists, agonists and modulators may be tested for in vivo anticonvulsant activity after iv or ip injection using a number of anticonvulsant tests in mice (audiogenic seizure model in DBA-2 mice, pentylenetetrazol-induced seizures in mice, maximum electroshock seizure test (MES) or NMDA-induced death). The compounds may also be tested in drug discrimination tests in rats trained to discriminate PCP from saline. It is expected that most of the compounds of the present invention will not generalize to PCP at any dose. In addition, it is also expected that none of the compounds will produce a behavioral excitation in locomotor activity tests in the mouse. It is expected that such results will suggest that the subunit-selective NMDA receptor antagonists and agonists of the present invention do not show the PCP-like behavioral side effects that are common to NMDA channel blockers such as MK-801 and PCP or to competitive NMDA antagonists such as CGS 19755.

The subunit-selective NMDA receptor antagonists and agonists are also expected to show potent activity in vivo after intraperitoneal injection suggesting that these compounds can penetrate the blood/brain barrier.

Elevated levels of glutamate has been associated with glaucoma. In addition, it has been disclosed that glaucoma management, particularly protection of retinal ganglion cells, can be achieved by administering to a patient a compound capable of reducing glutamate-induced excitotoxicity in a concentration effective to reduce the excitotoxicity. See WO94/13275. Thus, the compounds of the present invention, which are expected to cross the blood-retina barrier, are also expected to be useful in the treatment of glaucoma. Preferably, the invention is directed to the treatment of patients which have primary open-angle glaucoma, chronic closed-angle glaucoma, pseudo doexfoliation, or other types of glaucoma or ocular hypertension. Preferably, the compound is administered over an extended period (e.g. at least six months and preferably at least one year), regardless of the changes in the patient's intraocular pressure over the period of administration.

The compounds of the present invention are also useful in treating CMV retinitis, particularly in combination with antiviral agents. CMV afflicts the ganglion cell layer which may result in higher levels of glutamate. Thus, NMDA receptor antagonists could block retinitis by blocking the toxicity effect of high level of glutamate.

Aminoglycoside antibiotics have been used successfully in the treatment of serious Gram-negative bacterial infections. However, prolonged treatment with these antibiotics will result in the destruction of sensory hearing cells of the inner ear and consequently, induce permanent loss of hearing. A recent study of Basile, et al. (Nature Medicine, 2: 1338–1344, 1996) indicated that aminoglycosides produce a polyamine-like enhancement of glutamate excitotoxicity through their interaction with the NMDA receptor. Thus, compounds of the present invention with NMDA receptor antagonist activity will be useful in preventing aminoglycoside antibiotics-induced hearing loss by antagonizing their interaction with the receptor.

The compounds of the present invention are useful in treating headaches, in particular, migraine headaches. During migraine attack, a sensory disturbance with unique changes of brain blood flow will result in the development of characteristic migraine auras. Since this unique phenomena has been replicated in animal experiments with cortical-spreading depression (CSD) of Leao, A.A.P.J., Neurophysiol. 7:359–390 (1944), CSD is considered an important phenomena in the pathophysiology of migraine with aura (Tepley et al., In: Biomagnetism, eds. S. Williamson, L. Kaufmann, pp. 327–330, Plenum Press, New York (1990)). The CSD is associated with the propagation (2~6 mm/s) of transient changes in electrical activity which relate to the failure of ion homoestatis in the brain, efflux of excitatory amino acids from the neurons and increased energy metabolism (Lauritzen, M., Acta Neurol. Scand. 76 (Suppl. 113) :4–40 (1987)). It has been demonstrated that the initiation of CSD in a variety of animals, including humans, involved the release of glutamate and could be triggered by NMDA (Curtis et al., Nature 191:1010–1011 (1961); and Lauritzen et al., Brain Res. 475:317–327 (1988)). Subtype selective NMDA antagonists will be therapeutically useful for migraine headache because of their expected low side effects, their ability to cross the blood brain barrier and their systemic bioavailability.

Bladder activity is controlled by parasympathetic preganglionic neurons in the sacral spinal cord (DeGroat et al., J. Auton. Nerv. Sys. 3:135–160(1981)). In humans, it has been shown that the highest density of NMDA receptors in the spinal cord are located at the sacral level, including those areas that putatively contain bladder parasympathetic preganglionic neurons (Shaw et al., Brain Research 539:164–168 (1991)). Because NMDA receptors are excitatory in nature, pharmacological blockade of these receptors would suppress bladder activity. It has been shown that the noncompetitive NMDA receptor antagonist MK801 increased the frequency of micturition in rat (Vera and Nadelhaft, Neuroscience Letters 134:135–138(1991)). In addition, competitive NMDA receptor antagonists have also been shown to produce a dose-dependent inhibition of bladder and of urethral sphincter activity (U.S. Pat. No. 5,192,751). Thus, it is anticipated that subtype-selective NMDA receptor antagonists will be effective in the treatment of urinary incontinence mediated by their modulation on the receptor channel activity.

Non-competitive NMDA receptor antagonist MK801 has been shown to be effective in a variety of animal models of anxiety which are highly predictive of human anxiety (Clineschmidt, B. V. et al., Drug Dev. Res. 2:147–163 (1982)). In addition, NMDA receptor glycine site antagonists are shown to be effective in the rat protentiated startle test (Anthony, E. W., Eur. J. Pharmacol. 250:317–324 (1993)) as well as several other animal anxiolytic models (Winslow, J. et al, Eur. J. Pharmacol. 190:11–22 (1990); Dunn, R. et al., Eur. J. Pharmacol. 214:207–214 (1992); and Kehne, J. H. et al, Eur. J. Pharmacol. 193:282–292 (1981)).

Glycine site antagonists, (+) HA-966 and 5,7-dichlorokynurenic acid were found to selectively antagonize d-amphetamine induced stimulation when injected into rat nucleus accumbens but not in striatum (Hutson, P. H. et al., Br. J. Pharmacol. 103:2037–2044 (1991)). Interestingly, (+) HA-966 was also found to block PCP and MK801-induced behavioral arousal (Bristow, L. J. et al., Br. J. Pharmacal, 108:1156–1163 (1993)). These findings suggest that a potential use of NMDA receptor channel modulators, but not channel blockers, as atypical neuroleptics.

It has been shown that in an animal model of Parkinson's disease—MPP$^+$or methamphetamine-induced damage to dopaminergic neurons—can be inhibited by NMDA receptor antagonists (Rojas et al., Drug Dev. Res. 29:222–226 (1993); and Sonsalla et al, Science 243;398–400 (1989)). In addition, NDMA receptor antagonists have been shown to inhibit haloperidol-induced catalepsy (Schmidt, W. J. et al., Amino Acids 1:225–237 (1991)), increase activity in rodents depleted of monoamines (Carlsson et al., Trends Neurosci. 13:272–276 (1990)) and increase ipsilateral rotation after unilateral substantia nigra lesion in rats (Snell, L. D. et al., J. Pharmacol. Exp. Ther. 235:50–57 (1985)). These are also experimental animal models of Parkinson's disease. In animal studies, the antiparkinsonian agent amantadine and memantine showed antiparkinsonian-like activity in animals at plasma levels leading to NMDA receptor antagonism (Danysz, W. et al., J. Neural Trans. 7:155–166, (1994)). Thus, it is possible that these antiparkinsonian agents act therapeutically through antagonism of an NMDA receptor. Therefore, the balance of NMDA receptor activity maybe important for the regulation of extrapyramidal function relating to the appearance of parkinsonian symptoms.

It is well known to use opiates, e.g., morphine, in the medical field to alleviate pain. (As used herein, the term "opiates" is intended to mean any preparation or derivative of opium, especially the alkaloids naturally contained therein, of which there are about twenty, e.g., morphine, noscapine, codeine, papaverine, and thebaine, and their derivatives.) Unfortunately, with continued use, the body builds up a tolerance for the opiate, and, thus, for continued relief, the patient must be subjected to progressively larger doses. Tolerance develops after both acute and chronic morphine administration (Kornetsky et al., Science 162:1011–1012 (1968); Way et al., J. Pharmacol. Exp Ther.

167:1–8 (1969); Huidobro et al., J. Pharmacol. Exp Ther. 198:318–329 (1976); Lutfy et al., J. Pharmacol. Exp Ther. 256:575–580 (1991)). This, in itself, can be detrimental to the patient's health. Furthermore, a time can come when the tolerance is substantially complete and the pain killing properties of the drug are no longer effective. Additionally, administration of higher doses of morphine may lead to respiratory depression, causing the patient to stop breathing. Seeking alternative drugs to produce analgesia without development of tolerance or as an adjunct therapy to block tolerance without interference with analgesia is an active area of research.

Recent studies have suggested a modulatory role for the NMDA receptor in morphine tolerance. (Trujillo et al., Science 251:85–87 (1991); Marek et al., Brain Res. 547:77–81 (1991); Tiseo et al., J. Pharmacol. Exp Ther. 264:1090–1096 (1993); Lutfy et al., Brain Res. 616:83–88 (1993); Herman et al., Neuropsychopharmacology 12:269–294 (1995).) Further, it has been reported that NMDA receptor antagonists are useful for inhibiting opioid tolerance and some of the symptoms of opioid withdrawal. Thus, the present invention is also directed to the administration of the compounds described herein to inhibit opiate tolerance and to treat or ameliorate the symptoms of opiate withdrawal by blocking the glycine co-agonist site associated with the NMDA receptor.

Thus, the present invention is directed to compounds having high binding to a particular NMDA receptor subunit and low binding to other sites such as dopamine and other catecholamine receptors, and σ sites. According to the present invention, those compounds having high binding to a particular NMDA subunit exhibit an $IC_{50}$ of about 100 $\mu$M or less in an NMDA subunit binding assay (see the Examples). Preferably, the compounds of the present invention exhibit an $IC_{50}$ of 10 $\mu$M or less. Most preferably, the compounds of the present invention exhibit an $IC_{50}$ of about 1.0 $\mu$M or less.

The efficacy of the NMDA subunit selective antagonists to inhibit glutamate neurotoxicity in rat brain cortex neuron cell culture system may be determined as follows. An excitotoxicity model modified after that developed by Choi (Choi, D. W., J. Neuroscience 7:357 (1987)) may be used to test anti-excitotoxic efficacy of the antagonists. Fetuses from rat embryonic day 19 are removed from time-mated pregnant rats. The brains are removed from the fetuses and the cerebral cortex is dissected. Cells from the dissected cortex are dissociated by a combination of mechanical agitation and enzymatic digestion according to the method of Landon and Robbins (Methods in Enzymology 124:412 (1986)). The dissociated cells are passed through an 80 micron nitex screen and the viability of the cells are assessed by Trypan Blue. The cells are plated on poly-D-lysine coated plates and incubated at 37° C. in an atmosphere containing 91% $O_2$/9% $CO2$. Six days later, fluoro-d-uracil is added for two days to suppress non-neural cell growth. At culture day 12, the primary neuron cultures are exposed to 100 $\mu$M glutamate for 5 minutes with or without increasing doses of antagonist or other drugs. After 5 minutes the cultures are washed and incubated for 24 hours at 37° C. Neuronal cell damage is quantitated by measuring lactate dehydrogenase (LDH) activity that is released into the culture medium. The LDH activity is measured according to the method of Decker et al. (Decker et al., J. Immunol. Methods 15:16 (1988)).

The anticonvulsant activity of the antagonists may be assessed in the audiogenic seizure model in DBA-2 mice as follows. DBA-2 mice may be obtained from Jackson Laboratories, Bar Harbor, Me. These mice at an age of <27 days develop a tonic seizure within 5–10 seconds and die when they are exposed to a sound of 14 kHz (sinus wave) at 110 dB (Lonsdale, D., Dev. Pharmacol. Ther. 4:28 (1982)). Seizure protection is defined when animals injected with drug 30 minutes prior to sound exposure do not develop a seizure and do not die during a 1 minute exposure to the sound. 21 day old DBA-2 mice are used for all experiments. Compounds are given intraperitoneally in either saline, DMSO or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The anticonvulsant efficacy of the antagonists may be assessed in the pentylenetetrazol (PTZ)-induced seizure test as follows. Swiss/Webster mice, when injected with 50 mg/kg PTZ (i.p.) develop a minimal clonic seizure of approximately 5 seconds in length within 5–15 minutes after drug injection. Anticonvulsant efficacy of an antagonist (or other) drug is defined as the absence of a seizure when a drug is given 30 minutes prior to PTZ application and a seizure does not develop for up to 45 minutes following PTZ administration. The antagonist or other drugs are given intraperitoneally in either saline, DMSO or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The efficacy of NMDA antagonists to protect mice from NMDA induced death may be assessed as follows. When mice are injected with 200 mg/kg N-methyl-D-aspartate (NMDA) i.p., the animals will develop seizures followed by death within 5–10 minutes. The antagonists are tested for their ability to prevent NMDA-induced death by giving the drugs i.p. 30 minutes prior to the NMDA application. The antagonist or other drugs are given intraperitoneally in either saline, DMSO or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The series of different evaluations may be conducted on doses of the NMDA antagonists of the invention to determine the biological activity of the compounds both in normal gerbils and in animals exposed to 5 minutes of bilateral carotid occlusion. See Scheme 24.

Scheme 24
Gerbil Ischemia Model

Locomotor Behavior Test

1. Surgery to Expose Carotid Arteries
2. Recovery for 48 h
3. Carotid Artery Occlusion
    (5 minutes, non-anesthetized animals)

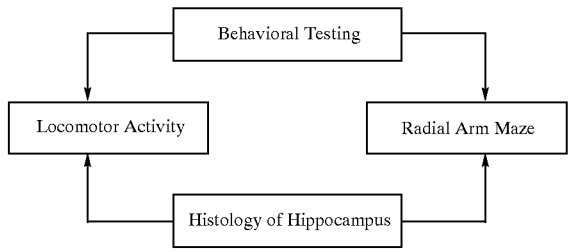

These studies are conducted in animals who are conscious and have no other pharmacological agents administered to them. Gerbils are preinstrumented 48-hours prior to ischemia to allow for the complete elimination of the pentobarbital anesthetic which is employed. When tested with drugs, animals are given IP injections of the NMDA antagonist or vehicle. In the case of multiple injections, animals are given IP injections 2 hours apart and the final injection is given 30 minutes prior to the ischemic period or in the case of post treatment, the animals are given injections at 30 minutes, 2 hours, 4 hours and 6 hours post-ischemic reperfusion.

In order to assess the direct pharmacological activity or potential activity of the NMDA antagonists, naive gerbils are injected with either saline or differing doses of the antagonist. The behavioral changes are assessed using a photobeam locomotor activity chamber which is a two foot circular diameter arena with photobeam detection. Animals are individually placed in the 2 foot diameter chambers. The chambers are housed in a cabinet which is closed and noise is abated using both a background white noise generator and a fan. Animals are placed in these chambers in the case of the initial pharmacological evaluation for a period of 6 hours and the total activity during each successive hour is accumulated using the computer control systems.

Saline results in an initial high rate of activity, with the control animals showing a first hour activity level of about 1600 counts. This level of control activity is typical for the gerbil under these experimental conditions. As the session progressed, animals decrease their exploratory activity and at the terminal period the activity declines to about 250 counts per hour. It is expected that the NMDA antagonists of the present invention will have no significant effect on either the initial exploratory rate or the terminal rate of exploration.

In a next phase of the evaluation of the NMDA antagonists, gerbils are pretreated with varying doses of the antagonists and then exposed to a five minute period of bilateral carotid occlusion. Following the initiation of reperfusion, animals are placed into the circular locomotor activity testing apparatus and the activity at the beginning of the first hour following reperfusion is monitored for the subsequent four hours.

Control animals not exposed to ischemia and given injections of saline prior to being placed in the locomotor activity chamber show a characteristic pattern of activity which in the first hour of locomotor activity is substantially higher than during all other hours and progressively declined over the four hours to a very low value. In contrast to the progressive decline in activity over the four hour testing period, control animals that are exposed to five minutes of cortical ischemia demonstrate a completely different pattern of locomotor activity. During the first hour there is a significant decline in activity, which is followed by a progressive increase in which the activity during the fourth hour is ten-fold higher than that demonstrated by animals not exposed to carotid occlusion. These results are typical and are a reliable result of the alterations caused by five minutes of bilateral carotid occlusion in the gerbil.

Separate groups of gerbils are pretreated with the NMDA antagonists of the invention 30 minutes before the onset of carotid occlusion and then placed into the locomotor activity following one hour of reperfusion. It is expected that pretreatment of the gerbils with the NMDA antagonists of the invention will prevent both the post-ischemic decrease and increase in activity. Post-ischemic decreases in activity are expected to be near zero during the first hour following reperfusion. Pretreatment with the NMDA antagonists of the invention is expected to reduce or prevent this early depression of behavior. In addition, the NMDA antagonists of the invention are expected to prevent the post-ischemic stimulation of behavior. Subsequent to completion of the single dose pretreatment evaluations, gerbils are also evaluated with multiple injections of the NMDA antagonists of the invention. Doses are administered I.P. at 6 hours, 4 hours, 2 hours and 30 minutes prior to the onset of 5 minutes of ischemia.

At 24 hours all animals are evaluated for differences in patrolling behavior using a 8-arm radial maze. In this procedure, animals are placed into the center start chamber of the maze, the barrier removed and the amount of time and the number of times the animal makes an error recorded prior to completion of exploration in all 8 arms of the maze. An error is defined as the revisiting of an arm by entering to the extent of the entire body without including tail by the animal. If the animal perseveres or fails to leave the arm for longer than five minutes, the session is terminated. In the control population of the animals, the number of errors and exploration of the maze with no prior experience (naive) is approximately 6 errors. This is an average value for an N of 28 gerbils. Following 5 minutes of bilateral carotid occlusion and testing at 24 hours, gerbils make an average number of errors of 21. When animals are pretreated with the NMDA antagonists of the invention, there is expected to be a significant reduction in the number of errors made.

There is also expected to be a significant sparing of the behavioral changes that are induced in the radial arm maze performance.

It is also expected that post treatment with the NMDA antagonists of the invention will reduce the short term memory impairment 24 hours post ischemic/reperfusion.

The effects of 5 minutes of bilateral carotid occlusion on neuronal cell death in the dorsal hippocampus may be evaluated in animals 7 days after ischemia reperfusion injury. Previous studies have demonstrated that neuronal degeneration begins to occur around 3 days following cerebral ischemia. By 7 days, those neurons that have been affected will undergo cytolysis and have either completed degeneration or are readily apparent as dark nuclei and displaced nuclei or as cells with eosinophilic cytoplasm and pycnotic nuclei. The lesion with 5 minutes of ischemia is essentially restricted within the hippocampus to the CA1 region of the dorsal hippocampus. The intermedial lateral zone of the horn is unaffected and the dentate gyrus and/or in CA3 do not show pathology. Gerbils are anesthetized on day 7 following ischemia with 60 mg/kg of pentobarbital. Brains are perfused transcardiac with ice-cold saline followed by buffered paraformaldehyde (10%). Brains are removed, imbedded and sections made. Sections are stained with hematoxylin-eosin and neuronal cell counts are determined in terms of number of neuronal nuclei/100 micrometers. Normal control animals (not exposed to ischemia reperfusion injury) will not demonstrate any significant change in normal density nuclei within this region. Exposure to five minutes of bilateral carotid occlusion results in a significant reduction in the number of nuclei present in the CA1 region. In general, this lesion results in a patchy necrosis instead of a confluent necrosis, which is seen if 10 minutes of ischemia is employed. Pretreatment with the NMDA antagonists of the invention are expected to produce a significant protection of hippocampal neuronal degeneration.

It is known that NMDA receptors are critically involved in the development of persistent pain following nerve and tissue injury. Tissue injury such as that caused by injecting a small amount of formalin subcutaneously into the hindpaw of a test animal has been shown to produce an immediate increase of glutamate and aspartate in the spinal cord (Skilling, S. R., et al., *J. Neurosci.* 10:1309–1318 (1990)). Administration of NMDA receptor blockers reduces the response of spinal cord dorsal horn neurons following formalin injection (Dickenson and Aydar, *Neuroscience Lett.* 121:263–266 (1991); Haley, J. E., et al., *Brain Res.* 518:218–226 (1990)). These dorsal horn neurons are critical in carrying the pain signal from the spinal cord to the brain and a reduced response of these neurons is indicative of a reduction in pain perceived by the test animal to which pain has been inflicted by subcutaneous formalin injection.

Because of the observation that NMDA receptor antagonists can block dorsal horn neuron response induced by subcutaneous formalin injection, NMDA receptor antagonists have potential for the treatment of chronic pain such as pain that is caused by surgery or by amputation (phantom pain) or by infliction of other wounds (wound pain). However, the use of conventional NMDA antagonists such as MK-801 or CGS 19755, in preventing or treating chronic pain, is severely limited by the adverse PCP-like behavioral side effects that are caused by these drugs. It is expected that the NMDA receptor antagonists that are the subject of this invention will be highly effective in preventing chronic pain in mice induced by injecting formalin subcutaneously into the hindpaw of the animals. Because the NMDA receptor antagonists of this invention are expected to be free of PCP-like side effects, these drugs are highly useful in preventing or treating chronic pain without causing PCP-like adverse behavioral side effects.

The effects of the NMDA receptor antagonists of the present invention on chronic pain may be evaluated as follows. Male Swiss/Webster mice weighing 25–35 grams are housed five to a cage with free access to food and water and are maintained on a 12 hour light cycle (light onset at 0800 h). The NMDA receptor antagonist is dissolved in DMSO at a concentration of 1–40 and 5–40 mg/mL, respectively. DMSO is used as vehicle control. All drugs are injected intraperitoneally (1 $\mu$L/g). The formalin test is performed as described (Dubuisson and Dennis, Pain 4:H161–174 (1977)). Mice are observed in a plexiglass cylinder, 25 cm in diameter and 30 cm in height. The plantar surface of one hindpaw is injected subcutaneously with 20 $\mu$L of 5% formalin. The degree of pain is determined by measuring the amount of time the animal spends licking the formalin-injected paw during the following time intervals: 0–5' (early phase); 5'–10', 10'–15' and 15'–50' (late phase). To test whether the NMDA receptor antagonists prevent chronic pain in the test animals, vehicle (DMSO) or drugs dissolved in vehicle at doses of 1 mg/kg to 40mg/kg are injected intraperitoneally 30 minutes prior to the formalin injection. For each dose of drug or vehicle control at least six animals are used.

Compared to vehicle control, it is expected that the intraperitoneal injection of the NMDA receptor antagonists 30 minutes prior to formalin injection into the hindpaw will significantly inhibit formalin-induced chronic pain in a dose-dependent manner as determined by the reduction of the time spent licking by the mouse of the formalin injected hindpaw caused by increasing doses of NMDA receptor antagonist.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g., humans, orally at a dose of 0.0025 to 50 mg/kg, or an equivalent amount of the pharmaceutically acceptable salt thereof, per day of the body weight of the mammal being treated for anxiety disorders, e.g., generalized anxiety disorder, phobic disorders, obsessional compulsive disorder, panic disorder, and post traumatic stress disorders or for schizophrenia or other psychoses. Preferably, about 0.01 to about 10 mg/kg is orally administered to treat or prevent such disorders. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in ischemia, brain and spinal cord trauma, hypoxia, hypoglycemia, and surgery, to treat or prevent glaucoma or urinary incontinence, as well as for the treatment of Alzheimer's disease, amyotrophic lateral sclerosis, Huntington's disease, Parkinson's disease and Down's Syndrome, or in a method of treating a disease in which the pathophysiology of the disorder involves hyperactivity of the excitatory amino acids or NMDA receptor-ion channel related neurotoxicity, the pharmaceutical compositions of the invention may comprise the compounds of the present invention at a unit dose level of about 0.01 to about 50 mg/kg of body weight, or an equivalent amount of the pharmaceutically acceptable salt thereof, on a regimen of 1–4 times per day. When used to treat chronic pain, migrain headache, to induce anesthesia, to treat or prevent opiate tolerance or to treat opiate withdrawal, the compounds of the invention may be administered at a unit dosage level of from about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations that can be used pharmaceutically. Preferably, the preparations, particularly those preparations that can be administered orally and that can be used for the preferred type of administration, such as tablets, dragees, and capsules, and also preparations that can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular NMDA subunit selective antagonist or agonist of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular haloperidol analog of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner that is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as, acetyl-cellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations that can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules that consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances that increase the viscosity of the suspension include, for example, sodium carboxymethyl cellulose, sorbitol, and/or dextran. Optionally, the suspension may also contain stabilizers.

The characterization of NMDA subunit binding sites in vitro has been difficult because of the lack of selective drug ligands. Thus, the NMDA ligands of the present invention may be used to characterize the NMDA subunits and their distribution. Particularly preferred NMDA subunit selective antagonists and agonists of the present invention that may be used for this purpose are isotopically radiolabelled derivatives, e.g., where one or more of the atoms are replaced with $^3H$, $^{11}C$, $^{14}C$, $^{15}N$, or $^{18}F$. Alternatively, a fluorescent group Y may be employed. Examples of such groups include 4-nitrobenzofurazan:

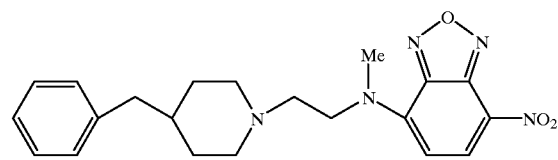

The following examples are illustrative, but not limiting, of the method and compositions of the present invention. Other suitable modifications and adaptations of the variety of conditions and parameters normally encountered in clinical therapy and that are obvious to those skilled in the art are within the spirit and scope of the invention.

EXAMPLE 1

Preparation of N-(Methoxycarbonylbutyl)-4-benzylpiperidine

A mixture of methyl bromovalerate (1.56 g, 8.0 mmol), 4-benzylpiperidine (1.49 g, 8.5 mmol) and potassium carbonate (2.93 g, 21.25 mmol) in 30 mL of acetonitrile was refluxed under $N_2$ for 12 hr. The inorganic salt was removed through a short column of silica gel and washed with ethyl acetate (3×30 mL). The filtrate was evaporated in vacuo to give a residue, which was purified by flash chromatography, giving 1.8 g (78%) of the product as a pale yellow oil. $^1$H NMR (CHCl$_3$), 1.312 (m, 2 H), 1.505–1.593 (m, 7 H), 1.831 (m, 2 H), 2.292 (m, 4 H), 2.505 (d, J=6.9 Hz, 2 H), 2.860 (d, J=11.4 Hz, 2 H), 3.647 (s, 3 H), 7.136 (m, 5 H).

EXAMPLE 2

Preparation of 4-Benzylpiperidylpentamide

To a solution of N-(methoxycarbonylbutyl)-4-benzylpiperidine (289 mg, 1.0 mmol) in 5 mL of methanol was added 5 mL of 30% ammonium hydroxide solution at room temperature. The resulting solution was allowed to stir at rt overnight. The solvent was evaporated in vacuo to give a residue. Water (5 mL) was added into the residue, which was extracted with ethyl acetate (3×10 mL) and dried over sodium sulfate. The solvent was evaporated in vacuo to give a residue, which was purified by flash chromatography, giving 120 mg (44%) of the product as off-white solid. mp 95–96° C. $^1$H NMR (CHCl$_3$) 1.285 (m, 2 H), 1.537–1.595 (m, 7 H), 1.835 (m, 2 H), 2.212 (m, 2 H), 2.274 (m, 2 H), 2.495 (d, J=6.9 Hz, 2 H), 2.853 (d, J=9.9 Hz, 2 H), 5.942 (s, 2 H), 7.104–7.228 (m, 5 H).

EXAMPLE 3

Preparation of 4-Benzylpiperidylpentahydrazide

To a solution of N-(methoxycarbonylbutyl)-4-benzylpiperidine (289 mg, 1.0 mmol) in 5 mL of methanol was added 3 mL of $NH_2NH_2$ at room temperature. The resulting solution was allowed to stir at rt overnight. The solvent was evaporated in vacuo to give a residue. Water (5 mL) was added into the residue, which was extracted with ethyl acetate (3×10 mL) and dried over sodium sulfate. The solvent was evaporated in vacuo to give a residue, which was purified by flash chromatography, giving 217 mg (75%) of the product as off-white solid. mp 104–106° C. $^1$H NMR (CHCl$_3$) 1.324 (m, 2 H), 1.506–1.655 (m, 7 H), 1.839 (m, 2 H), 2.189 (m, 2 H), 2.291 (m, 2 H), 2.521 (d, J=6.9 Hz, 2 H), 2.853 (d, J=11.4 Hz, 2 H), 3.857 (s, 2 H), 7.104–7.228 (m, 6 H).

EXAMPLE 4

N-(5-(4-Benzylpiperidin-1-yl)valeroyl)-N'-(4-nitrobenzoyl)hydrazine

To a solution of 5-(4-benzylpiperidin-1-yl)valerhydrazide (289 mg, 1.00 mmol) in 10 mL of $CH_2Cl_2$ and 0.21 mL of $Et_3N$ was added 4-nitrobenzoyl chloride (278 mg, 1.50 mmol). The resulting solution was allowed to stir at rt for 12 hr. The mixture was poured into ice water (10 g). The organic layer was separated and the water phase was extracted with $CH_2Cl_2$ (2×15 mL). The combined organic extracts were dried over $Na_2SO_4$. Evaporation of solvent gave the title product as a brown oil (405 mg, 92%): $^1$H NMR (CDCl$_3$) 1.25 (m, 2 H), 1.60 (m, 6 H), 1.90 (m, 2 H), 2.29 (m, 4 H), 2.48 (d, J=6.6 Hz, 2 H), 2.90 (m, 2 H), 3.42 (s, 1 H), 7.07–7.24 (m 5 H), 7.70 (bs, 2 H), 7.96 (d, J=7.8 Hz, 2 H), 8.08 (d, J=7.8 Hz, 2 H).

EXAMPLE 5

N-(4-Aminobenzoyl)-N'-(5-(4-benzylpiperidin-1-yl)valeroyl)hydrazine

To a solution of N-(5-(4-benzylpiperidin-1-yl)valeroyl)-N'-(4-nitrobenzoyl)hydrazine (200 mg, 0.456 mmol) in 20 mL of methanol was added 50 mg of 5% Pd/C. The resulting mixture was hydrogenated at 30 psi of hydrogen for 3 hr. The catalyst was removed through a short column of Celite and was washed with methanol (15 mL). The extracts were evaporated in vacuo to give an oil, which was purified by flash chromatography to give the title product as a solid (60 mg, 32%):. mp 163–165° C.; $^1$H NMR (CDCl$_3$) 1.26 (m, 2 H), 1.59 (m, 9 H), 1.92 (m, 2 H), 2.28 (m, 4 H), 2.52 (m, 2 H), 2.90 (m, 2 H), 3.29 (s, 2 H), 6.83 (d, J=8.1 Hz, 2 H), 7.10 (m, 3 H), 7.20 (m, 2 H), 7.63 (d, J=7.8 Hz, 2 H).

EXAMPLE 6

Preparation of 4-benzyl-1-(3-Butynyl)piperidine

A mixutre of 3-butyn-1-methanesulfate (3.032 g, 0.02 mol), 4-phenylpiperidine (4.21 g, 0.024 mol) and potassium carbonate (8.28 g, 0.06 mol) in 50 mL of acetonitrile was refluxed for 12 hrs. The mixutre was filtered and washed with ethyl acetate (3×30 mL). The filtrate was evaporated in vacuo and was purified by flash chromatography to give 4.30 g (95%) of the product as pale yellow oil. $^1$H NMR (CHCl$_3$) 1.319 (m, 2 H), 1.51 (m, 1 H), 1.652 (m, 2 H), 1.937 (m, 3 H), 2.364 (m, 2 H), 2.543 (m, 4 H), 2.858 (d, J=11.4 Hz, 2 H), 7.121–7.270 (m, 5 H).

EXAMPLE 7

Preparation of 1-(3-Butynyl)-4-(p-chlorphenyl)-4-hydroxypiperidine

A mixutre of 3-butyn-1-methanesulfate (1.48 g, 0.01 mol), 4-(p-chlorophenyl)-4-hydroxypiperidine (2.54 g, 0.012 mol) and potassium carbonate (4.14 g, 0.03 mol) in 25 mL of acetonitrile was refluxed for 12 hrs. The mixture was filtered and washed with ethyl acetate (3×30 mL). The filtrate was evaporated in vacuo and was purified by flash chromatography to give 2.30 g (87%) of the product as a white solid. mp 98–100° C. $^1$H NMR (CHCl$_3$) 1.550 (s, 1 H), 1.749 (m, 2 H), 1.997 (m, 1 H), 2.109 (m, 2 H), 2.423 (m, 4 H), 2.655 (m, 2 H), 2.798 (m, 2 H), 7.329 (d, J=7.2 Hz, 2 H), 7.429 (d, J=7.2 Hz, 2 H).

EXAMPLE 8

Preparation of m-Fluorobenzyltriphenylphosphonium bromide

To a solution of triphenylphosphine (45.24 g, 0.12 mol) in 200 mL of ether was added 3-fluorobenzyl bromide (22.7 g, 0.12 mol). The resulting solution was allowed to stir at rt overnight. The white solid was collected by filtration and dried to give 58.0 g (85%) of the product as a white solid. mp 290–292° C. $^1$H NMR (CHCl$_3$) 5.516 (d, J=14.7 Hz, 2 H), 6.725 (d, J=9.6 Hz, 1 H), 6.893 (m, 2 H), 7.084 (m, 2 H), 7.622–7.762 (m, 15 H).

EXAMPLE 9

Preparation of 1-Benzyl-4-(m-fluorobenzylidene)piperidine

To a suspension of m-fluorobenzyltriphenylphosphonium bromide (16.98 g, 0.03 mol) in 50 mL of THF was added 14.5 mL of BuLi (M=2.5 M) at −78° C. under $N_2$. After stirring at −78° C. for 45 min., a solution of 4-benzylpiperidone (5.67 g, 0.03 mol) in 10 mL of THF was added dropwise at −78° C. under $N_2$. The resulting mixture was allowed to warm to room temperature and stirred for another 5 hr. Then the mixture was poured into ice (100 g)

and extracted with ether (3×40 mL). The combined extracts were dried over sodium sulfate. The solvent was evaporated in vacuo to give a residue, which was purified by flash chromatography, giving 0.6 g (7%) of the product as pale yellow oil. $^1$H NMR (CHCl$_3$) 2.413 (m, 2 H), 2.466 (m, 2 H), 2.558 (m, 4 H), 3.558 (s, 2 H), 6.257 (s, 1 H), 6.905 (m, 3 H), 7.284 (m, 6 H).

EXAMPLE 10

Preparation of 4-[N-IDDC (±)]-4'-fluorobutyrophenone

A solution of 88 mg (0.398 mmol) of IDDC (±), 142 mg (0.707 mmol) of 4-chloro-4'-fluorobutyrophenone and 100 mg (0.99 mmol) of Et$_3$N in 4 mL of DMF was heated at 75° C. for 48 h. It was cooled to room temperature and added into 10 mL of water and the mixture was extracted by CHCl$_3$ (2×6 mL). The extract was washed by water (2 ×5 mL), dried and evaporated to leave liquid, which was treated with 2 mL of water. The oily precipitate was separated by preparative TLC (ethyl acetate:hexane=25:30, R$_f$=0.72–0.58) to give 85 mg (55%) of almost colorless oil. $^1$H NMR (CDCl$_3$), 1.94 (m, 2), 2.6 (m, 1), 2.7 (m, 1), 2.88–3.02 (m, 4), 3.40–3.62 (m, 2), 3.81 (d, 1), 3.975 (t, 1), 6.96–7.20 (m, 10), 7.90 (m, 2).

EXAMPLE 11

Preparation of 4-(N-MK801)-4'-fluorobutyrophenone

A solution of 102 mg (0.396 mmol) of MK801 HCl, 76 mg (0.38 mmol) of 4-chloro-4'-fluorobutyrophenone, 80 mg (0.79 mmol) of Et$_3$N and 10 mg of NaI in 2 mL of DMF was heated at 80° C. for 3 days. It was cooled to room temperature and added into 10 mL of water and the mixture was extracted by CHCl$_3$ (3×10 mL). The extract was washed by water (5×10 mL), dried and evaporated to leave liquid which was separated by preparative TLC (ethyl acetate:hexane= 1:1, R$_f$=0.70-0.59) to give 45 mg (30%) of pale-yellow oil. $^1$H NMR (CDCl$_3$), 1.792 (s, 3), 2.075 (m, 2), 2.488 (d, 1), 2.50–2.66 (m, 4), 2.99 (m, 1), 3.097 (m, 1), 3.350 (dd, 1), 4.545 (d, 1), 6.903 (m, 1), 7.00–7.14 (m, 7), 7.217 (m, 1), 7.308 (m, 1), 7.912 (m, 2).

EXAMPLE 12

Preparation of 4-(4-Benzylpiperidinyl)-4'-fluorobenzophenone and 4,4'-Bis(4-benzylpiperidinyl)benzophenone.

A solution of 299 mg (1.37 mmol) of 4,4'-difluorobenzophenone and 486 mg (2.77 mmol) of 4-benzylpiperidine in 2 mL of anhydrous DMF was heated at 150° C. for 24 h. It was cooled to room temperature, diluted by 10 mL of ethyl acetate and washed by brine (3×10 mL) and water (1×10 mL). The solution was dried and evaporated. The residue was separated by chromatography (silica gel), eluted by hexane:ethyl acetate=10:1 to give 180 mg of 25 as white solid. $^1$H NMR (CDCl$_3$), 1.20–1.40 (m, 3), 1.77 (d, 2), 2.583 (d, 2), 2.840 (t, 2), 3.909 (d, 2), 6.872 (d, 2), 7.10–7.30 (m, 7), 7.75 (m, 4). Another fraction gave 50 mg of 26 as white solid. $^1$H NMR (CDCl$_3$), 1.39 (m, 6), 1.759 (d, 4), 2.582 (d, 4), 2.803 (t, 4), 3.871 (d, 4), 6.877 (d, 4), 7.154–7.302 (m, 10), 7.728 (d, 4). MS, 528 (M+, 100), 436 (20). HRMS, Calcd for C$_{37}$H$_{40}$N$_2$O 528.3129, Found 528.3127.

EXAMPLE 13

Preparation of 4-(4-Hydroxypiperidinyl) butyrophenone

A mixture of 4-hydroxypiperidine (550 mg, 5.4 mmol), 4-chlorobutyrophenone (490 mg, 2.7 mmol), NaI (160 mg), K$_2$CO$_3$ (760 mg) and toluene (25 mL) was refluxed for 24 h, cooled to rt, filtered and washed with hexane (2×10 mL). The filtrate was evaporated, and the residue was chromatographed over silica gel (EtOAc-EtOH-NH$_4$OH, 60:40:2) to give 21 mg (3%) of the free base as a yellow powder, mp 101–2° C. $^1$H NMR (CDCl$_3$-D$_2$O): 1.50–1.57 (m, 2H), 1.83–1.98 (m, 3H), 2.08–2.17 (m, 3H), 2.397 (t, 2H, J=7), 2.73–2.78 (m, 2H), 3.00 (t, 2H, J=7), 3.60–3.70 (m, 1H), 7.43–7.56 (m, 3H), 7.96–7.98 (m, 2H). Analysis, Calcd for C$_{15}$H$_{21}$NO$_2$: C 72.84, H 8.56, N 5.66; Found: C 72.31, H 8.45, N 5.32.

EXAMPLE 14

Preparation of 4-Benzyl-4-hydroxy-1-(2-phenylethyl)piperidine and the hydrochloride From 2-phenylethyl bromide (702 mg, 3.8 mmol), 4-benzyl-4-hydroxypiperidine (1.51g, 7.9 mmol) and NaI (50 mg) in toluene (20 mL) was obtained 960 mg (83.6%) of the free base as a yellow viscous oil. $^1$H NMR (CDCl$_3$): 1.20–1.27 (m, 1H), 1.54–1.60 (m, 4H), 1.75–1.85 (m, 2H), 2.35–2.42 (m, 2H), 2.60–2.65 (m, 2H), 2.78–2.85 (m, 4H), 7.19–7.34 (m, 10H). The hydrochloride mp 233–5° C. Analysis, Calcd. for C$_{20}$H$_{26}$ClNO: C 72.38, H 7.90, N 4.22; Found: C 72.06, H 7.90, N 3.97.

EXAMPLE 15

Preparation of 1-(2-Phenylethyl)-4-benzylidenepiperidine and the hydrochloride

A suspension of 4-benzyl-4-hydroxy-1-(2-phenylethyl) piperidine hydrochloride (400 mg, 1.28 mmol) in 20 mL of 40% (w/w) aq H$_2$SO$_4$ was refluxed for 16 h, then cooled in an ice-water bath and basified to pH 10 with 1N aq NaOH. The resulting mixture was extracted with CH$_2$Cl$_2$ (3×10 mL). The extracts were combined, washed with brine (10 mL), dried (MgSO$_4$) and evaporated. The residue was chromatographed over silica gel (EtOAc-EtOH, 10:0.5) to give 180 mg (50%) of the free base as a yellow viscous oil. $^1$H NMR (CDCl$_3$): 2.04–2.18 (m, 2H), 2.56–2.68 (m, 4H), 2.82–2.87 (m, 2H), 3.066 (bs, 2H), 3.307 (bs, 2H), 5.400 (bs, 1H), 7.17–7.31 (m, 10H). The hydrochloride, mp 193° C. $^1$H NMR (D$_2$O): 2.15–2.32 (m, 2H), 3.042 (t, 2H, J=7.5), 3.10–3.88 (m, 8H), 5.483 (s, 1H), 7.23–7.39 (m, 10H). Analysis, Calcd. for C$_{20}$H$_{24}$ClN0.2H$_2$O: C 75.66, H 7.75, N 4.41; Found: C 75.73, H 7.60, N 4.22.

EXAMPLE 16

Preparation of 4-Benzyl-4-hydroxy-1-(3-phenylpropyl)piperidine and the hydrochloride From 1-bromo-3-phenylpropane (598 mg, 3.0 mmol), 4-benzyl-4-hydroxypiperidine (1.15 g, 6.0 mmol) and NaI (150 mg, 1.0 mmol) in toluene (20 mL) was obtained 780 mg (84%) of the free base as a yellow viscous oil. $^1$H NMR (CDCl$_3$): 1.183 (s, 1H, OH), 1.50–1.54 (m, 2H), 1.71–1.89 (m, 4H), 2.24–2.32 (m, 2H), 2.397 (t, 2H, J=8), 2.60–2.70 (m, 4H), 2.755 (s, 2H), 7.12–7.34 (m, 10H). The hydrochloride, mp 156–7° C. Analysis, Calcd. for C$_{21}$H$_{28}$ClNO: C 72.92, H 7.87, N 4.05; Found: C 73.07, H 8.10, N 4.13.

EXAMPLE 17

Preparation of 4-Benzylidene-1-(3-phenylpropyl) piperidine and the hydrochloride A mixture of 4-benzyl-4-hydroxy-1-(3-phenylpropyl) piperidine hydrochloride (320 mg, 0.92 mmol) in 15 mL of 40% (w/w) aq $H_2SO_4$ was refluxed for 3 days, then cooled in an ice-water bath and basified to pH 10 with 1N aq NaOH. The resulting mixture was extracted with $CH_2Cl_2$ (3×10 mL), and the extract was washed with brine (10 mL), dried ($MgSO_4$) and evaporated.

The residue was chromatographed over silica gel (EtOAc-EtOH, 10:1) to give 120 mg (44%) of the free base as a yellow viscous oil. $^1H$ NMR ($CDCl_3$): 1.80–1.85 (m, 2H), 2.064 (bs 2H), 2.427 (t, 2H, J=7), 2.517 (t, 2H, J=7.5), 2.642 (t, 2H, J=7.5), 2.963 (bs, 2H), 3.288 (bs, 2H), 5.370 (bs, 1H), 7.17–7.31 (m, 10H). The hydrochloride, mp 156–7° C. Analysis, Calcd. for $C_{21}H_{26}ClN$: C 76.92, H 7.99, N 4.27; Found: C 76.79, H 8.02, N 4.30.

EXAMPLE 18

Preparation of N-(2-Phenoxyethyl)-1,2,3,4-tetrahydroisoquinoline and the hydrochloride From 1,2,3,4-tetrahydroisoquinoline (1.077 g, 8.1 mmol), 3-phenoxypropyl bromide (806 mg, 4.0 mmol) and NaI (40 mg) in toluene (15 mL) was obtained 990 mg (89%) of the free base as a yellow viscous oil. $^1H$ NMR ($CDCl_3$): 2.88–2.96 (m, 2H), 3.012 (t, 2H, J=6), 3.806 (s, 2H), 4.223 (t, 2H, J=6), 4.171 (t, 2H, J=5.7), 6.92–7.32 (m, 9H). The hydrochloride, mp 181–2° C. Analysis, Calcd. for $C_{17}H_{20}ClNO$: C 70.46, H 6.96, N 4.83; Found: C 70.29, H 7.02, N 4.80.

EXAMPLE 19

Preparation of N-(3-Phenoxypropyl)-1,2,3,4-tetrahydroisoquinoline and the hydrochloride From 1,2,3,4-tetrahydroisoquinoline (1.077 mg, 8.1 mmol), 3-phenoxypropyl bromide (863 mg, 4.0 mmol) and NaI (36 mg) in toluene (15 mL) was obtained 990 mg (89%) of the free base as a yellow viscous oil. $^1H$ NMR ($CDCl_3$): 2.04–2.19 (m, 2H), 2.720 (t, 2H, J=7), 2.760 (t, 2H, J=7), 2.925 (t, 2H, J=7), 3.678 (bs, 2H), 4.072 (t, 2H, J=7), 6.89–7.30 (m, 9H). The hydrochloride, mp 194–5° C. Analysis, Calcd. for $C_{18}H_{22}ClNO$: C 71.16, H 7.30, N 4.61; Found: C 71.01, H 7.41, N 4.41.

EXAMPLE 20

N-[(3-(4-Fluorobenzoylpropyl)]-1,2,3,4-tetrahydroisoquinoline

From 1,2,3,4-tetrahydroisoquinoline (530 mg, 4.0 mmol) and 4-chloro-4'-fluorobutyro-phenone (402 mg, 2.0 mmol) there was obtained 190 mg (30%) of the title compound as a viscous yellow oil. $^1H$ NMR ($CDCl_3$): 2.00–2.09 (m, 2H), 2.595 (t, 2H, J=7), 2.71–2.75 (m, 2H), 2.86–2.90 (m, 2H), 3.055 (t, 2H, J=7), 3.622 (s, 2H), 7.00–7.12 (m, 6H), 7.988 (dd, 2H, J=8.5; 5.5). The hydrochloride, mp 213–5° C. Anal, Calcd. for ($C_{19}H_{20}FNO$ +HCl): C 68.36, H 6.34, N 4.30; Found: C 68.09, H 6.31, N 4.16.

EXAMPLE 21

6,7-Dimethoxy-2-(3-phenoxypropyl)-1,2,3,4-tetyrahydroisoquinoline

From 3-phenoxypropyl bromide (212 mg, 0.98 mmol) and 6,7-dimethoxyl-1,2,3,4-tetrahydroisoquinoline (380 mg, 1.96 mmol) there was obtained 160 mg (45%) of the title compound as a yellowish viscous oil. $^1H$ NMR ($CDCl_3$): 2.03–2.12 (m, 2H), 2.67–2.76 (m, 4H), 2.81–2.83 (m, 2H), 3.584 (s, 2H), 3.834 (s, 3H), 3.842 (s, 3H), 4.068 (t, 2H, J=6), 6.524 (s, 1H), 6.596 (s, 1H), 6.90–6.95 (m, 3H), 7.25–7.30 (m, 2H). The hydrochloride, mp 193–5° C. Anal. Calcd. for ($C_{20}H_{24}NO_3$ +HCl): C, 66.20, H 6.94, N 3.86; Found: C 65.88, H 6.87, N 3.81.

EXAMPLE 22

2-N-[3-(4-Fluorobenzoyl)propyl]-1,2,3,4-tetrahydropyrido[3,4-b]indole

From 1,2,3,4-tetrahydro-9H-pyrido[3,4-b]indole (276 mg, 1.6 mmol) and 4-chloro-4-fluorobutyrophenone (301 mg, 1.5 mmol) there was obtained 59 mg (22%) of the title compound as a yellow powder, mp 188–190° C. $^1H$ NMR ($CDCl_3$): 2.01–2.11 (m, 2H), 2.693 (t, 2H, J=7), 2.78–2.80 (m, 2H), 2.85–2.89 (m, 2H), 3.063 (t, 2H, J=7), 3.682 (s, 2H), 7.06–7.16 (m, 4H), 7.301 (d, 1H, J=7), 7.465 (d, 1H, J=7), 7.732 (s, 1H, NH), 7.980 (dd, 2H, J=8.5; 5.5). Anal. Calcd. for ($C_{21}H_{21}FN_2O$ +0.25$H_2O$): C 73.99, H 6.28, N 8.22; Found: C 74.06, H 5.99, N 8.09.

EXAMPLE 23

6-Methoxy-2-(3-phenoxypropyl)-1,2,3,4-tetyrahydro-9H-pyrido-[3,4-b]indole

From 3-phenoxypropyl bromide (215 mg, 1.0 mmol) and 6-methoxy-1,2,3,4-tetrahydro-9H-pyrido[3,4-b]indole (404 mg, 2.0 mmol) there was obtained 56 mg (16.6%) of the title compound as a white powder, mp 141–2° C. $^1H$ NMR ($CDCl_3$):2.05–2.13 (m, 2H), 2.77–2.91 (m, 6H), 3.695 (s, 2H), 3.851 (s, 3H), 4.075 (t, 2H, J=6.5), 6.76–6.80 (m, 1H), 6.90–6.96 (m, 5H), 7.16–7.30 (m, 3H), 7.590 (s, 1H, NH). Anal. Calcd. for $C_{21}H_{24}N_2O_2$: C 74.97, H 7:19, N 8.32; Found: C 74.71, H 7.16, N 8.19.

EXAMPLE 24

Preparation of 2-(2-Phenoxyethyl)-1,2,3,4-tetrahydro-9H-pyrido[3,4-b]indole

From 1,2,3,4-tetrahydro-9H-pyrido[3,4-b]indole (445 mg, 2.6 mmol), β-bromophenetole (260 mg, 1.3 mmol) and NaI (34 mg) in toluene (20 mL) was obtained 200 mg (53%) of the free base as a yellow powder, mp 181–2° C. $^1H$ NMR ($CDCl_3$): 1.653 (bs, 1H) 2.82–2.88 (m, 2H), 3.026 (t, 2H, J=6), 3.089 (t, 2H, J=6), 3.806 (bs, 2H), 4.226 (t, 2H, J=6), 6.93–6.99 (m, 2H), 7.06–7.16 (m, 2H), 7.26–7.32 (m, 3H), 7.478 (d, 1H, J=7.5), 7.747 (bs, 1H). Analysis, Calcd. for $Cl_{19}H_{20}N_2O$: C 78.05, H 6.90, N 9.58; Found: C 77.88, H 7.15, N 9.55.

EXAMPLE 25

Preparation of 2-(3-Phenoxypropyl)-1,2,3,4-tetrahydro-9H-pyrido[3,4-b]indole

From 1,2,3,4-tetrahydro-9H-pyrido[3,4-b]indole (430 mg, 2.5 mmol), 3-phenoxypropyl bromide (264 mg, 1.23 mmol) and NaI (48 mg) in toluene (20 mL) was obtained 270 mg (72%) of the free base as a yellow powder, mp 123–4° C. $^1H$ NMR ($CDCl_3$): 2.05–2.15 (m, 2H), 2.79–2.93 (m, 7H), 3.734 (bs, 2H), 4.080 (t, 2H, J=7), 6.90–6.96 (m, 2H), 7.06–7.16 (m, 2H), 7.26–7.32 (m, 3H), 7.476 (d, 1H, J=7), 7.716 (bs, 1H, NH). Analysis, Calcd. for $C_{20}H_{22}N_2O$: C 78.40, H 7.23, N 9.14; Found: C 78.03, H 7.15, N 9.07.

EXAMPLE 26

Preparation of 2-(3-Phenylpropyl)-1,2,3,4-tetrahydro-9H-pyrido[3,4-b]indole

From 1,2,3,4-tetrahydro-9H-pyrido[3,4-b]indole (200 mg, 1.16 mmol), 3-phenylpropyl bromide (125 mg, 0.63 mmol) and NaI (48 mg) in toluene (5 mL) was obtained 120 mg (66%) of the free base as a yellowish powder, mp 130–1° C. $^1$H NMR (CDCl$_3$): 1.90–2.00 (m, 2H), 2.646 (t, 2H, J=7.5), 2.706 (t, 2H, J=7.5), 2.82–2.87 (m, 4H), 3.695 (s, 2H), 7.05–7.32 (m, 8H), 7.470 (d, 1H, J=7), 7.695 (bs, 1H, NH). Analysis, Calcd. for C$_{20}$H$_{22}$N$_2$: C 82.72, H 7.64, N 9.65; Found: C 82.39, H 7.62, N 9.60.

EXAMPLE 27

Preparation of 4-Benzoyl-1-(2-phenoxyethyl) piperidine and the hydrochloride

From P-bromophenetole (302 mg, 1.5 mmol) and 4-benzoylpiperidine (568 mg, 3.0 mmol) in toluene (15 mL) was obtained 387 mg (83%) of the free base as a yellowish viscous oil. $^1$H NMR (CDCl$_3$): 1.84–1.91 (m, 4H), 2.26–2.34 (m, 2H), 2.853 (t, 2H, J=7), 3.07–3.11 (m, 2H), 3.20–3.30 (m, 1H), 4.129 (t, 2H, J=7), 6.90–6.97 (m, 3H), 7.28–7.31 (m, 1H), 7.44–7.58 (m, 4H). 7.92–7.95 (m, 2H). The hydrochloride mp 161–2° C. Analysis, Calcd. for C$_{20}$H$_{24}$ClNO$_2$: C 69.45, H 6.99, N 4.05; Found: C 69.37, H 7.11, N 3.99.

EXAMPLE 28

Preparation of 4-Benzyl-1-(3-sulfopropyl) piperidinium inner salt

To a solution of 1,3-propanesultone (383 mg, 3.14 mmol, in 2-butanone (8 mL) neat 4-benzylpiperidine (500 mg, 2.85 mmol, was added in one portion. The vessel was stoppered and the reaction was allowed to stir at 25° C. for 24 h. A colorless suspension was present. Ether (40 mL) was added and the suspension was stirred an additional 20 min. The solvent was decanted, fresh ether added and the suspension was re-stirred. This was repeated. The solid was collected from the resulting suspension and washed with ether (3×2 mL). The ether damp solid was crystallized from water (dissolved in warm solvent (3 mL cloudy solution), hot filtered through Celite (still cloudy solution), allowed to cool to 4° C.). A solid mass was obtained. This was diluted with ice water (10 mL), the resulting slurry filtered and the collected solid washed with ice water (3×3 mL). The damp filter cake was dried in vacuo (0.005 Torr, 25° C., then 100° C. (some high boiling material came off at the higher temperature) to give a colorless powder (320 mg, 38%, pure by NMR as a mixture of isomers); mp 167–172° C; $^1$H NMR (D$_2$O) δ1.13–1.60 (m, 2 H), 1.77–1.95 (m, 2 H), 2.13 (p, J=7.5 Hz, 2 H), 2.52–2.67 (m, 2 H), 2.78–3.00 (m, 4 H), 3.20 (t, J=7.5 Hz, 2 H), 3.45–3.61 (m, 2 H), 7.21–7.39 (m, 5 H).

An analytical sample was prepared according to the following procedure. The above powder (180 mg) was dissolved in hot water (2 mL), hot filtered and allowed to cool to 25° C. A solid formed. The water was decanted and the solid washed with water (0.5 mL). The wet solid was re-dissolved in hot water (0.5 mL) and the resulting solution allowed to cool to 25° C. The resulting solid was collected washed with water (3×0.5 mL) and dried in vacuo (100° C., 0.005 Torr) to give a colorless crystalline solid (29 mg); mp 177–178° C. when added to an oil bath of this temperature. When added to a cooler oil bath the solid melts at 224–225° C. (dec). Anal. Calcd for C$_{15}$H$_{23}$NO$_3$S -1.5 H$_2$O: C, 55.55; H, 8.08; N, 4.32. Found: C, 55.72; H, 7.95; N, 4.32.

EXAMPLE 29

Preparation of 1-[2-aza-1-oxo-2-phenylethyl]-4-benzylpiperidine

To a stirred solution of 4-benzylpiperidine (500 mg, 2.85 mmol, in toluene (10 mL) neat phenylisocyanate (341 mL, 374 mg, 3.14 mmol) was added in one portion. The reaction was allowed to stir at 90° C. under N$_2$ for 24 hours. The toluene was removed in vacuo (water aspirator, 45–50° C.) to give a colorless oil that solidified upon standing. The solid was dried further (25° C., 0.005 Torr). The solid was crystallized from 95% EtOH (dissolved in hot solvent (2 mL), hot filtered, allowed to cool to 25° C., collected solid, washed with ice cold 95% EtOH (3×2 mL) and dried in vacuo (56° C., 0.005 Torr)) to give a fluffy, colorless solid (530 mg, 63%); mp 130–131° C.; $^1$H NMR (CDCl$_3$) δ1.16–1.37 (m, 2 H), 1.61–1.82 (m, 3 H), 2.57 (d, J=6.9 Hz, 2 H), 2.75–2.90 (m, 2 H), 4.04 (d, J=14 Hz, 2 H), 6.43 (bs, 1 H), 6.95–7.38 (m, 10 H). Anal. Calcd for C$_{19}$H$_{22}$NO: C, 77.52; H, 7.53; N, 9.52. Found: C, 77.58; H, 7.67; N, 9.54.

EXAMPLE 30

Preparation of 1-[2-aza-1-oxo-2-(4-nitrophenyl) ethyl]-4-benzylpiperidine.

From 4-benzylpiperidine (1.00 g, 5.70 mmol, and 4-nitrophenylisocyanate (1.03 g, 6.27 mmol, there was obtained the product as a pale yellow solid (1.51 g, 78%, pure by NMR); mp 129.5–130.5° C.; $^1$H NMR (CDCl$_3$) δ1.16–1.37 (m, 2 H), 1.67–1.87 (m, 3 H), 2.58 (d, J=6.6 Hz, 2 H), 2.80–2.95 (m, 2 H), 4.07 (d, J=14 Hz, 2 H), 6.88 (s, 1 H), 7.12–7.35 (m, 5 H), 7.52 (d, J=9.0 Hz, 2 H), 8.16 (d, J=9.0 Hz, 2 H).

EXAMPLE 31

Preparation of 1-[2-aza-1-oxo-2-(4-aminophenyl) ethyl]-4-benzylpiperidine.

A mixture of 4-benzyl-1-((N-(4-nitrophenyl)aza) carbonyl)piperidine (1.50 g, 4.42 mmol) and Pd/C (10%, 150 mg, Aldrich) in MeOH (200 mL) was shaken under H$_2$ (20–30 psi, Parr) for 45 min at 25° C. The catalyst was removed by filtration (Celite). The resulting solution was acidified with a dilute solution of HBr in MeOH (pH paper to red). The MeOH was removed in vacuo (rotoevap, 35–40° C.) to give a colorless solid. The solid was crystallized from MeOH/H$_2$O. mp 325° C. dec.; $^1$H NMR (DMSO-d$_6$) δ0.90–1.10 (m, 2 H), 1.40–1.70 (m, 3 H), 2.42 (d, J=6.6 Hz, 2 H), 2.55–2.70 (m, 2 H), 4.06 (d, J=13 Hz, 2 H), 7.00–7.25 (m, 7 H), 7.54 (d, J=8.7 Hz, 2 H), 8.65 (s, 1 H), 9.90 (bs, 3 H). Anal. Calcd for C$_{19}$H$_{24}$BrN$_3$O: C, 58.47; H, 6.20; N, 10.76. Found: C, 58.69; H, 6.26; N, 10.72.

EXAMPLE 32

Preparation of 4-(4-Chlorobenzyl) piperidine hydrochloride.

The procedure of Faraj et al., was adapted (Faraj, B. A.; Israili, Z. H.; Kight, N. E.; Smissman, E. E.; Pazdernik, T. J. *J. Med Chem.* 19:20 (1976)). A near colorless powder was obtained; mp 179–184° C., $^1$H NMR (D$_2$O) δ1.31–1.50 (m, 2 H), 1.75–1.95 (m, 3 H), 2.58 (d, J=6.9 Hz, 2 H), 2.82–2.99 (m, 2 H), 3.58 (d, J=12.6 Hz, 2 H), 7.20 (d, J=8.1 Hz, 2 H), 7.34 (d, J=8.4 Hz).

EXAMPLE 33

1-Allyl-4-(4-chlorobenzyl)piperidine hydrobromide and 1,1-Bisallyl-4-(4-chloro-benzyl) piperidinium iodide A mixture of 4-(4-chlorobenzyl)piperidine hydrochloride (1.00 g, 4.06 mmol), K$_2$CO$_3$ (1.15 g, 8.32 mmol,) and allyl iodide (1.02 g, 6.09 mmol) in CH$_3$CN (25 ml) was stirred at reflux under N$_2$ for 4 h. The reaction was added to 5% aqueous HCl (200 mL). The resulting cloudy solution was extracted with CHCl$_3$ (3×50 mL). The extract was washed with 10% aqueous NH$_4$OH (2×50 mL) and water (2×50 ml), filtered through cotton and the solvent was removed in vacuo to give an orange gum mixed with an amber oil. The mixture was washed with hexanes (3×10 ml) which dissolved the oil, leaving the gum behind. The solvent was removed from the hexanes portion to give an amber oil. Purification of this oil was effected by silica gel chromatography (2.5×20 cm column) with CHCl$_3$ elution to remove the more mobile impurities and with 1% EtOH/99% CHCl$_3$ to remove the product. Solvent removal from the pure fractions yielded an amber oil. This was dissolved in MeOH (10 mL, cloudy solution) filtered through Celite and the MeOH was removed in vacuo to yield a clear amber oil. This was dissolved in hexanes (10 mL), the insoluble portion removed by filtration through Celite and the solvent was removed in vacuo to give the monoallyl piperidine as a clear amber oil (340 mg, 34%;): $^1$H NMR (CDCl$_3$) d 1.22–1.68 (m, 5 H), 1.89 (t, J=8.4 Hz, 2 H,), 2.50 (d, J=6.6 Hz, 2 H), 2.83–3.05 (m,4 H), 5.05–5.22 (m, 2 H), 5.79–5.98 (m, 1 H), 7.05 (d, J=8.1 Hz, 2 H), 7.23 (d, J=8.1 Hz, 2 H). The hydrobromide salt was obtained as a pale yellow powder (413 mg, 92%): mp 114–116.5° C.; HRMS calcd for C$_{15}$H$_{20}$ClNO 249.1284, found 249.1279.

The above described gum was mixed with ether (45 mL) and was stirred at 25° C. for 24 h to give an orange suspension. The solid was collected, washed with ether (3×4 mL) and was allowed to air dry to give a pale orange powder (~600 mg). This was suspended in toluene (22 mL). Acetone was added to the stirred suspension at 25° C. until a homogeneous solution was obtained (22 mL). The flask was covered with a tissue and was stored at 25° C. so as to allow the acetone to evaporate. A crystalline solid formed over the course of six days (a temperature >25° C. results in the formation of an oil). The solid was collected, washed with toluene (3×2 mL) and was dried in vacuo (0.005 Torr, 56° C.) to give the bisallyl piperidine as colorless, fluffy needles (448 mg, 26%): mp 110.5–111.5° C.; $^1$H NMR (CDCl$_3$) d 1.60–1.91 (m, 4 H), 2.16–2.35 (m, 1 H), 2.69 (d, J=7.2 Hz, 2 H), 3.54 (d, J=13 Hz, 2 H), 3.72–3.98 (m, 2 H), 4.10 (d, J=6.9 Hz, 2 H), 4.30 (d, J=6.9 Hz, 2 H), 5.70–6.08 (m, 6 H), 7.12 (d, J=8.1 Hz, 2 H), 7.24 (d, J=8.1 Hz, 2 H). Anal. Calcd for C$_{18}$H$_{25}$ClIN: C, 51.75; H, 6.03; N, 3.35. Found: C, 51.88; H, 5.90; N, 3.27.

EXAMPLE 34

Preparation of 5-(3-Benzylpiperidinyl)valeric acid methyl ester.

3-Benzylpiperidine hydrochloride. To a solution of 3-benzylpyridine (10 g, 59.8 mmol) in methanol (150 mL) were added PtO$_2$(350 mg) and HCl conc. (5 mL). This heterogeneous solution was hydrogenated in a Parr hydrogenator at 20–25 psi at 25° C. and for 24 hrs then filtered through a celite pad and concentrated in vacuum. The crude compound was purified by crystallization from acetone/diethyl ether to give a white solid (8.5 g, 68%). $^1$H-NMR (DMSO): 1.05–1.2 (m, 1H); 1.5–1.75 (m, 3H); 1.87–2.05 (m, 1H); 2.4–2.55 (m, 3H); 2.57–2.75 (m, 1H); 2.982 (d, J=11.7, 1H); 3.97 (d, J=12.0, 1H); 7.136 (d, J=7.0, 2H); 7.184 (d, J=7.0, 1H), 7.296 (t, J=7.2, 2H); 8.89 (bs, 1H); 9.15 (bs, 1H).

5-[(3-Benzyl)-1-piperidinyl]valeric acid methyl ester. To a solution of 3-benzylpiperidine hydrochloride (2 g, 9.4 mmol) in DMF (40 mL) were added methyl 5-bromovalerate (1.6 mL, 11.3 mmol) and potassium carbonate (3.2 g, 23.6 mmol). This heterogeneous mixture was heated at 110° C. for 1 hr then cooled at 25° C., diluted with water (200 mL) and diethyl ether (200 mL). The aqueous solution was extracted with diethyl ether (100 mL) and the collected organic phase was washed with brine (200 mL), dried and concentrated in vacuum. The crude compound was purified by silica gel column chromatography using CH$_2$Cl$_2$/MeOH as eluant to afford the title compound as an oil (1.76 g, 65%). $^1$H-NMR (CDCl$_3$): 0.8–1.0 (m, 1H); 1.4–1.7 (m, 8H); 1.8–1.95 (m, 2H); 2.25–2.35 (m, 4H); 2.4–2.6 (m, 2H); 2.75–2.9 (m, 2H); 3.65 (8, 3H); 7.132 (d, J=7.0, 2H); 7.186 (d, J=7.2, 11); 7.264 (t, J=7.2, 2H).

EXAMPLE 35

Preparation of 4-(3-Benzylpiperidinyl)butyric acid ethyl ester

From 3-benzylpiperidine hydrochloride (0.7 g, 4.0 mmol), ethyl 4-bromobutyrate (0.685 mL, 4.8 mmol) and potassium carbonate (1.1 g, 8.0 mmol) there was obtained the title compound as an oil (0.75 g, 65%). $^1$H-NMR (CDCl$_3$): 0.8–1.0 (m, 1H); 1.241 (t, J=7.2, 3H); 1.4–2.0 (m, 6H); 1.791 (t, J=7.5, 2H); 2.296 (t, J=7.5, 4H); 2.4–2.6 (m, 2H); 2.7–2.9 (m, 2H); 4.112 (q, J =7.2, 2H); 7.1–7.3 (m, 5H).

EXAMPLE 36

Preparation of 3-Benzyl-1-(5-hydroxypentyl) piperidine

To a solution of 4-[(3-benzyl)-1-piperidinyl]valeric acid ethyl ester (0.96 g, 3.31 mmol) in THF dry (20 mL) were added portionwise LiAlH$_4$ (0.38 g, 9.95 mmol). The resulting mixture was stirred at 25° C. for 2 hrs then diluted with NH$_4$Cl (sat. solution, 50 mL) and extracted with ethyl acetate (3×30 mL). The collected organic phases were washed with brine (50 mL), dried and concentrated in vacuum. The crude compound was purified by filtration on silica gel (260–400 mesh) using CH$_2$Cl$_2$/MeOH 8/2 as solvent to give the title compound as an oil (0.70 g, 81%). $^1$H-NMR (CDCl$_3$): 0.8–1.0 (m, 1H); 1.3–1.45 (m, 2H); 1.45–1.75 (m, 9H); 1.8–2.0 (m, 2H); 2.25–2.4 (m, 2H); 2.4–2.6 (m, 2H); 2.78–2.93 (m, 2H); 3.607 (t, J=6.3, 2H); 7.136 (d, J=7.2, 2H); 7.186 (d, J=6.9, 1H); 7.264 (t, J=7.2, 2H).

EXAMPLE 37

Preparation of 3-Benzyl-1-(4-hydroxybutyl) piperidine.

From 4-[(3-benzyl)-1-piperidinyl]-butyric acid ethyl ester (0.45 g, 1.55 mmol) and LiAlH$_4$ (0.18 g, 4.6 mmol) there was obtained the title compound as an oil (0.360 g, 94%). $^1$H-NMR (CDCl$_3$): 0.85–1.05 (m, 1H); 1.5–1.8 (m, 9H); 1.85–2.0 (m, 2H); 2.3–2.4 (m, 2H); 2.4–2.6 (m, 2H); 2.85–3.0 (m, 2H); 3.45–3.6 (m, 2H); 7.133 (d, J=7.2, 2H); 7.186 (d, J=7.2, 1H); 7.261 (t, J=7.2, 2H).

EXAMPLE 38

Preparation of 1-Allyl-2-benzylpiperidine, hydrobromide (A) and 2-benzyl-l,1-diallylpiperidinium iodide (B)

A mixture of 2-benzylpiperidine hydrochloride (500 mg, 2.36 mmol), K$_2$CO$_3$ (652 mg, 4.72 mmol) and allyl iodide (595 mg, 3.54 mmol) in CH$_3$CN (25 mL) was stirred at reflux under N$_2$ for 24 h. The reaction was allowed to cool to room temperature and was added to 5% aqueous HCl (100 mL). The resulting cloudy solution was extracted with CHCl$_3$ (3×50 mL). The extract was washed with 10% aqueous NH$_4$OH (2×50 mL) and water (2×50 mL), filtered through cotton and the solvent removed in vacuo to give an oil which partially solidified upon standing. The mixture was washed with hexanes (3×2 mL) to give a solid (vide infra) and a hexanes soluble portion. The hexanes-were removed in vacuo to give an oil. Purification was effected by silica gel chromatography (CHCl$_3$ elution) to give a cloudy amber oil. This was dissolved in MeOH (5 mL, cloudy solution), filtered through celite (clear solution) and the MeOH removed in vacuo to yield a clear amber oil (129 mg, 25%); $^1$H NMR (CDCl$_3$) δ1.13–1.70 (m, 6 H), 2.25–2.65 (m, 3 H), 2.78–2.89 (m, 1 H), 3.08–3.28 (m, 2 H), 3.45 (dd, J$_1$=8.4 Hz, J$_2$ =14 Hz, 1 H), 5.15–5.29 (m, 2 H), 5.90–6.06 (m, 1 H), 7.08–7.32 (m, 5 H).

The hydrobromide salt; mp 112–114° C.; $^1$H NMR (CDCl$_3$) δ1.12–4.00 (m, 13 H), 5.51–5.19 (m, 2 H), 6.03–6.50 (m, 1 H), 7.11–7.38 (m, 5 H), 11.42 (bs, 1 H).

Analytical sample; mp 116–117.5° C. Anal. Calcd. for C$_{15}$H$_{22}$BrN: C, 60.81; H, 7.48; N, 4.73. Found: C, 60.82; H, 7.65; N, 4.73.

The solid obtained from the hexanes wash (vide supra) was crystallized from acetone to yield colorless cubes (210 mg, 23%); mp 179–180° C.; $^1$H NMR (CDCl$_3$) δ1.30–1.50 (m, 1 H), 1.75–2.11 (m, 5 H), 2.86 (t, J=12 Hz, 1 H), 3.33–3.75 (m, 4 H), 4.08–4.19 (m, 1 H), 4.32–4.51 (m, 2 H), 4.88–4.99 (m, 1 H), 5.72–5.86 (m, 2 H), 5.93–6.28 (m, 4 H), 7.13–7.35 (m, 5 H).

An analytical sample was dried in vacuo (0.005 Torr, 100° C.); mp 180–181.5° C. Anal. Calcd for C$_{18}$H$_{26}$IN: C, 56.40; H, 6.84; N, 3.65. Found: C, 56.33; H, 6.84; N, 3.62.

EXAMPLE 39

Preparation of 2-Benzyl-1-cyclopropylmethyl piperidine, hydrobromide.

From 2-benzylpiperidine hydrochloride (500 mg, 2.36 mmol), K$_2$CO$_3$ (652 mg, 4.72 mmol) and bromomethylcyclopropane (478 mg, 3.54 mmol) in CH$_3$CN (25 mL) there was obtained the free base as a light amber, clear oil (320 mg, 59%, pure by TLC, and $^1$H NMR); $^1$H NMR (CDCl$_3$) δ0.15 (q, J=4.8 Hz, 2 H), 0.45–0.59 (m, 2 H), 0.85–1.03 (m, 1 H), 1.12–1.32 (m, 2 H), 1.38–1.75 (m, 4 H), 2.39–2.55 (m, 3 H), 2.58–2.73 (m, 2 H), 2.96–3.08 (m, 1 H), 3.12 (dd, J$_1$=13 Hz, J$_2$=3.6 Hz, 1 H), 7.13–7.31 (m, 5 H).

The hydrobromide salt; mp 140–143° C.; $^1$H NMR (CDCl$_3$) δ0.32–3.78 (m, 18 H), 7.14–7.36 (m, 5 H), 11.24 (bs, 1 H).

Analytical sample; mp 143–145° C. Anal. Calcd. for C$_{16}$H$_{24}$BrN: C, 61.94; H, 7.80; N, 4.51. Found: C, 62.22; H, 7.80; N, 4.46.

EXAMPLE 40

Preparation of 5-(4-Benzylpiperidinyl) valeric acid (59)

To a solution of 5-[(4-benzylpiperidine)-1-yl]valeric acid methyl ester (0.5 g, 1.73 mmol) in MeOH (8 mL) was added 2N NaOH (1.73 mL, 3.45 mmol). The resulting solution was heated at reflux for 2 h then neutralized with 5% HCl and concentrated in vacuum. The crude mixture was triturated with CH$_2$Cl$_2$/MeOH 1/1 (12 mL) for 1 h. The resulting solid was further triturated with diethyl ether (10 mL) for 20 h to give the title compound as a white solid (0.37 g, 78%), mp 148–151° C. $^1$H-NMR (DMSO): 1.3–1.5 (m, 4H), 1.5–1.5 (m, 5H), 2.19 (t, J=7.0, 2H), 2.4–2.5 (m, 2H), 2.56 (t, J=11.4, 2H), 2.79 (t, J=7.6, 2H), 3.19 (d, J=11.7, 2H), 7.1–7.2 (m, 3H), 7.25 (t, J=7.2, 2H).

EXAMPLE 41

Preparation of 4-(4-Benzylpiperidinyl) butyric acid ethyl ester hydrobromide salt From 4-benzylpiperidine (1.0 mL, 5.7 mmol), ethyl 4-bromobutyrate (0.898 mL, 6.27 mmol) and potassium carbonate (1.6 g, 11.4 mmol) there was obtained free base as an oil (1.25 g, 76%). $^1$H-NMR (CDCl$_3$): 1.24 (t, J=7.2, 3H), 1.26–1.4 (m, 2H), 1.45–1.60 (m, 1H), 1.63 (bd, J=12.9, 2H), 1.75–1.95 (m, 4H), 2.25–2.40 (m, 4H), 2.53 (d, J=6.9, 2H), 2.90 (bd, J=11.4, 2H), 4.11 (q, J=7.2, 2H), 7.13 (bd, J=7.2, 2H), 7.19 (d, J=6.9, 1H), 7.27 (t, J=7.2, 2H).

The HBr salt; mp 159–160° C. $^1$H-NMR (DMSO): 1.3–1.45 (m, 2H), 1.6–1.85 (m, 5H), 2.461 (t, J=7.2, 2H), 2.4–2.6 (m, 3H), 2.7–2.9 (m, 2H), 2.9–3.1 (m, 2H), 3.2–3.5 (m, 6H), 7.1–7.3 (m, 5H), 9.0 (bs, 1H).

EXAMPLE 42

Preparation of 4-(4-Benzylpiperidinyl) butyric acid

From 4-[(4-benzyl)-piperidine)-1-yl]butyric acid ethyl ester (0.3 g, 1.036 mmol) there was obtained the title compound as a white solid (0.24 g, 89%); mp=154° C. $^1$H-NMR (DMSO): 1.07–1.25 (m, 2H), 1.4–1.65 (m, 5H), 1.954 (t, J=11.4, 2H), 2.04 (s, 1H), 2.195 (t, J=6.6, 2H), 2.35 (t, J=6.6, 2H), 2.4–2.5 (m, 2H), 2.88 (bd, J=11.4, 2H), 7.06–7.18 (m, 3H), 7.23 (t, J=7.5, 2H).

EXAMPLE 43

Preparation of 5-(4-Benzylpiperidinyl) valeronitrile

From 4-benzylpiperidine (2.0 mL, 11 mmol), 5-bromovaleronitrile (2 g, 12 mmol) and potassium carbonate (3.1 g, 22 mmol) there was obtained the title compound as an oil (2.47 g, 85%). $^1$H-NMR (CDCl$_3$): 1.2–1.4 (m, 2H), 1.45–1.6 (m, 1H), 1.55–1.75 (m, 6H), 1.866 (t, J=11.4, 2H), 2.25–2.45 (m, 4H), 2.53 (d, J=6.9, 2H), 2.88 (bd, J=11.4, 2H), 7.134 (d, J=7.2, 2H), 7.193 (d, J=7.2, 1H), 7.274 (t, J=7.2, 2H).

EXAMPLE 44

Preparation of 4-Benzyl-1-(5-aminopentyl) piperidine hydrochloride

To a solution of 5-[(4-benzylpiperidine)-1-yl]valeronitrile (0.8 g, 3.12 mmol) in ethanol (50 mL) and conc. HCl (1.5 mL) was added platinum dioxide (0.15 g). The resulting mixture was hydrogenated in a Parr hydrogenator at 30 psi for 2 h, then filtered through a pad of celite and concentrated in vacuum to afford the title compound as a hygroscopic salt (0.7 g, 67%), mp 200° C. dec. $^1$H-NMR D$_2$O): 1.3–1.55 (m, 4H), 1.6–1.8 (m, 4H), 1.87 (bd, J=13.2Hz, 2H), 2.60 (d, J=6.6Hz, 2H), 2.85 (t, J=12.6Hz, 2H), 2.91–3.10 (m, 4H), 3.51 (d, J=12.3Hz, 2H), 7.2–7.3 (m, 3H), 7.344 (t, J=7.2Hz, 2H).

EXAMPLE 45

Preparation of 4-Benzyl-1-(3-p-toluenesul fonyloxypropyl)-piperidine

To a solution of 4-benzyl-1-(3-hydroxypropyl)piperidine (1.0 g, 4.29 mmol) in CH$_2$Cl$_2$ (20 mL) were added TEA (1.2 mL, 8.57 mmol) and dropwise a solution of p-toluenesulfonyl chloride (1.22 g, 6.4 mmol) in $CH_2Cl_2$ (10 mL). The resulting solution was stirred at 25° C. for 2 h then diluted with $CH_2Cl_2$ (60 mL) and washed with $NH_4Cl$ (2×100 mL), dried and concentrated in vacuum to afford the crude intermediate, which was purified by trituration with EtOAc (10 mL) to give the title compound as a white solid (0.63 g, 38%), mp 143–145° C. $^1$H-NMR (CDCl$_3$): 1.2–1.45 (m, 2H), 1.65–1.85 (m, 3H), 2.319 (s, 3H), 2.502 (d, J=7.2Hz, 2H), 2.6–2.8 (m, 2H), 3.338 (t, J=12.6Hz, 2H), 3.875 (d, J=12.6, 2H), 4.277 (t, J=8.1Hz, 2H), 4.421 (t, J=8.4Hz, 2H), 7.064 (d, J 7.2Hz, 2H), 7.122 (d, J=7.8Hz, 2H), 7.15–7.30 (m, 3H), 7.76 (d, J=7.8Hz, 2H).

EXAMPLE 46

Preparation of 4-Benzyl-1-(3-azidopropyl) piperidine.

Sodium azide was added to a solution of 4-benzyl-1-(3-p-toluenesulfonyloxypropyl)piperidine (0.216 g, 0.56 mmol) in DMF (5 mL). The resulting solution was stirred at 80° C. for 3 h then cooled at 25° C., diluted with water (50 mL) and extracted with diethyl ether (2×50 mL). The collected organic phase was washed with water (2×50 mL), dried and concentrated in vacuum to afford crude title compound as an oil (0.15 g). $^1$H-NMR (CDCl$_3$): 1.2–1.4 (m, 2H), 1.4–1.6 (m, 1H), 1.628 (dd, J =13.2Hz, 2H), 1.761 (t, J=7.2Hz, 2H), 1.857 (t, J=11.4Hz, 2H), 2.367 (t, J=7.2Hz, 2H), 2.53 (d, J=7.2Hz, 2H), 2.86 (bd, J 11.4, 2H), 3.314 (t, J=6.9Hz, 2H), 7.14 (d, J=7.5Hz, 2H), 7.19 (d, J=6.9, 1H), 7.275 (t, J=7.2Hz, 2H).

EXAMPLE 47

Preparation of 4-Benzyl-1-(3-aminopropyl) piperidine (68)

To a solution of 4-benzyl-1-(3-azidopropyl)piperidine (0.14 g, 0.54 mmol) in methanol (5 mL) was added Pd/C 5% (6 mg) and the resulting heterogeneous mixture was hydrogenated at 1 atm for 4 h. then filtered through a celite pad and concentrated in vacuum. The crude compound was purified by trituration with diethyl ether (5 mL) to give the title compound as a white solid (0.075g, 60%), mp 140–141° C. $^1$H-NMR (DMSO): 1.05–1.21 (m, 2H), 1.35–1.55 (m, 3H), 1.55–1.70 (m, 2H), 1.746 (t, J=11.1Hz, 2H), 2.281 (t, J=6.6Hz, 2H), 2.4–2.5 (m, 2H), 2.5–2.85 (m, 4H), 7.06–7.18 (m, 3H), 7.23 (t, J=7.2Hz, 2H), 7.8 (bs, 2H).

EXAMPLE 48

Preparation of 1-(4-phenoxybutyl)-2-hydroxymethylpiperidine, hydrobromide (78)

From 2-hydroxymethylpiperidine (1.00 g, 8.68 mmol, $K_2CO_3$ (1.32 g, 9.55 mmol) and 4-phenoxybutyl bromide (9.94 g, 43.4 mmol, in $CH_3CN$ (50 mL) there was obtained the free base as a clear amber oil (1.52 g, 67%); $^1$H NMR (CDCl$_3$) δ1.20–1.90 (m, 10 H), 2.19–3.06 (m, 6 H), 3.40–3.50 (m, 1 H), 3.75 (dd, J$_1$=10.5 Hz, J$_2$=4.2 Hz, 1H), 3.97 (t, J=6.3 Hz, 2 H), 6.85–6.94 (m, 3 H), 7.23–7.32 (m, 2 H).

The hydrobromide salt; mp 113–115° C.; $^1$H NMR (CDCl$_3$) δ1.42–2.32 (m, 10 H), 2.80–4.49 (m, 10 H), 6.83–7.32 (m, 5 H), 9.95 (bs, 1 H).

Analytical sample; mp 114.5–116.5° C. Anal. Calcd for $C_{16}H_{26}BrNO_2$: C, 55.82; H, 7.61; N, 4.07. Found: C, 55.72; H, 7.70; N, 3.95.

EXAMPLE 49

1-(2-(4-Fluorophenoxy)ethyl)-2-(hydroxymethyl) piperidine hydrobromide

From 2-hydroxymethylpiperidine (500 mg, 4.34 mmol) and 2-(4-fluorophenoxy)ethyl bromide (999 mg, 4.56 mmol) there was obtained a colorless oil (970 mg, 88%): $^1$H NMR (CDCl$_3$) d 1.60–2.11 (m, 6 H), 2.67–3.59 (m, 6 H), 3.80 (dd, J$_1$=11 Hz, J$_2$=3.9 Hz, 1 H), 4.15 (dd, J$_1$=11 Hz, J$_2$=3.9 Hz, 1 H) 4.37–4.42 (m, 2 H), 7.13–7.35 (m, 4 H). The hydrobromide was obtained as a colorless powder (1.08 g, 96%): mp 103.5–105.5 ° C.; Anal. Calcd for $C_{14}H_{21}BrFNO_2$: C, 50.31; H, 6.33; N, 4.19. Found: C, 50.39; H, 6.15; N, 3.99.

EXAMPLE 50

DL-3-Phenoxypropyl-1-(3-phenoxypropyl) pipecolinate, hydrobromide

From DL-pipecolinic acid (1.00 g, 7.74 mmol), $K_2CO_3$ (2.20 g, 15.9 mmol) and 3-phenoxypropyl bromide (1.75 g, 8.13 mmol) in DMF (25 mL) there was obtained an oil (800 mg, 25%): $^1$H NMR (CDCl$_3$) d 1.61–2.61 (m, 11 H), 2.75–2.88 (m, 1 H), 2.99–3.11 (m, 1 H), 3.38–3.51 (m, 2 H), 4.22–4.40 (m, 4 H), 4.65 (t, J=6.0 Hz, 2 H), 7.17–7.32 (m, 6 H), 7.60 (t, J=7.5 Hz, 4 H); The hydrobromide was obtained as a colorless powder (825 mg, 97%): mp 94–96° C.; HRMS calcd for $C_{24}H_{31}NO_4$ 397.2253, found 397.2265.

EXAMPLE 51

(s)-2-(Hydroxymethyl)-1-(3-phenoxypropyl) pyrrolidine hydrobromide

From (s)-(+)-2-pyrrolidinemethanol (1.00 g, 9.89 mmol) and 3-phenoxypropyl bromide (2.23 g, 10.4 mmol) there was obtained a pale yellow oil (1.01 g, 43%): 1H NMR (CDCl$_3$) d 1.60–2.10 (m, 6 H), 2.20–2.75 (m, 4 H), 2.80–3.05 (m, 1 H), 3.15–3.25 (m, 1 H), 3.37 (d, J=9.0 Hz, 1 H), 3.64 (dd, J$_1$=10 Hz, J$_2$=3.3 Hz, 1 H), 4.04 (t, J=6.3 Hz, 2 H), 6.87–6.98 (m, 3 H), 7.23–7.32 (m, 2 H). The hydrobromide was obtained as a colorless solid (820 mg, 61%): mp 100–101.5° C.; Anal. Calcd for $C_{14}H_{22}BrNO_2$: C, 53.17, H, 7.01, N, 4.42. Found: C, 53.27, H, 6.72, N, 4.28.

EXAMPLE 52

Preparation of 3-benzyl-1-(3-phenoxypropyl) piperidine hydrobromide

From 3-benzyl piperidine (0.2 g, 1.14 mmol), 2-phenoxypropylbromine (0.27 ml, 1.7 mmol) and potassium carbonate (0.315 g, 2.28 mmol) there was obtained the free amine as an oil (0.306 g, 87%). $^1$H NMR (CDCl$_3$): 0.9–1.1 (m, 1H), 1.5–1.8 (m, 4H), 2.4–2.65 (m, 4H), 2.867 (t, J=10.5Hz, 2H), 4.01 (m, 2H), 6.85–7.0 (m, 3H), 7.15–7.35 (m, 7H).

The HBr salt was obtained as a white solid; m.p. 148–149° C. $^1$H NMR (CDCl$_3$): 1.05–1.15 (m, 1H), 1.8–2.0 (m, 2H), 2.3–2.7 (m, 7H), 2.7–2.9 (m, 1H), 3.1–3.3 (m, 2H), 3.4–3.55 (m, 1H), 3.623 (d, J=10.8Hz, 1H), 4.0–4.15 (m, 2H), 6.83 (d, J=8.1Hz, 2H), 6.967 (t, J=7.5Hz, 1H), 7.146 (d, J=6.9Hz, 2H), 7.2–7.35 (m, 5H), 11.32 (bs, 1H). MS (m/z): 309, 307, 188, 91. Anal. Calcd. for $C_{21}H_{28}BrNO$; C, 64.6, H 7.0, N 3.6; Found: C 64.28, H 7.26, N 3.50.

EXAMPLE 53

Preparation of 3-benzyl-1-(2-phenoxyethyl) piperidine hydrobromide

From 3-benzyl piperidine (0.2 g, 1.14 mmol), 1-p-toluenesulfonate-2-phenoxyethane (0.4 g, 1.3 mmol) and potassium carbonate (0.315 g, 2.28 mmol) there was obtained the free amine as an oil (0.22 g, 64%). $^1$H NMR (CDCl$_3$): 0.9–1.05 (m, 1H), 1.5–1.8 (m, 3H), 1.8–2.0 (m, 2H), 2.088 (t, J=11.1 Hz, 1H), 2.52 (dd, J=6.9 & 6.3Hz, 2H), 2.7–2.9 (m, 2H), 2.9–3.0 (m, 2H), 4.084 (t, J=6.0Hz, 2H), 6.88 (d, J=8.1Hz, 2H), 6.94 (t, J=7.2Hz, 1H), 7.143 (d, J=7.2Hz, 2H), 7.19 (d, J=6.9Hz, 1H), 7.2–7.35 (m, 4H).

The HBr salt was obtained as a white solid (0.148 g, 60%). m.p. 93–94° C. $^1$H NMR (CDCl$_3$): 1.0–1.23(m, 1H), 1.8–2.0(m, 2H), 2.2–2.8(m, 5H), 2.59(d, J=6.9Hz, 1H), 3.3–3.5(m, 2H), 3.56(d, J=11.4Hz, 1H), 3.68(d, J=10.5Hz, 1H), 4.5–4.63(m, 2H), 6.84(d, J=7.8Hz, 2H), 7.014(t, J=7.5Hz, 1H), 7.13(d, J=6.9Hz, 2H), 7.15–7.35(m, 5H), 11.55(bs, 1H). MS (m/z): 295, 188, 91. Calcd. for C$_{20}$H$_{26}$BrNO; C 43.8, H 6.7, N 3.72; Found: C 63.63, H 6.76, N 3.73.

EXAMPLE 54

Preparation of 3-benzyl-1-(4-phenylbutyl) piperidine hydrobromide

From 3-benzyl piperidine (0.3 g, 1.7 mmol), 1-p-toluenesulfonate-4-phenylbutane (0.781 g, 2.56 mmol) and potassium carbonate (0.473 g, 3.42 mmol) there was obtained the free amine as an oil (0.313 g, 60%). $^1$H NMR (CDCl$_3$): 0.7–1.0 (m, 1H), 1.4–1.7 (m, 8H), 1.7–2.0 (m, 2H), 2.317 (bs, 2H), 2.4–2.7 (m, 4H), 2.7–2.9 (m, 2H), 7.1–7.35 (m, 10H). The HBr salt was obtained as a solid; m.p. 105–107° C. $^1$H NMR (CDCl$_3$): 1.0–1.2 (m, 1H), 1.55–1.6 (m, 4H), 1.80–2.0 (m, 4H), 2.15–3.0 (m, 11H), 3.389 (d, J=11.1 Hz, 1H), 3.51 (bd, J=9.6Hz, 1H), 7.0–7.5 (m, 10H), 11.2 (bs, 1H). MS (m/z): 307, 188, 91. Anal, Calcd. for C$_{21}$H$_{30}$BrN; C 68.00, H 7.5, N 3.6; Found: C 67.68, H 7.69, N 3.44.

EXAMPLE 55

Preparation of 3-benzyl-1-(2-phenylethyl) piperidine hydrobromide

From 3-benzylpiperidine (0.2 g, 1.14 mmol), 2-bromoethylbenzene (0.23 mL, 1.7 mmol) and potassium carbonate (0.315 g, 2.28 mmol) there was obtained the free amine as an oil (0.313 g, 98%). $^1$H NMR (CDCl$_3$): 0.95–1.1 (m, 1H), 1.4–1.8 (m, 4H), 1.9–2.1 (m, 2H), 2.4–2.5 (m, 4H), 2.5–3.1 (m, 4H), 7.1–7.32 (m, 10H).

HBr salt was obtained as a solid; m.p. 137–142° C. $^1$H NMR (CDCl$_3$): 1.0–1.3 (m, 3H), 1.7–2.0 (m, 2H), 2.2–2.5 (m, 2H), 2.5–2.65 (m, 2H), 2.7–2.9 (m, 1H), 3.1–3.4 (m, 4H), 3.622 (d, J=11.1 Hz, 1H), 7.0–7.5 (m, 1OH), 11.47 (bs, 1H). MS (m/z): 278, 188, 124, 91. Analysis, Calcd. for C$_{20}$H$_{26}$BrN; C 66.6, H 7.0, N 3.9; Found: C 66.66, H 7.13, N 3.73.

EXAMPLE 56

Preparation of 1-p-toluenesulfonate-2-(3-trifluoromethylphenyl)ethane

To a solution of 3-trifluoromethylphenethyl alcohol (1.0 g, 5.2 mmol) in CH$_2$Cl$_2$ (30 mL) were added Et$_3$N (1.5 mL, 10.5 mmol) and dropwise a solution of p-toluenesulfonyl chloride (1.5 g, 7.9 mmol) in CH$_2$Cl$_2$ (20 mL). The resulting solution was stirred at 25° C. for 3 h then diluted with CH$_2$Cl$_2$ (50 mL) and washed with HCl 5% (2×100 mL), brine (100 mL), dried and concentrated in vacuum. The crude compound was purified by flash-chromatography on silica gel using EtOAc/n-hexane as eluant to afford the title compound as an oil (1.68 g, 94%). $^1$H NMR (CDCl$_3$): 2.42 (s, 3H), 3.01 (t, J=6.6Hz, 2H), 4.24 (t, J=6.9Hz, 2H), 7.26 (d, J=8.1Hz, 2H), 7.32 (d, J=6.3Hz, 2H), 7.378 (t, J=7.8Hz, 1H), 7.504 (d, J=7.5Hz, 1H), 7.65 (d, J=8.1Hz, 2H).

EXAMPLE 57

Preparation of 3-benzyl-1-[2-(3-trifluoromethylphenyl)ethyl]piperidine hydrobromide From 3-benzylpiperidine hydrochloride (0.2 g, 0.94 mmol), 1-p-toluenesulfonate-2-(3-trifluoromethylphenyl) ethane (0.45 g, 1.32 mmol) and potassium carbonate (0.25 g, 1.9 mmol) there was obtained the free amine as an oil (0.23 g, 70%). NMR (CDCl$_3$): 0.9–1.1 (m, 1H), 1.5–1.8 (m, 4H), 1.83–2.1 (m, 2H), 2.4–2.6 (m, 4H), 2.7–3.0 (m, 4H), 7.163 (d, J=7.5Hz, 2H), 7.20 (d, J=6.9Hz, 1H), 7.24–7.48 (m, 6H).

The HBr salt was obtained as a solid; m.p. 152–154° C. $^1$H NMR (DMSO): 1.0–1.2 (m, 1H), 1.55–1.75 (m, 2H), 1.75–1.90 (m, 1H), 1.95–2.1 (m, 1H), 2.53 (d, J=6.6Hz, 2H), 2.68 (q, J=11.7Hz, 1H), 2.75–2.4 (m, 1H), 2.95–3.15 (m, 2H), 3.2–3.4 (m, 3H), 3.39 (d, J=10.8Hz, 1H), 3.53 (d, J=11.1 Hz, 1H), 7.16 (d, J=7.5Hz, 2H), 7.207 (d, J=6.9Hz, 1H), 7.289 (t, J=7.2Hz, 2H), 7.5–7.65 (m, 2H), 7.649 (s, 1H), 9.4 (bs, 1H). MS (m/z): 347, 254, 188, 91. Anal., Calcd. for C$_{21}$H$_{25}$BrF$_3$N: C, 58.88; H, 5.88; N, 3.27; Found: C, 58.49; H, 5.90; N, 3.46.

EXAMPLE 58

Preparation of 4-tert-butoxycarbonyl aminophenethyl alcohol

To a solution of 4-aminophenethyl alcohol (1.0 g, 7.3 mmol) in THF (30 mL) was added di-tert-butyl dicarbonate (2.0 g, 9.5 mmol) and the resulting solution was stirred at 25° C. for 24h; then the solution was concentrated under vacuum and purified by filtration on silica gel using ethyl acetate/n-hexane as eluant to afford the title compound as a white solid (1.63 g, 94%). m.p. 108° C. $^1$H NMR (CDCl$_3$): 1.513 (s, 9H), 2.813 (t, J=6.6Hz, 2H), 3.817 (d, J=5.1Hz, 2H), 6.47 (bs, 1H), 7.145 (d, J=8.4Hz, 2H), 7.30 (d, J=8.1 Hz, 2H).

EXAMPLE 59

Preparation of 1-p-toluenesulfonate-2-(4-tertbutoxycarbonylaminophenyl)ethane To a solution of 4-tert-butoxycarbonylaminophenethyl alcohol (1.56 g, 6.57 mmol) in CH$_2$Cl$_2$ (50 mL) were added Et$_3$N (1.8 mL, 13.0 mmol) and dropwise a solution of p-toluenesulfonyl chloride (1.63 g, 8.54 mmol) in CH$_2$Cl$_2$ (30 mL). The resulting solution was stirred at 25° C. for 3 h then diluted with CH$_2$Cl$_2$ (50 mL) and washed with HCl 5% (2×100 mL), brine (100 mL), dried and concentrated in vacuum. The crude compound was purified by flash-chromatography on silica gel using EtOAc/n-hexane as eluant to afford the title compound as a white solid (1.95 g, 76%). m.p. 102–104° C. $^1$H NMR (CDCl$_3$): 1.514 (s, 9H), 2.429 (s, 3H), 2.889 (t, J=7.2Hz, 2H), 4.162 (t, J=7.2Hz, 2H), 6.438 (bs, 1H), 7.012 (d, J=8.4Hz, 2H), 7.232 (d, J=8.4Hz, 2H), 7.28 (d, J=8.7Hz, 2H), 7.68 (d, J=8.1Hz, 2H).

EXAMPLE 60

Preparation of 3-benzyl-1-[2-(4-tertbutoxycarbonylaminophenyl)ethyl] piperidine From 3-benzylpiperidine hydrochloride (0.44 g, 2.08 mmol), 1-p-toluenesulfonate-2-(4-tertbutoxycarbonyl aminophenyl) ethane (1.06 g, 2.7 mmol) and potassium carbonate (0.56 g, 4.16 mmol) there was obtained the title compound as a foam (0.67 g, 82%); $^1$H NMR (CDCl$_3$): 0.85–1.02 (m, 1H), 1.50 (s, 9H), 1.4–1.6 (m, 1H), 1.62–1.80 (m, 3H), 1.82–2.02 (m, 2H), 2.45–2.60 (m, 4H), 2.65–2.80 (m, 2H), 2.80–3.0 (m, 2H), 6.405 (bs, 1H), 7.05–7.35 (m, 9H).

EXAMPLE 61

Preparation of 3-benzyl-1-[2-(4-aminophenyl)ethyl] piperidine hydrobromide 3-benzyl-1-[2-(4-tert-butoxycarbonylaminophenyl) ethyl]piperidine (0.67 g, 1.69 mmol) was dissolved in HBr (saturated solution in methanol, 10 mL) and the resulting solution stirred at 25° C. for 20 h. Then, after concentration in vacuum, the resultant mixture was treated with NaHCO$_3$ (water saturated solution, 50 mL) and extracted twice with EtOAc (2×50 mL). The collected organic phase was washed with brine (50 mL), dried and concentrated in vacuum. The crude compound was purified by filtration on silica gel using CH$_2$Cl$_2$/MeOH as eluant to afford the free amine as a pale yellow oil (0.272 g, 55%). $^1$H NMR (CDCl$_3$): 0.85–1.05 (m, 1H), 1.5–1.9 (m, 4H), 1.9–2.1 (m, 2H), 2.4–2.6 (m, 4H), 2.65–2.8 (m, 2H), 2.85–3.05 (m, 2H), 3.53 (bs, 2H), 6.61 (d, J=8.1Hz, 2H), 6.97 (d, J=8.1 Hz, 2H), 7.145 (d, J=7.8Hz, 2H), 7.18 (d, J=7.2, 1H), 7.275 (t, J-7.2Hz, 2H).

The HBr salt was obtained as a solid (0.3 g, 75%). m.p. dec. 1480C. $^1$H-NMR (DMSO): 1.0–1.2 (m, 1H), 1.55–1.7 (m, 2H), 1.7–1.9 (m, 1H), 1.95–2.2 (m, 1H), 2.4–2.6 (m, 2H), 2.55–2.75 (m, 1H), 2.75–2.9 (m, 1H), 2.9–3.1 (m, 2H), 3.15–3.3 (m, 2H), 3.3–3.8 (m, 3H), 7.1–7.4 (m, 9H), 9.45 (bs, 1H). Anal. Calcd. for C$_{20}$H$_{28}$Br$_2$N$_2$: C, 52.65; H, 6.19; N, 6.14; Found: C, 50.62; H, 6.07; N, 5.89.

EXAMPLE 62

Preparation of 1-p-toluenesulfonate-2-(4-chlorophenyl)ethane

From 4-chlorophenethyl alcohol (2.0 mL, 14.8 mmol), Et$_3$N (4.1 mL, 30.0 mmol) and p-toluenesulfonyl chloride (4.2 g, 22.2 mmol) there was obtained the title compound as a white solid (2.8 g, 61%). 77–79° C. $^1$H NMR (CDCl$_3$): 2.439 (s, 3H), 2.909 (t, J=6.6 Hz, 2H), 4.191 (t, J=6.6 Hz, 2H), 7.016 (d, J=8.1 Hz, 2H), 7.19 (d, J=8.4 Hz, 2H), 7.27 (d, J=7.2 Hz, 2H), 7.645 (d, J=8.1 Hz, 2H).

EXAMPLE 63

Preparation of 3-benzyl-1-[2-(4-chlorophenyl)ethyl] piperidine hydrobromide

From 3-benzylpiperidine hydrochloride (0.40 g, 1.89 mmol), 1-p-toluenesulfonate-2(4-chlorophenyl)ethane (0.76 g, 2.46 mmol) and potassium carbonate (0.52 g, 4.72 mmol) there was obtained the free base as an oil (0.314 g, 54%). $^1$H NMR (CDCl$_3$): 0.85–1.05 (m, 1H), 1.45–1.65 (m, 1H), 1.6–1.8 (m, 3H), 1.8–2.0 (m, 2H), 2.4–2.6 (m, 4H), 2.7–3.0 (m, 4H), 7.06–7.32 (m, 9H).

The HBr salt was obtained as as a white solid; m.p. 143–145° C. $^1$H NMR (DMSO): 1.0–1.2 (m, 1H), 1.5–1.7 (m, 2H), 1.75–1.9 (m, 1H), 1.9–2.1 (m, 1H), 2.45–2.55 (m, 1H), 2.6–3.0 (m, 4H), 3.1–3.3 (m, 3H), 3.3–3.43 (m, 1H), 3.505 (d, J=11.7Hz, 1H), 7.146 (d, J=7.5Hz, 2H), 7.18–7.33 (m, 5H), 7.36 (d, J=8.4Hz, 2H), 9.3 (bs, 1H). MS (m/z): 313, 188, 91. Anal. Calcd. for C$_{20}$H$_{25}$BrClN: C, 60.8; H, 6.1; N, 3.5; Found: C, 60.15; H, 6.61; N, 3.35.

EXAMPLE 64

Preparation of 1-p-toluenesulfonate-2-(4-fluorophenyl)ethane

From 4-fluorophenethyl alcohol (1.85 mL, 14.8 mmol), Et$_3$N (4.1 mL, 30 mmol) and p-toluenesulfonyl chloride (4.2 g, 22.16 mmol) there was obtained the title compound as an oil (3.1 g, 71%). $^1$H NMR (CDCl$_3$): 2.434 (s, 3H), 2.919 (t, J=6.9Hz, 2H), 4.186 (t, J=6.9Hz, 2H), 6.921 (t, J=8.5Hz, 2H), 7.06 (dd, J=8.4 and 5.4, 2H), 7.28 (d, J=8.4Hz, 2H), 7.67 (d, J=8.1Hz, 2H).

EXAMPLE 65

Preparation of 3-benzyl-1-[2-(4-fluorophenyl)ethyl] piperidine hydrobromide

From 3-benzylpiperidine hydrochloride (0.4 g, 1.89 mmol), 1-p-toluenesulfonate-2-(4-fluorophenyl)ethane (0.723 g, 2.46 mmol) and potassium carbonate (0.52 g, 4.73 mmol) there was obtained the free amine as an oil (0.385 g, 67%). 1H NMR (CDCl$_3$): 0.85–1.1 (m, 1H), 1.45–1.65 (m, 1H), 1.6–1.8 (m, 3H), 1.8–2.0 (m, 2H), 2.4–2.6 (m, 1H), 2.65–2.8 (m, 2H), 2.8–3.0 (m, 2H), 6.944 (t, J=8.7Hz, 2H), 7.05–7.23 (m, 5H), 7.273 (t, J=7.2Hz, 2H).

The HBr salt was obtained as a solid (0.45 g, 93%). m.p. 137–140° C. $^1$H NMR (DMSO): 1.0–1.2 (m, 1H), 1.5–1.7 (m, 2H), 1.75–1.9 (m, 1H), 1.9–2.1 (m, 1H), 2.45–2.6 (m, 2H), 2.6–2.72 (m, 1H), 2.73–2.9 (m, 1H), 2.9–3.05 (m, 2H), 3.15–3.3 (m, 2H), 3.45–3.6 (m, 1H), 7.08–7.32 (m, 9H), 9.4 (bs, 1H). Anal., Calcd. for C$_{20}$H$_{25}$BrFN: C, 63.49; H, 6.66; N, 3.70; Found: C, 63.11; H, 6.79; N, 3.81.

EXAMPLE 66

Preparation of 1-p-toluenesulfonate-2-(4-methoxyphenyl)ethane

From 4-methoxyphenethyl alcohol (2.0 g, 13.1 mmol), Et$_3$N (3.67 mL, 26.3 mmol) and p-toluenesulfonyl chloride (3.75 g, 19.7 mmol) there was obtained the title compound as a white solid (1.6 g, 40%). $^1$H NMR (CDCl$_3$): 2.432 (s, 3H), 2.890 (t, J=6.9Hz, 2H), 3.78 (s, 3H), 4.163 (t, J=6.9Hz, 2H), 6.78 (d, J=8.4Hz, 2H), 7.022 (d, J=8.4Hz, 2H), 7.281 (d, J=8.1Hz, 2H), 7.691 (d, J=8.1Hz, 2H).

EXAMPLE 67

Preparation of 3-benzyl-1-[2-(4-methoxyphenyl) ethyl]piperidine hydrobromide

From 3-benzylpiperidine hydrochloride (0.4 g, 1.89 mmol), 1-p-toluenesulfonate-2-(4-methoxyphenyl)ethane (0.75 g, 2.46 mmol) there was obtained the free amine as an oil (0.4 g, 68%). $^1$H NMR (CDCl$_3$): 0.85–1.1 (m, 1H), 1.5–1.65 (m, 1H), 1.6–1.8 (m, 3H), 1.85–2.0 (m, 2H), 2.4–2.6 (m, 4H), 2.65–2.8 (m, 2H), 2.8–3.0 (m, 2H), 3.781 (s, 3H), 6.816 (d, J=8.4Hz, 2H), 7.095 (d, J=8.0Hz, 2H), 7.146 (d, J=7.2Hz, 2H), 7.195 (d, J=7.2Hz, 1H), 7.274 (t, J=7.2Hz, 2H).

The HBr salt was obtained as a solid (0.22 g, 46%). m.p. 74–78° C. $^1$H NMR (DMSO): 0.95–1.2 (m, 1H), 1.55–1.73 (m, 2H), 1.75–1.87 (m, 1H), 1.95–2.1 (m, 1H), 2.4–2.6 (m, 3H), 2.6–2.75 (m, 1H), 2.75–3.0 (m, 3H), 3.1–3.25 (m, 1H), 3.45–3.55 (m, 1H), 3.687 (s, 3H), 6.853 (d, J=8.4Hz, 2H), 7.1–7.24 (m, 5H), 7.283 (t, J=6.9Hz, 2H), 9.3 (bs, 1H). MS (m/z): 310, 309, 188, 91.

EXAMPLE 68

3-Benzyl-1-(3-phenylpropyl)piperidine hydrobromide.

From 3-benzylpiperidine (500 mg, 2.36 mmol) and 3-phenylpropyl bromide (705 mg, 3.54 mmol) there was obtained a clear amber oil (315 mg, 46%) (Carter. P. A.; Singh, S. Eur. Pat. Appl. 435387, Jul. 3, 1991): $^1$H NMR (CDCl$_3$) d 0.86–1.00 (m, 1 H), 1.44–1.95 (m, 8 H), 2.25–2.64 (m, 6 H), 2.75–2.89 (m, 2 H), 7.10–7.31 (m, 10 H); The hydrobromide was obtained as a beige solid (297 mg, 94%): mp 134–136° C.; Recrystallization (2-butanone/ether) gives a colorless solid, mp 140–141.5° C. Anal. Calcd for C$_{21}$H$_{28}$BrN: C, 67.38; H, 7.54; N,3.74. Found: C, 67.26; H, 7.69; N, 3.72.

EXAMPLE 69

Preparation of 1-benzyl-3-phenyl-3-hydroxypiperidine

To a solution of 1-benzyl-3-piperidinone (0.193 g, 1.02 mmol) in toluene dry (10 mL) cooled at 0° C. was added a solution of phenyl magnesium bromide 3.0 M in THF (0.48 mL, 1.4 mmol). The resulting solution was maintained at 0° C. for 2 h, then was allowed to warm at 25° C. for 1 h. Water (50 mL) was added and the mixture was extracted with EtOAc (2×50 mL). The collected organic phase was dried and concentrated under reduced pressure. The crude compound was purified by flash chromatography on silica gel using EtOAc/cyclohexane as eluant to afford the title compound as a white solid (0.235 g, 80%). $^1$H NMR (CDCl$_3$): 1.65–1.85 (m, 3H), 1.9–2.15 (m, 1H), 2.067 (bd, J=8.1Hz, 1H), 2.34 (d, J=11.1 Hz, 1H), 2.77 (d, J=11.1 Hz, 1H), 2.95 (bd, J=8.1Hz, 1H), 3.60 (s, 2H), 4.005 (bs, 1H), 7.2–7.4 (m, 8H), 7.50 (s, 1H), 7.525 (s, 1H).

EXAMPLE 70

Preparation of 3-phenyl-3-hydroxypiperidine hydrobromide

To a solution of 1-benzyl-3-phenyl-3-hydroxypiperidine (0.95 g, 3.5 mmol) in ethanol (15 mL) was added Pd/C 10% (0.3 g). This heterogeneous solution was hydrogenated at 1 atm at 25° C. and for 40 h then filtered through a celite pad and concentrated under reduced pressure. The crude compound was dissolved in MeOH (10 mL) and treated with a diluted solution of HBr in MeOH (1.2M, 5 mL). This solution was stirred at 25° C. for 5 min. then the solvent was removed under vacuum to give an oil. Acetone was added (15 mL) and the mixture was vigorously stirred for 2 h to give a white suspension. The solid was collected, washed with acetone (2×4 mL) and dried under vacuum to afford the title compound as a white solid (0.43 g, 47%). m.p. 168–170° C. $^1$H NMR (DMSO): 1.699 (t, J=9.2Hz, 2H), 1.95–2.05 (m, 2H), 2.9–3.0 (d, J 12.3Hz, 2H), 3.07–3.29 (m, 3H), 7.26 (t, J=7.2Hz, 1H), 7.353 (m, 2H), 7.50 (d, J=7.5Hz, 2H), 8.55(bs, 2H).

EXAMPLE 71

Preparation of 3-phenyl-3-hydroxy-1-(2-phenylethyl)piperidine hydrobromide

From 3-phenyl-3-hydroxypiperidine hydrobromide (0.2 g, 0.77 mmol), 2-bromoethylbenzene (0.138 mL, 1.0 mmol) and potassium carbonate (0.267 g, 1.9 mmol) there was obtained the free amine as an oil (0.15 g, 70%). $^1$H NMR (CDCl$_3$): 1.6–1.85 (m, 3H), 1.9–2.05 (m, 1H), 2.156 (bt, J=11.7Hz, 1H), 2.39 (d, J=11.1 Hz, 1H), 2.6–2.9 (m, 5H), 3.02 (bd, J=10.5Hz, 1H), 3.92 (bs, 1H), 7.15–7.40 (m, 8H), 7.53 (d, J=7.5Hz, 2H)

The HBr salt was obtained as a brown solid; m.p. 159–161° C. $^1$H-NMR (DMSO): 1.788 (t, J=12.9Hz, 2H), 1.94–2.06 (m, 1H), 2.06–2.2 (m, 1H), 2.85–3.0 (m, 1H), 3.0–3.15 (m, 2H), 3.15–3.27 (m, 2H), 3.27–3.5 (m, 3H), 7.2–7.34 (m, 6H), 7.38 (t, J=7.5Hz, 2H), 7.525 (d, J=7.5Hz, 2H). Anal. Calcd. for C$_{19}$H$_{24}$BrNO: C, 63.0; H, 6.67; N, 3.87. Found: C, 62.89; H, 6.81; N, 3.83.

EXAMPLE 72

Preparation of 3-phenyl-3-hydroxy-1-(3-phenylpropyl)piperidine hydrobromide

From 3-phenyl-3-hydroxypiperidine hydrobromide (0.2 g, 0.77 mmol), 1-bromo-3-phenylpropane (0.153 mL, 1.0 mmol) and potassium carbonate (0.267 g, 1.9 mmol) there was obtained the free amine as an oil (0.127 g, 56%). $^1$H NMR (CDCl$_3$): 1.65–1.90 (m, 5H), 1.9–2.1 (m, 2H), 2.286 (d, J=11.1 Hz, 1H), 2.35–2.55 (m, 2H), 2.652 (t, J=7.8Hz, 2H), 2.754 (bd, J=10.8Hz, 1H), 2.95 (bd, J=7.5Hz, 1H), 7.14–7.32 (m, 6H), 7.356 (t, J=7.2Hz, 2H), 7.52 (d, J=7.5Hz, 2H).

The HBr salt was obtained as a brown solid m.p. 166–170° C. $^1$H NMR (DMSO): 1.74 (t, J=11.5Hz, 2H), 1.83–2.2 (m, 4H), 2.555 (t, J=7.5Hz, 2H), 2.9–3.1 (m, 3H), 3.15–3.3 (m, 2H), 5.85 (s, 1H), 7.1–7.3 (m, 6H), 7.36 (t, J=7.5Hz, 2H), 7.49 (d, J=7.5Hz, 2H), 9.01 (bs, 1H). Anal. Calcd. for C$_{20}$H$_{26}$BrNO: C, 63.8; H, 6.67; N, 3.7. Found: C, 62.89; H, 6.89; N, 3.65.

EXAMPLE 73

Preparation of N-acetylisonipecotic acid

Isonipecotic acid (25.0 g, 0.19 mol) was dissolved in acetic anhydride (100 mL) and the solution stirred at reflux for 8 h, then the solvent was removed under reduced pressure and the crude compound crystallized from MeOH/ether to afford the title compound as a white solid (24.4 g, 74%). m.p. 171° C. $^1$H NMR (DMSO): 1.2–1.5 (m, 2H), 1.65–1.85 (m, 2H), 1.942 (s, 3H), 2.35–2.5 (m, 1H), 2.641 (t, J=11.7Hz, 1H), 3.038 (t, J=11.7Hz, 1H), 3.69 (d, J=13.5Hz, 1H), 4.15 (d, J=13.2Hz, 1H), 12.22 (bs, 1H). IR (KBr): 1721, 1613, 1316, 1202 (cm$^{-1}$). MS (m/z): 171, 128, 82.

EXAMPLE 74

Preparation of N-acetylisonipecotic acid chloride

N-acetylisonipecotic acid (0.67 g, 3.9 mmol) was added to SOCl$_2$ (4.1 mL). The acid chloride precipitated from solution and petrol (60 mL) was added. The mixture was filtered and the residue was washed several times with petrol to afford the title compound as a white solid (0.716 g, 97%). m.p. 133–138° C. $^1$H NMR (DMSO): 1.2–1.5 (m, 2H), 1.65–2.0 (m, 2H), 1.94 (s, 3H), 2.3–2.5 (m, 1H), 2.639 (t, J=11.4Hz, 1H), 3.036 (t, J=11.4Hz, 1H), 3.692 (d, J=13.2Hz, 1H), 4.144 (d, J=13.2Hz, 1H). IR (KBr): 1789, 1745, 1660 (cm$^{-1}$). MS (m/z): 189, 126, 146, 84.

EXAMPLE 75

Preparation of 4-(p-fluorobenzoyl)-1-acetylpiperidine

N-acetyl-isonipecotic acid chloride (2.0 g, 10.5 mmol) was slowly added to a stirring mixture of aluminum trichloride (2.8 g, 21.1 mmol) in fluorobenzene (10 mL). After the addition was completed, the mixture was refluxed for 1 h. The mixture was poured into ice and the resulting layers were separated. The aqueous layer was extracted twice with CH$_2$Cl$_2$ (2×30 mL) and the combined organic phase was dried and concentrated under reduced pressure to afford the title compound as an oil (1.3 g, 50%). $^1$H NMR (CDCl$_3$): 1.5–1.7 (m, 1H), 1.7–2.0 (m, 3H), 2.104 (s, 3H), 2.813 (t, J=12.0Hz, 1H), 3.15–3.3 (m, 1H), 3.4–3.55 (m, 1H), 3.902 (d, J=13.2Hz, 1H), 4.574 (d, J=13.2Hz, 1H), 7.145 (t, J=8.4Hz, 2H), 7.967 (dd, J=5.7 & 8.4Hz, 2H).

EXAMPLE 76

Preparation of 4-(p-fluorobenzoyl) piperidine hydrobromide

A solution of 4-(p-fluorobenzoyl)-1-acetylpiperidine (1.2 g, 4.8 mmol) in HCl 6N (15 mL) was refluxed for 2 h. The cooled solution was made basic (NaOH) and then extracted with benzene (2×40 mL). The collected organic phase was washed with brine (50 mL), dried and concentrated under reduced pressure. The free amine was dissolved in HBr (saturated solution in methanol, 10 mL) and the hydrobromic salt precipitated was collected, washed with ether (2×4 mL) and dried under vacuum to afford the title compound as a white solid (1.54 g, 98%). m.p. 198° C. $^1$H NMR (CD$_3$OD): 1.8–2.0 (m, 2H), 2.05–2.18 (m, 2H), 3.12–3.28 (m, 2H), 3.4–3.5 (m, 2H), 3.7–3.85 (m, 1H), 4.856 (s, 2H), 7.243 (t, J=8.3Hz, 2H), 8.099 (dd, J=5.7 & 8.7Hz, 2H).

EXAMPLE 77

Preparation of 4-(p-fluorobenzoyl)-1-(3-hydroxypropyl)piperidine

To a solution of 4-(p-fluorobenzoyl)piperidine hydrobromide (0.3 g, 1.04 mmol) in DMF (10 mL) were added 3-bromo-1-propanol (0.11 mL, 1.25 mmol) and potassium carbonate (0.29 g, 2.08 mmol). This heterogeneous solution was heated at 110° C. for 3 h then cooled at 25° C., diluted with water (100 mL) and extracted with EtOAc (3×30 mL). The collected organic phase was washed with water (2×50 mL), dried and concentrated in vacuum. The crude compound was purified by filtration on silica gel using CH$_2$Cl$_2$/MeOH as eluant to afford the title compound as a pale yellow solid (0.13 g, 47%). m.p.=106–108° C. $^1$H NMR (CDCl$_3$): 1.55–1.68 (m, 2H), 1.68–1.95 (m, 5H), 2.05–2.2 (m, 2H), 2.642 (t, J=5.4Hz, 2H), 3.13 (bd, J=11.7Hz, 2H), 3.15–3.3 (m, 1H), 3.808 (t, J=4.8Hz, 2H), 7.137 (t, J=8.4Hz, 2H), 7.95 (dd, J=5.4 & 8.4, 2H). Anal. Calcd. for C$_{15}$H$_{20}$FNO$_2$:C, 67.90; H, 7.60; N, 5.28; Found: C, 66.71; H, 7.38; N, 5.44.

EXAMPLE 78

1-(3-Hydroxypropyl)-4-(4-methoxybenzoyl) piperidine

A) 1-Acetyl-4-(4-methoxybenzoyl)piperidine

To a suspension of aluminum trichloride (3.40 g, 25.7 mmol) in CS$_2$ (15 mL) were added anisole (1.90 mL, 17.6 mmol) and, portionwise, N-acetylisonipecotoyl chloride (2.40 g, 11.7 mmol). After the addition was complete, the mixture was refluxed for 1 h. The solvent was decanted and the red residue was dissolved in 5% HCl (50 mL) and was extracted with EtOAc (4×30 mL). The combined organic phase was dried and was concentrated under reduced pressure to afford the title compound as a colorless solid (1.8 g, 60%): mp 102–105° C.; $^1$H NMR (CDCl$_3$) d 1.50–1.75 (m, 1H), 1.70–2.00 (m, 3H), 2.10 (s, 3H), 2.70–2.90 (m, 1H), 3.15–3.30 (m, 1H), 3.40–3.53 (m, 1H), 3.86 (s, 3H), 3.85–4.00 (m, 1H), 4.56 (d, J=13.2 Hz, 1H), 6.94 (d, J=8.7 Hz, 2H), 7.92 (d, J=9.0 Hz, 2H).

B) 4-(4-Methoxybenzoyl)piperidine

This compound was prepared in a manner similar to example 76. From 1-acetyl-4-(4-methoxybenzoyl) piperidine (1.80 g, 6.90 mmol) and 6 N HCl (10 mL) there was obtained the hydrobromide salt as a colorless solid (1.65 g, 80%-0): mp 230–233° C.; $^1$H NMR (DMSO-d6) d 1.60–1.80 (m, 2H), 1.87 (bd, J=13.2 Hz, 2H), 3.03 (t, J=10.5 Hz, 2H), 3.29 (d, J=12.6 Hz, 2H), 3.65–3.80 (m, 1H), 3.84 (s, 3H), 7.02 (d, J=8.4 Hz, 2H), 7.97 (d, J=8.4 Hz, 2H), 8.54 (bs, 2H).

C) 1-(3-Hydroxypropyl)-4-(4-methoxybenzoyl) piperidine

This compound was prepared in a manner similar to example 77. From 4-(4-methoxybenzoyl)piperidine hydrobromide (0.60 g, 2.0 mmol) and 3-bromo-1-propanol (0.28 mL, 3.0 mmol) there was obtained the hydrobromide salt as a colorless solid (0.38 g, 53%) mp 148–151° C.; $^1$H NMR (DMSO-d$_6$) d 1.70–1.88 (m, 4H), 1.90–2.03 (m, 2H), 2.98–3.20 (m, 4H), 3.45 (t, J=5.4 Hz, 2H), 3.54 (bd, J=12.0 Hz, 2H), 3.60–3.75 (m, 1H), 3.81 (s, 3H), 4.75 (bs, 1H), 7.04 (d, J=8.4 Hz, 2H), 7.96 (d, J=8.4 Hz, 2H), 9.1 (bs, 1H); MS (m/z): 277, 232, 114.

EXAMPLE 79

4-(2-Hydroxybenzoyl)-1-(3-hydroxypropyl) piperidine

A) Phenyl N-acetylisonipecotate

To a suspension of N-acetylisonipecotoyl chloride (3.70 g, 19.50 mmol) in THF (60 mL) were added phenol (2.70 g, 27 mmol) and Et$_3$N (5.0 mL, 36 mmol). The resulting heterogeneous mixture was stirred at 25° C. for 20 h, diluted with EtOAc (50 mL) and was washed with a saturated solution of NH$_4$Cl (50 mL). The crude compound was purified by filtration on silica gel using EtOAc/n-hexane as eluant to afford the title compound as a colorless solid (3.45 g, 80%): mp 96–98 C; $^1$H NMR (CDCl$_3$) d 1.60–1.95 (m, 2H), 2.00–2.2 (m, 5H), 2.70–3.00 (m, 2H), 3.10–3.30 (m, 1H), 3.75–3.90 (m, 1H), 4.40–4.60 (m, 1H), 7.06 (d, J=7.5 Hz, 2H), 7.22 (d, J=7.5 Hz, 1H), 7.38 (t, J=7.5 Hz, 2H).

B) 4-(2- and 4-Hydroxybenzoyl)-1-acetyl piperidine

To a solution of phenyl N-acetylisonipecotate (3.40 g, 13.7 mmol) in 4-nitrobenzene (16 mL) was added portionwise AlCl$_3$ (3.70 g, 27.5 mmol). The resulting solution was heated at 60° C. for 4 h, diluted with 6 M HCl (40 mL) and was washed with ether (3×50 mL). The aqueous solution was neutralized with NaOH and was extracted with EtOAc (4×50 mL). The collected organic phase was washed with a saturated solution of NH$_4$Cl (50 mL), dried and was concentrated under reduced pressure to afford a mixture of isomers as a solid (2.32 g, 70%, The 4-isomer was the major product as shown by $^1$H NMR): $^1$H NMR (4-isomer, DMSO-d$_6$) d 1.20–1.38 (m, $^1$H), 1.38–1.60 (m, $^1$H), 1.65–1.80 (m, 2H), 1.96 (s, 3H), 2.66 (t, J=12.0 Hz, $^1$H), 3.14 (t, J=12.6 Hz, 1H), 3.50–3.65 (m, 1H), 3.80 (bd, J=13.2 Hz, 1H), 4.35 (bd, J=12.6 Hz, 1H), 6.82 (d, J=8.7 Hz, 2H), 7.85 (d, J=8.4 Hz, 2H).

C) 4-(2-Hydroxybenzoyl)piperidine hydrobromide

An solution of 4-(2- and 4-hydroxybenzoyl)-1-acetyl piperidine (2.30 g, 9.30 mmol) in 6 N HCl (20 mL) was refluxed for 2 h. The cooled solution was extracted with ether (2×30 mL), made basic (NaOH) and was extracted with EtOAc (2×30 mL). An insoluble solid formed which was removed. The EtOAc portion was dried and was concentrated under reduced pressure. The free amine was dissolved in HBr (saturated solution in methanol, 5 mL) and the precipitated hydrobromide salt was collected, washed with ether (2×4 mL) and was dried in vacuo to afford the title compound as a colorless solid (0.26 g): mp 253° C. (dec); $^1$H NMR (DMSO-d₆) d 1.60–1.83 (m, 2H), 1.94 (bd, J=12.9 Hz, 2H), 2.90–3.10 (m, 2H), 3.30 (bd, J=12.3 Hz, 2H), 3.65–3.90 (m, 1H), 6.94 (t, J=8.7 Hz, 2H), 7.50 (t, J=7.5 Hz, 1H), 7.88 (d, J=7.5 Hz, 1H), 8.33 (bs, 1H), 8.58 (bs, 1H), 11.63 (s, 1H).

D) 4-(2-Hydroxybenzoyl)-1-(3-hydroxypropyl) piperidine

This compound was prepared in a manner similar to example 77. From 4-(2-hydroxybenzoyl) piperidine hydrobromide (0.26 g, 0.87 mmol) and 3-bromo-1-propanol (0.08 mL, 0.9 mmol) there was obtained the title compound as a brown solid (0.10 g, 43%): mp 77–80° C.; ¹H NMR (DMSO-d₆) d 1.65–1.78 (m, 2H), 1.80–1.90 (m, 4H), 2.00–2.20 (m, 2H), 2.62 (t, J=5.4 Hz, 2H), 3.14 (d, J=11.4 Hz, 2H), 3.20–3.40 (m, 1H), 3.78 (t, J=5.1 Hz, 2H), 4.80 (bs, 1H), 6.88 (t, J=7.5 Hz, 1H), 6.97 (d, J=8.4 Hz, 1H), 7.45 (t, J=8.1 Hz, 1H), 7.73 (d, J=7.8 Hz, 1H), 12.42 (bs, 1H). MS (m/z) 263, 218, 114, 70.

EXAMPLE 80

4-(4-Fluorobenzoyl)-1-(2-(4-fluorophenoxy)ethyl) piperidine hydrochloride

The compound was prepared in a manner similar to example 77. From 4-(4-fluorobenzoyl)piperidine hydrobromide (1.5 g, 6.1 mmol) and 2-(4-fluorophenoxy)ethyl bromide (2.0 g, 9.2 mmol) there was obtained the free amine as a brown solid (1.0 g, 50%): mp 88–91C; ¹H NMR (CDCl₃) d 1.80–1.95 (m, 4H), 2.20–2.35 (m, 2H), 2.82 (t, J=6.0Hz, 2H), 3.07 (bd, J=11.4Hz, 2H), 3.15–3.30 (m, 1H), 4.07 (t, J=5.7Hz, 2H), 6.80–6.90 (m, 2H), 6.96 (t, J=8.7Hz, 2H), 7.13 (t, J=8.4Hz, 2H), 7.96 (dd, J=5.7 and 8.4Hz, 2H). The HCl salt was obtained as a brown solid (0.17 g, 54%): mp 138–141° C.; HRMS calcd for C₂₀H₂₁F₂NO₂ 345.1540, found 345.1547.

EXAMPLE 81

4-((4-Fluorophenyl)hydroxymethyl)-1-(2-(4-fluorophenoxy)ethyl)piperidine hydrochloride A solution of 4-(4-fluorobenzoyl)-1-(2-(4-fluorophenoxy)ethyl) piperidine (0.77 g, 2.22 mmol) in THF (10 mL) was added dropwise manner to a suspension of LiAlH₄ (0.42 g, 11 mmol) in THF (10 mL). The mixture was heated at reflux for 5 h. Excess hydride was decomposed with a saturated solution of Na₂SO₄. The inorganic precipitate was removed by filtration, the filtrate was dried over Na₂SO₄ and was concentrated under reduced pressure. The crude compound was dissolved in a saturated solution of HCl in MeOH (5 mL) and the resulting solution was stirred at 25° C. for 5 min. After concentration in vacuo, the resulting mixture was triturated with ether for 10 h to afford the title compound as a colorless solid (0.40 g, 52%): mp 71–75° C.; ¹H NMR (DMSO-d₆) d 1.20–1.50 (m, 3H), 1.50–1.70 (m, 1H), 1.80 (d, J=12.3 Hz, 1H), 2.45–2.65 (m, 2H), 3.00–3.15 (m, 2H), 3.20–3.35 (m, 2H), 4.10–4.20 (m, 2H), 4.28 (d, J=6.3 Hz, 1H), 6.93 (dd, J=4.2 and 8.7 Hz, 2H), 7.05–7.15 (m, 4H), 7.25–7.35 (m, 2H).

EXAMPLE 82

4-Benzyl-1-(2-hydroxyethyl)piperidine

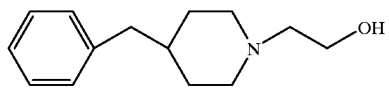

To a solution of 4-benzylpiperidine (0.50 mL, 2.8 mmol) in DMF (15 mL) were added 2-chloroethanol (0.25 mL, 3.70 mmol) and K₂CO₃ (0.79 g, 5.70 mmol). The heterogeneous mixture was heated at 110° C. for 2 h. It was then cooled to 25° C. and was diluted with water (100 mL) and extracted with ether (2×70 mL). The collected organic phase was washed with water (2×100 mL), dried and concentrated in vacuo. The crude compound was purified by filtration on silica gel using CH₂Cl₂/MeOH as eluant to afford the title compound as a colorless solid (0.25 g, 40%): mp 62–64° C.; ¹H NMR (CDCl₃) δ1.15–1.35 (m, 2H), 1.45–1.60 (m, 1H), 1.63 (bd, J=13.8 Hz, 2H), 1.99 (t, J=11.7 Hz, 2H), 2.48 (t, J=5.7 Hz, 2H), 2.53 (d, J=6.9 Hz, 2H), 2.87 (bd, J=11.7 Hz, 2H), 2.9 (bs, 1H), 3.574 (t, J=5.4 Hz, 2H), 7.14 (d, J=7.2 Hz, 2H), 7.20 (d, J=6.9 Hz, 1H), 7.28 (t, J=6.2 Hz, 2H); MS (m/z) 219, 188, 91. Anal. Calcd for C₁₄H₂₁NO: C, 76.71; H 9.65; N, 6.40. Found: C, 74.49; H 9.29; N, 6.08.

EXAMPLE 83

4-Benzyl-1-(3-hydroxypropyl)piperidine hydrobromide

This compound was prepared in a manner similar to example 82. From 4-benzyl piperidine (5.00 mL, 28.4 mmol) and 3-bromo-1-propanol (2.70 mL, 29.9 mmol) there was obtained the free amine as a colorless oil (6.25 g, 94%). ¹H NMR (CDCl₃) δ1.20–1.40 (m, 2H), 1.45–1.65 (m, 1H), 1.60–1.75 (m, 3H), 1.89 (t, J=11.1 Hz, 2H), 2.51 (d, J=6.9 Hz, 2H), 2.58 (t, J=5.7 Hz, 2H), 3.04 (bd, J=11.4 Hz, 2H), 3.80 (t, J=5.1 Hz, 2H), 7.12 (d, J=7.2 Hz, 2H), 7.19 (d, J=7.2 Hz, 1H), 7.27 (t, J=7.2 Hz, 2H).

The free amine (1.50 g) was dissolved in a solution of HBr in MeOH (1.0 M, 10 mL). The resulting solution was stirred at 25° C. for 10 min. and was concentrated in vacuo. The resulting crude product was triturated with acetone (10 mL) for 2 h to give the title compound as a colorless solid (1.2 g, 60%): mp 122–124° C.; ¹H NMR (DMSO-d₆) δ1.30–1.50 (m, 2H), 1.60–1.82 (m, 4H), 2.50 (d, J=6.6 Hz, 2H), 2.70–2.90 (m, 2H), 2.95–3.08 (m, 2H), 3.10–3.23 (m, 1H), 3.35–3.50 (m, 4H), 4.71 (bs, 1H), 7.10–7.20 (m, 3H), 7.27 (t, J=7.2 Hz, 2H), 9.00 (bs, 1H); Anal. Calcd for C₁₅H₂₄BrNO: C, 57.32; H 7.69; N, 4.46. Found: C, 57.46; H 7.74; N, 4.46.

EXAMPLE 84

4-Benzyl-1-(3-hydroxy-1-methylpropyl)piperidine

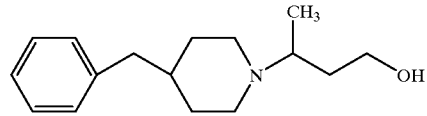

A) Ethyl 3-(4-benzylpiperidin-1-yl)butyrate

A solution of 4-benzyl piperidine (0.50 mL, 2.8 mmol) and ethyl crotonate (0.46 mL, 3.4 mmol) in isopropanol (10 mL) was refluxed for 24 h and was concentrated in vacuo. The crude compound was purified by filtration on silica gel using CH₂Cl₂/MeOH as solvent to afford the title compound as a pale yellow oil (0.64 g, 74%): ¹H NMR (CDCl₃) δ1.09 (d, J=6.6 Hz, 3H), 1.30 (t, J=6.9 Hz, 3H), 1.20–1.40 (m, 2H), 1.45–1.61 (m, 1H), 1.68 (bd, J=12.3 Hz, 2H), 2.10–2.35 (m, 3H), 2.57 (d, J=6.9 Hz, 2H), 2.50–2.70 (m, 1H), 2.82 (bd, J=10.8 Hz, 2H), 3.15–3.30 (m, 1H), 4.18 (q, J=6.9 Hz, 2H), 7.18 (d, J=7.2 Hz, 2H), 7.24 (m, 1H), 7.32 (t, J=6.9 Hz, 2H).

B) 4-Benzyl-1-(3-hydroxy-1-methylpropyl)piperidine

To a solution of ethyl 3-(4-benzylpiperidin-1-yl)butyrate (0.60 g, 2.0 mmol) in dry THF (10 mL) was added portionwise LiAlH$_4$ (0.15 g, 3.9 mmol). The resulting heterogeneous mixture was stirred at 25° C. for 2 h then quenched with MeOH. The resulting mixture was diluted with EtOAc (100 mL), washed with NH4Cl (100 mL) and brine (100 mL), dried and was concentrated under reduced pressure. The crude compound was purified by filtration on silica gel using CH$_2$Cl$_2$/MeOH as solvent to afford the title compound as a colorless solid (0.38 g, 80%): mp 74–76° C.; $^1$H NMR (CDCl$_3$) δ1.00 (d, J=6.6 Hz, 3H), 1.15–1.45 (m, 3H), 1.50–1.65 (m, 1H), 1.65–1.80 (m, 2H), 1.85–2.15 (m, 3H), 2.40–2.60 (m, 3H), 2.82 (bd, J=11.1 Hz, 1H), 2.90–3.10 (m, 2H), 3.80–4.00 (m, 2H), 6.55 (bs, 1H), 7.19 (t, J=7.2 Hz, 2H), 7.24 (d, J=6.9 Hz, 1H), 7.32 (t, J=7.2 Hz, 2H); MS (m/z) 247, 248, 232, 202, 91. Anal. Calcd for C$_{16}$H$_{25}$NO: C, 77.68, H 10.18; N, 5.66. Found C, 77.56; H 10.22; N, 5.63.

EXAMPLE 85

4-Benzyl-1-(2,3-dihydroxypropyl)piperidine

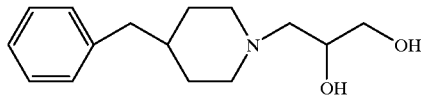

A) 2,2-Dimethyl-4-tosylmethyl-1,3-dioxolane

To a solution of solketal (2.00 mL, 16.0 mmol) in CH$_2$Cl$_2$ (50 mL) was added Et$_3$N (4.50 mL, 32 mmol). A solution of p-toluensulfonyl chloride (4.30 g, 22 mmol) in CH$_2$Cl$_2$ (30 mL) was then added dropwise at 0° C. The resulting solution was stirred at 25° C. for 6 h, then was diluted with CH$_2$Cl$_2$ (50 mL). This solution was washed with HCl (5w, 100 mL) and brine (100 mL), dried and concentrated in Vacuo to afford the crude product. This was purified by flash-chromatography on silica gel using EtOAc/n-hexane as eluant to give the title compound as a colorless oil (2.03 g, 45%): $^1$H NMR (CDCl$_3$) δ1.31 (s, 3H), 1.34 (s, 3H), 2.45 (s, 3H), 3.77 (q, J=5.1 and 8.7 Hz, 1H), 3.90–4.10 (m, 3H), 4.28 (p, J=5.7 Hz, 1H), 7.35 (d, J=8.1 Hz, 2H), 7.80 (d, J=8.1 Hz, 2H);

B) 4-(4-Benzylpiperidin-1-yl)-2,2-dimethyl-1,3-dioxolane

This compound was prepared in a manner similar to example 1. From 4-benzylpiperidine (1.00 mL, 5.70 mmol) and 2,2-dimethyl-4-tosylmethyl-1,3-dioxolane (2.00 g, 7.00 mmol) there was obtained the title compound as a yellow oil (0.95 g, 58%): $^1$H NMR (CDCl$_3$) δ1.33 (s, 3H), 1.39 (s, 3H), 1.10–1.40 (m, 2H), 1.40–1.57 (m, 1H), 1.59 (d, J=13.2 Hz, 2H), 1.85–2.05 (m, 2H), 2.39 (dd, J=5.1 and 12.9 Hz, 1H), 2.45–2.60 (m, 3H), 2.85 (d, J=11.1 Hz, 1H), 2.95 (bd, J=11.1 Hz, 1H), 3.56 (t, J=7.8 Hz, 1H), 4.04 (t, J=7.8 Hz, 1H), 4.20–4.30 (m, 1H), 7.12 (d, J=7.2 Hz, 2H), 7.18 (d, J=6.9 Hz, 1H), 7.26 (t, J=7.2 Hz, 2H).

C) 4-Benzyl-1-(2,3-dihydroxypropyl)piperidine

A solution of 4-(4-Benzyl-piperidin-1-yl)-2,2-dimethyl-1,3-dioxolane (0.65 g) in methanolic HBr (1.0 M, 20 mL) was prepared. The solution was stirred at 25° C. for 2 h then was concentrated in vacuo. The resulting crude product was dissolved in water (50 mL), washed with ether (20 mL), made basic with saturated NaHCO$_3$ (20 mL) and extracted with CH$_2$Cl$_2$ (3×30 mL). The crude compound was purified by trituration with EtOAc (5 mL) for 2 h to give the title compound as a colorless solid (0.45 g, 80%): mp 92–94° C.; $^1$H NMR (CDCl$_3$) δ1.15–1.40 (m, 2H), 1.45–1.65 (m, 1H), 1.64 (bd, J=13.5 Hz, 2H), 1.92 (t, J=11.4 Hz, 1H), 2.20 (t, J=11.4 Hz, 1H), 2.30 (dd, J=3.9 and 12.3 Hz, 1H), 2.45–2.60 (m, 3H), 2.81 (bd, J=11.4 Hz, 1H), 2.98 (bd, J=11.1 Hz, 1H), 3.65–3.85 (m, 2H), 7.14 (d, J=7.2 Hz, 2H), 7.20 (d, J=6.9 Hz, 1H), 7.28 (t, J=7.2 Hz, 2H; MS (m/z) 249, 232, 218, 188, 91. Anal. Calcd for C$_{15}$H$_{23}$NO$_2$: C, 72.25; H 9.30; N, 5.62. Found C, 72.19; H 9.43; N, 5.75.

EXAMPLE 86

4-Benzyl-1-(4-hydroxybutyl)piperidine hydrobromide

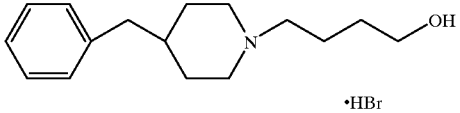

A) Ethyl 4-(4-benzylpiperidin-1-yl)butyrate hydrobromide

This compound was prepared in a manner similar to example 82. From 4-benzylpiperidine (1.00 mL, 5.70 mmol) and ethyl 4-bromobutyrate (0.90 mL, 6.3 mmol) there was obtained the free amine as a pale yellow oil (1.25 g, 76%). $^1$H NMR (CDCl$_3$) δ1.24 (t, J=7.2 Hz, 3H), 1.26–1.40 (m, 2H), 1.45–1.60 (m, 1H), 1.63 (bd, J=12.9 Hz, 2H), 1.75–1.95 (m, 4H), 2.25–2.40 (m, 4H), 2.53 (d, J=6.9 Hz, 2H), 2.90 (bd, J=11.4 Hz, 2H), 4.11 (q, J=7.2 Hz, 2H), 7.13 (bd, J=7.2 Hz, 2H), 7.19 (d, J=6.9 Hz, 1H), 7.27 (t, J=7.2 Hz, 2H).

The free amine (0.10 g) was dissolved in HBr (1.0 M in MeOH, 5 mL). The resulting solution was stirred at 25° C. for 10 min. and was concentrated in vacuo. The crude product was triturated with acetone (10 mL) for 2 h to give the title compound as a colorless solid (0.12 g, 94%): mp 159–160° C.; $^1$H NMR (DMSO-d$_6$) δ1.30–1.45 (m, 2H), 1.60–1.85 (m, 5H), 2.46 (t, J=7.2, 2H), 2.40–2.60 (m, 3H), 2.70–2.90 (m, 2H), 2.90–3.10 (m, 2H), 3.20–3.50 (m, 6H), 7.10–7.30 (m, 5H), 9.00 (bs, 1H).

B) 4-Benzyl-1-(4-hydroxybutyl)piperidine hydrobromide

To a solution of ethyl 4-(4-benzylpiperidin-1-yl)butyrate hydrobromide (0.50 g, 1.7 mmol) in dry THF (30 mL) was added portionwise LiAlH$_4$ (0.13 g, 3.4 mmol). The resulting mixture was stirred at 25° C. for 2 h. The reaction was diluted with saturated NH$_4$Cl (100 mL) and extracted with EtOAc (2×100 mL). The collected organic phases were washed with brine (100 mL), dried and concentrated in vacuo. The crude compound was purified by filtration on silica gel using CH$_2$Cl$_2$/MeOH 8/2 as solvent to give the free amine as a colorless oil (0.34 g, 80%): $^1$H NMR (CDCl$_3$) δ1.30–1.47 (m, 4H), 1.47–1.60 (m, 1H), 1.60–1.75 (m, 6H), 1.95 (t, J=11.4 Hz, 2H), 2.37 (bs, 2H), 2.53 (d, J=6.9 Hz, 2H), 3.00 (bd, J=11.4 Hz, 2H), 3.53–3.63 (m, 2H), 7.12 (d, J=6.9 Hz, 2H), 7.19 (d, J=6.9 Hz, 1H), 7.27 (t, J=6.9 Hz, 2H).

The free amine (0.30 g) was dissolved in HBr (1.0 M in MeOH, 10 mL). The resulting solution was stirred at 25° C. for 10 min. and was concentrated in vacuo. The crude product was triturated with acetone (10 mL) for 2 h to give the title compound as a colorless solid (0.35 g, 88%): mp 129–130° C.; $^1$H NMR (DMSO-d$_6$) δ1.35–1.52 (m, 5H), 1.57–1.80 (m, 5H), 2.48 (d, J=6.6 Hz, 2H), 2.70–2.90 (m, 2H), 2.90–3.04 (m, 2H), 3.06–3.23 (m, 1H), 3.30–3.45 (m, 3H), 4.00 (bs, 1H), 7.10–7.20 (m, 3H), 7.25 (t, J=7.2 Hz, 2H), 9.22 (bd, 1H); MS (m/z) 247, 188, 91. Anal. Calcd for C$_{16}$H$_{26}$BrNO: C, 58.53; H 8.02; N, 4.33. Found: C, 57.93; H 8.12; N, 4.17.

EXAMPLE 87

4-Benzyl-4-hydroxy-1-(3-hydroxypropyl)piperidine

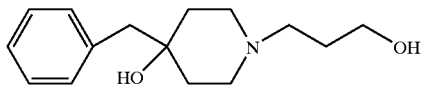

This compound was prepared in a manner similar to example 82. From 3-bromopropanol (0.453 g, 3.26 mmol) and 4-benzyl-4-hydroxypiperidine (0.52 g, 2.7 mmol) there was obtained the title compound as a pale yellow oil (0.3 g, 44%): $^1$H NMR (CDCl$_3$) δ1.45 (m, 2 H), 1.60 (m, 3 H), 2.26 (m, 4 H), 2.52 (m, 2 H), 2.64 (m, 4 H), 3.64 (t, J=5.1 Hz, 2 H), 4.80 (bs, 1 H), 7.09–7.20 (m, 5 H); MS (m/z) 249 (M$^+$, 10), 204 (100), 158 (10), 91 (18). HRMS Calcd for C$_{15}$H$_{23}$NO$_2$: 249.1737. Found: 249.1733.

EXAMPLE 88

7-Benzyl-1,2,3,5,6,7,8,9-octahydro-2-(hydroxymethyl)indolizine

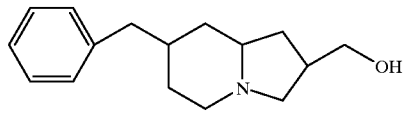

A) 4-Benzylpyridine-N-oxide

A mixture of 4-benzylpyridine (5 mL, 30 mmol), acetic acid (30 mL) and 30% hydrogen peroxide (10 mL) was heated at 80–90° C. for 5 h. Concentration under reduced pressure gave an oil that was diluted with NaHCO$_3$ (100 mL) and extracted with CH$_2$Cl$_2$ (2×100 mL). The collected organic phase was washed with brine (100 mL) and evaporated in vacuo to give the title compound as a colorless oil (5.68 g, 98%): $^1$H NMR (DMSO-d$_6$) δ3.90 (s, 2H), 7.15–7.35 (m, 7H), 8.08 (d, J=6.3 Hz, 2H).

B) 4-Benzyl-2-cyanopyridine

To a solution of 4-benzylpyridine-N-oxide (8.8 g, 48 mmol) in acetonitrile (50 mL) was added Et$_3$N (9.9 mL, 71.2 mmol). Neat trimethylsilyl cyanide (15.8 mL, 118 mmol) was added dropwise. The resulting solution was heated at reflux for 10 h under nitrogen then after cooling, diluted with CH$_2$Cl$_2$ (150 mL). The resulting solution was washed with NaHCO$_3$ (2×150 mL), dried over Na$_2$SO$_4$ and concentrated in vacuo. The crude compound was purified by filtration on silica gel using EtOAc/n-hexane as eluant to afford the title compound as a pale yellow oil (7.2 g, 78%): $^1$H NMR (CDCl$_3$) δ4.03 (s, 2H), 7.16 (d, J=7.2 Hz, 2H), 7.20–7.40 (m, 4H), 7.49 (s, 1H), 8.59 (d, J=5.1 Hz, 1H); IR (film) 2240, 1600, 1500 cm$^{-1}$.

C) Methyl 4-benzylpicolinate

A solution of 4-benzyl-2-cyanopyridine (7.1 g, 37 mmol) in MeOH (70 mL) was saturated with HCl and heated at reflux for 4 h.

The reaction mixture was concentrated under reduced pressure and was diluted with NaHCO$_3$ (100 mL) and EtOAC (100 mL). The organic phase was washed with brine (100 mL), dried over Na$_2$SO$_4$ and concentrated under reduced pressure. The crude compound was purified by filtration on silica gel using EtOAc/n-hexane as eluant to afford the title compound as a pale yellow oil (6.3 g, 76%): $^1$H NMR (CDCl$_3$) δ3.98 (s, 3H), 4.03 (s, 2H), 7.17 (d, J=6.9 Hz, 2H), 7.20–7.37 (m, 4H), 7.99 (s, 1H), 8.61 (d, J=4.8 Hz, 1H); IR (film) 1747, 1726, 1603, 1310 cm$^{-1}$.

D) 4-Benzyl-2-(hydroxymethyl)pyridine

To a solution of methyl 4-benzyl-picolinate (5.80 g, 26.0 mmol) in EtOH (100 mL)/THF (66 mL) was added a mixture of NaBH$_4$ (1.90 g, 51.0 mmol) and LiCl (2.16 g, 51.0 mmol). The resulting mixture was stirred at 25° C. for 4 h then concentrated under reduced pressure, diluted with brine (200 mL) and extracted with EtOAc (2×200 mL). The collected organic phase was washed with brine, dried over Na$_2$SO$_4$ and concentrated under reduced pressure. The crude compound was purified by flash chromatography on silica gel using EtOAc/n-hexane as eluant to afford the title compound as a pale yellow oil (4.4 g, 80%). $^1$H NMR (CDCl$_3$) δ3.8 (bs, 1H), 3.97 (s, 2H), 4.70 (s, 2H), 7.03 (d, J=4.5 Hz, 1H), 7.06 (s, 1H), 7.17 (d, J=6.9 Hz, 2H), 7.20–7.40 (m, 3H), 8.43 (d, J=4.8 Hz, 1H).

E) 4-Benzyl-2-(chloromethyl)pyridine

A solution of 4-benzyl-2-(hydroxymethyl) pyridine (2.85 g, 14.6 mmol) in SOCl$_2$ (7.50 mL, 102 mmol) was stirred at 25° C. for 30 min. and was concentrated under reduced pressure. The crude compound was diluted with EtOAc (100 mL), washed with NaHCO$_3$ (2×100 mL), dried over Na$_2$SO$_4$ and was concentrated under reduced pressure to afford the title compound as a dark oil (3.2 g, 98%): $^1$H NMR (CDCl$_3$) δ4.00 (s, 2H), 4.66 (s, 2H), 7.08 (d, J=5.1 Hz, 1H), 7.18 (d, J=7.2 Hz, 2H), 7.20–7.40 (m, 4H), 8.46 (d, J=5.1 Hz, 1H).

F) Diethyl 2-((4-benzylpyridin-2-yl)methyl)malonate

Diethyl malonate (1.15 mL, 7.60 mmol) was added to a solution of sodium ethoxide (0.106 g of sodium in 5.0 mL of EtOH). To the clear solution was then added gradually a solution of 4-benzyl-2-(chloromethyl) pyridine (0.59 g, 2.7 mmol) in EtOH (5 mL). After the mixture had been heated at reflux for 4.5 h, the EtOH was removed under reduced pressure. The residue was dissolved in EtOAc (50 mL), washed with NH$_4$Cl (2×50 mL)), dried over Na$_2$SO$_4$ and was concentrated under reduced pressure. The crude compound was purified by filtration on silica gel using EtOAc/n-hexane as eluant to afford the title compound as a colorless oil (0.9 g, 98%) 1H NMR (CDCl$_3$) δ1.12 (t, J=7.2 Hz, 4H), 1.28 (t, J=7.2 Hz, 2H), 3.25–3.40 (m, 2H), 3.92 (s, 2H), 4.00–4.30 (m, 5H), 6.93 (d, J=4.8 Hz, 1H), 7.00 (s, -H), 7.15 (d, J=7.2 Hz, 2H), 7.20–7.40 (m, 3H), 8.38 (d, J=5.1 Hz, 1H); IR (film) 2984, 1752, 1736, 1606 cm$^{-1}$.

G) Diethyl 2-((4-benzylpiperidin-2-yl)methyl)malonate

To a solution of diethyl 2-((4-benzylpyridin-2-yl)methyl) malonate (2.6 g, 7.6 mmol) in EtOH (30 mL) were added PtO$_2$ (70 mg) and conc. HCl (0.7 mL). The heterogeneous mixture was hydrogenated in a Parr hydrogenator at 30–35 psi at 25° C. for 16 h. The reaction was filtered through a Celite pad and was concentrated under reduced pressure to give the crude title compound as a yellow oil (3.0 g, 100%): $^1$H NMR (CDCl$_3$) δ1.10–1.30 (m, 6H), 1.50–2.00 (m, 6H), 2.20–2.35 (m, 1H), 2.50–2.65 (m, 2H), 2.65–2.85 (m, 1H), 3.00–3.15 (m, 1H), 3.55–3.70 (m, JH), 3.90–4.05 (m, 1H), 4.05–4.30 (m, 4H), 7.08–7.32 (m, SH), 9.70 (bs, 2H) ; IR (film) 2927, 1735 cm$^{-1}$.

Diethyl 2-((4-benzylpiperidin-2-yl)methyl)malonate hydrochloride (2.7 g, 7.0 mmol) was dissolved in EtOAc (100 mL) and washed with NaHCO$_3$ (2×60 mL), dried over Na$_2$SO$_4$ and concentrated under reduced pressure to afford the free base as a yellow oil (2.28 g): $^1$H NMR (CDCl$_3$) δ1.10–1.40 (m, 6H), 1.50–1.95 (m, 6H), 2.20–2.35 (m, 1H), 2.50–2.65 (m, 2H), 2.65–2.80 (m, 1H), 3.00–3.15 (m, 1H), 3.61 (d, J=11.7 Hz, 1H), 3.95 (t, J=6.3 Hz, 1H), 4.05–4.30 (m, 4H); MS (m/z) 347, 301, 180, 174. HRMS Calcd for C$_{20}$H$_{29}$NO$_4$: 347.2096: Found: 347.2099.

H) Ethyl 7-benzyl-2-carboxy-1,2,3,5,6,7,8,9-octahydroindolizine-3-one The neat free base obtained above was kept at 25° C. for 16 h. The crude cyclized product was crystallized from EtOAc/n-hexane to afford the title compound as a colorless solid (0.65 g, 50%): mp 108° C.; $^1$H NMR (CDCl$_3$) δ1.00–1.30 (m, 2H), 1.31 (t, J=7.2 Hz, 3H), 1.60–1.81 (m, 2H), 1.81–2.10 (m, 2H), 2.30–2.50 (m, 1H), 2.50–2.70 (m, 3H), 3.30–3.50 (m, 2H), 4.12 (dd, J=3.0 and 12.9 Hz, 1H), 4.24 (q, J=7.2 Hz, 2H), 7.14 (d, J=7.2 Hz, 2H), 7.20–7.35 (m, 3H); IR (KBr) 2936, 1733, 1693 cm$^{-1}$; MS (m/z) 301, 272, 228, 137. HRMS Calcd for C$_{18}$H$_{23}$NO$_3$: 301.1678: Found: 301.1684.

I) 7-Benzyl-1,2,3,5,6,7,8,9-octahydro-2-(hydroxymethyl) indolizine

To a solution of ethyl 7-benzyl-2-carboxy-1,2,3,5,6,7,8,9-octahydroindolizine-3-one (0.30 g, 1.0 mmol) in THF (19 mL) was added LiAlH$_4$ (0.080 g, 2.0 mmol). The resulting mixture was heated at reflux for 2 h then, after cooling to 0° C., the excess reducing agent was decomposed by the dropwise addition of a saturated Na$_2$SO$_4$ solution. The heterogeneous mixture was filtered. The filtrate was dried over Na$_2$SO$_4$ and was concentrated under reduced pressure. The crude compound was purified by crystallization from EtOAc/n-pentane to afford the title compound as a colorless solid (0.23 g, 93%): mp 85–87° C.; $^1$H NMR (CDCl$_3$) δ1.00–1.20 (m, 1H), 1.20–1.50 (m, 2H), 1.50–1.70 (m, 3H), 1.79 (d, J=12.6 Hz, 1H), 1.85–2.10 (m, 3H), 2.15–2.40 (m, 1H), 2.40–2.70 (m, 2H), 2.90–3.00 (m, 1H), 3.00–3.35 (m, 2H), 3.40–3.70 (m, 2H), 7.14 (d, J=7.2 Hz, 2H), 7.20–7.35 (m, 3H).

EXAMPLE 89

4-(4-Chlorobenzyl)-1-(3-hydroxypropyl) piperidine hydrobromide

This compound was prepared in a manner similar to example 82. From 4-(4-chlorobenzyl)piperidine hydrochloride (1.00 g, 4.06 mmol) and 3-bromopropanol (592 mg, 4.26 mmol, Aldrich) there was obtained the title compound as a colorless solid (820 mg, 60%), mp 139.5–140° C.; $^1$H NMR (CDCl$_3$) δ1.65–2.19 (m, 7 H), 2.52–2.69 (m, 4 H), 3.10–3.22 (m, 2 H), 3.55–3.90 (m, 5 H), 7.06 (d, J=8.4 Hz, 2 H), 7.25 (d, J=7.8 Hz, 2 H), 10.30 (bs, 1 H); Anal. Calcd for C$_{15}$H$_{23}$BrClNO: C, 51.67; H, 6.65; N, 4.02. Found: C, 51.77; H, 6.60; N, 3.88.

EXAMPLE 90

4-(4-Fluorobenzyl)-1-(3-hydroxypropyl) piperidine hydrobromide

This compound was prepared in a manner similar to example 82. From 4-(4-fluorobenzyl)piperidine hydrobromide (0.26 g, 0.96 mmol) and 3-bromo-1-propanol (0.13 mL, 1.4 mmol) there was obtained the free amine as an oil (0.20 g, 41%): $^1$H NMR (CDCl$_3$) δ1.15–1.35 (m, 2H), 1.40–1.57 (m, 1H), 1.55–1.75 (m, 4H), 1.85 (t, J=11.1 Hz, 2H), 2.46 (d, J=6.9 Hz, 2H), 2.55 (t, J=5.7 Hz, 2H), 3.01 (d, J=11.4 Hz, 2H), 3.76 (t, J=5.1 Hz, 2H), 5.25 (bs, 1H), 6.93 (t, J=8.7 Hz, 2H), 7.00–7.10 (m, 2H).

The HBr salt was obtained as a colorless solid (0.05 g, 54%): mp 108–110° C.; $^1$H NMR (DMSO-d$_6$) δ1.35–1.55 (m, 2H), 1.60–1.85 (m, 5H), 2.70–2.85 (m, 2H), 2.90–3.05 (m, 2H), 3.05–3.20 (m, 1H), 3.30–3.50 (m, 4H), 4.73 (bs, 1H), 7.08 (t, J=8.7 Hz, 2H), 7.14–7.23 (m, 2H), 9.80 (bs, 1H); MS (m/z) 251. HRMS Calcd for C$_{15}$H$_{22}$FNO: 251.1685. Found: 251.169.

EXAMPLE 91

4-(4-Fluorobenzyl)-1-(3-hydroxybutyl) piperidine hydrochloride

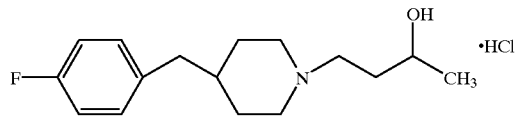

A) 4-(4-(4-Fluorobenzyl)piperidin-1-yl)-2-butanone

To a solution of 4-(4-fluorobenzyl)piperidine (0.50 g, 2.2 mmol) in isopropanol (5 mL) was added methylvinyl ketone (0.25 mL, 3.0 mmol). The resulting solution was stirred at reflux for 1 h then concentrated under reduced pressure to afford the title compound as a pale yellow oil (0.58 g, 99%): $^1$H NMR (CDCl$_3$) δ1.15–1.35 (m, 2H), 1.38–1.56 (m, 1H), 1.603 (bd, J=12.6 Hz, 2H), 1.894 (t, J=11.7 Hz, 2H), 2.155 (s, 2H), 2.486 (d, J=6.9 Hz, 2H), 2.615 (s, 3H), 2.8–2.9 (m, 2H), 6.9–7.0 (m, 2H), 7.0–7.1 (m, 2H); IR (film) 2928, 1720, 1514, 1219 cm$^{-1}$.

B) 4-(4-Fluorobenzyl)-1-(3-hydroxybutyl)piperidine hydrochloride

To a solution of 4-(4-(4-fluorobenzyl)piperidin-1-yl)-2-butanone (0.15 g, 0.57 mmol) in EtOH (5 mL) was added NaBH$_4$. The resulting mixture was stirred at 25° C. for 1 h. After quench of the excess reducing agent with water, the solution was concentrated under reduced pressure. The crude compound was dissolved in EtOAc (50 mL) and washed with NaHCO$_3$ (50 mL), dried and was concentrated under reduced pressure to give the free base as a colorless oil (0.15 g) $^1$H NMR (CDCl$_3$) δ1.13 (d, J=6.0 Hz, 3H), 1.10–1.30 (m, 3H), 1.40–1.70 (m, 6H), 1.95–2.10 (m, 1H), 2.45 (d, 6.9 Hz, 2H), 2.40–2.60 (m, 2H), 2.75–2.90 (m, 1H), 3.00–3.20 (m, 1H), 3.80–4.00 (m, 1H), 6.91 (t, J=8.7 Hz, 2H), 7.00–7.10 (m, 2H).

The HCl salt was obtained as a colorless solid (0.12 g, 70%): mp 99–103° C.; $^1$H NMR (DMSO-d$_6$) δ1.20 (d, J=6.3 Hz, 3H), 1.35–1.55 (m, 2H), 1.60–1.95 (m, 6H), 2.59 (d, J=6.3 Hz, 2H), 2.75–3.00 (m, 2H), 3.05–3.30 (m, 2H), 3.55 (t, J=11.5 Hz, 2H), 3.75–3.90 (m, 1H), 7.00 (t, J=8.7 Hz, 2H), 7.18 (dd, J=5.7 and 7.8 Hz, 2H); MS (m/z) 265, 206, 109.

EXAMPLE 92

(R)-4-(4-Fluorobenzyl)-1-(3-hydroxy-2-methylpropyl) piperidine hydrochloride

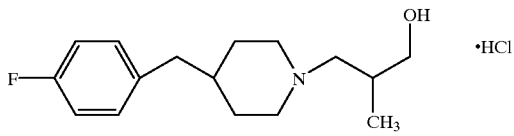

This compound was prepared in a manner similar to example 82. From 4-(4-fluorobenzyl)piperidine hydrochloride (0.25 g, 1.1 mmol) and (R)-3-bromo-2-methyl-1-propanol (0.14 mL, 1.3 mmol) there was obtained the free amine as an oil (0.20 g, 70%): MS (m/z) 265, 206; HRMS Calcd for $C_{16}H_{24}FNO$: 265.1842. Found: 265.1842.

The HCl salt was obtained as a colorless solid; mp 128–130° C.; $^1$H NMR (DMSO-$d_6$) δ0.87 (d, J=6.6 Hz, 3H), 1.40–1.60 (m, 3H), 1.60–1.80 (m, 3H), 1.90–2.10 (m, 1H), 2.65–2.85 (m, 2H), 2.90–3.05 (m, 1H), 3.40–3.50 (m, 3H), 4.90 (bs, 1H), 7.09 (t, J=8.7 Hz, 2H), 7.15–7.24 (m, 2H), 9.10 (bs, 1H); MS (m/z) 265, 206.

EXAMPLE 93

1-(3-Hydroxypropyl)-4-(4-methoxybenzyl) piperidine hydrobromide

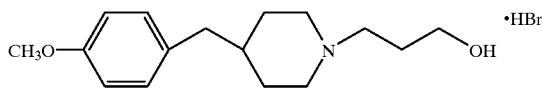

This compound was prepared in a manner similar to example 82. From 4-(4-methoxybenzyl)piperidine hydrobromide (0.54 g, 1.9 mmol) and 3-bromo-1-propanol (0.25 mL, 2.8 mmol) there was obtained the free amine as a pale yellow oil (0.20 g, 41%): $^1$H NMR (CDCl$_3$) δ1.05–1.35 (m, 2H), 1.40–1.60 (m, 1H), 1.55–1.75 (m, 4H), 1.87 (t, J=11.4 Hz, 2H), 2.45 (d, J=7.2 Hz, 2H), 2.57 (t, J=5.7 Hz, 2H), 3.03 (d, J=11.1 Hz, 2H), 3.78 (s, 3H), 3.70–3.80 (m, 2H), 6.82 (d, J=8.1 Hz, 2H), 7.04 (d, J=8.1 Hz, 2H).

The HCl salt was obtained as a colorless solid (0.13 g, 64%) mp 129–131° C.; $^1$H NMR (DMSO-$d_6$) δ1.30–1.55 (m, 2H), 1.55–1.70 (m, 3H), 1.70–1.85 (m, 2H), 2.42 (d, J=6.3 Hz, 2H), 2.70–2.85 (m, 2H), 2.90–3.05 (m, 2H), 3.05–3.20 (m, 1H), 3.20–3.5 (m, 3H), 3.68 (s, 3H), 6.82 (d, J=8.4 Hz, 2H), 7.05 (d, J=8.4 Hz, 2H), 9.90 (bs, 1H); MS (m/z): 263, 218, 121.

EXAMPLE 94

4-Benzyl-1-(5-hydroxypentyl)piperidine

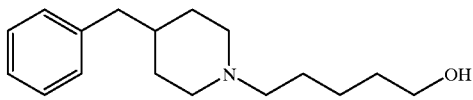

This compound was prepared in a manner similar to example 82.

EXAMPLE 95

1-(4-Benzoyloxybut-2-ynyl)-4-benzylpiperidine

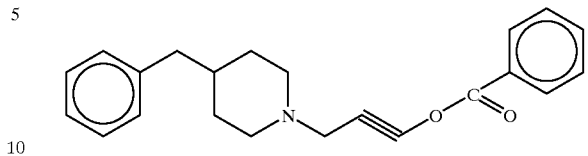

A) 1-Benzoyloxybut-4-ol-2-yn.

To a solution of but-2-yne-1,4-diol (19 g, 0.22 mol) in a mixture of dry benzene (50 mL) and dry pyridine (22 mL) was added dropwise a solution of benzoyl chloride (22 mL) in dry chloroform (40 mL) at 0–5° C. The resulting solution was allowed to stir at room temperature for another 4 hr and was washed with 1 N $H_2SO_4$ (4×20 mL), water (3×20 mL) and was dried over $Na_2SO_4$. Evaporation of solvent gave a residue, which was purified by flash chromatography to give the title compound as a colorless oil (3.5 g, 10%): $^1$H NMR (CDCl$_3$) d 1.74 (bs, 1 H), 4.34 (s, 2 H), 4.97 (s, 2 H), 7.45 (m, 2 H), 7.56 (m, 2 H), 8.06 (d, J=7.5 Hz, 2 H).

B) 1-Benzoyloxy-4-bromobut-2-yne.

To a stirred solution of 1-benzoyloxybut-4-ol-2-yn (3.5 g, 18 mmol) in benzene (50 mL) was added dropwise phosphorus tribromide (1.25 mL). The resulting solution was allowed to stir at room temperature for 24 hr. The mixture was poured into ice water (50 g). The organic layer was separated and the aqueous phase was extracted with ether (3×30 mL). The combined organic layer was washed with saturated NaHCO$_3$ (2×20 mL), water (2×20 mL) and was dried over $Na_2SO_4$. Evaporation of solvent gave the product as pale yellow oil (3.72 g, 82%): $^1$H NMR (CDCl$_3$) d 3.96 (s, 2 H), 4.99 (s, 2 H), 7.46–7.59 (m, 3 H), 8.06 (d, J=7.8 Hz, 2 H).

C) 1-(4-Benzoyloxybut-2-ynyl)-4-benzylpiperidine.

A mixture of 1-benzoyloxy-4-bromobut-2-yne (1.26 g, 5.00 mmol), 4-benzylpiperidine (0.964 g, 5.50 mmol) and K$_2$CO$_3$ (1.52 g, 11.0 mmol) in 50 mL of CH$_3$CN was refluxed under N$_2$ for 24 hr. The inorganic salt was removed through a short column of silica gel and was washed with EtOAc (3×30 mL). The filtrate was evaporated in vacuo to give a residue, which was purified by flash chromatography to give the product as a brown oil (0.55 g, 32%): $^1$H NMR (CDCl$_3$) d 1.34 (m, 2 H), 1.50 (m, 1 H), 1.63 (m, 2 H), 2.11 (m, 2 H), 2.51 (d, J=6.9 Hz, 2 H), 2.78 (m, 2 H), 2.86 (d, J=11.1 Hz, 2 H), 3.31 (s, 2 H), 4.94 (s, 2 H), 7.12–7.52 (m, 8 H); MS (m/z) 348 (M$^+$+1, 20), 347 (M$^+$, 100), 346 (M$^+$−1, 60), 226 (30), 105 (100).

EXAMPLE 96

4-Benzyl-1-(4-hydroxybut-2-yn-1-yl)piperidine

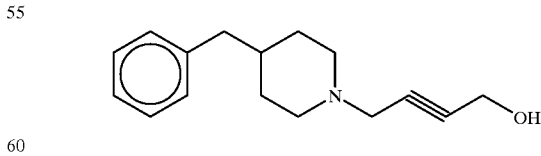

A steam of ammonia gas was bubbled through dry-ice/acetone cooled methanol until the concentration of ammonia was about 20%. To this solution was added a solution of 1-(4-benzoyloxybut-2-yn-1-yl)-4-benzylpiperidine (300 mg, 0.860 mmol) in 2 mL of methanol. The resulting solution was allowed to stir at room temperature for 24 hr.

Methanol was evaporated in vacuo to give a residue, which was purified by flash chromatography to give the title compound as a brown oil (140 mg, 67%): $^1$H NMR (CDCl$_3$) d 1.35 (m, 2 H), 1.50 (m, 1 H), 1.62 (m, 2 H), 2.08 (m, 2 H), 2.51 (d, J=6.9 Hz, 2 H), 2.89 (d, J=11.1 Hz, 2 H), 3.25 (s, 2 H), 4.24 (s, 2 H), 4.50 (bs, 1 H), 7.10–7.26 (m, 5 H). HRMS calcd for C$_{16}$H$_{21}$NO 243.1613, found 243.1618.

EXAMPLE 97

4-Benzyl-1-(but-2-ynyl)piperidine

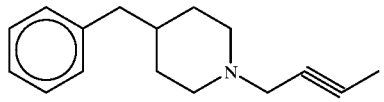

A) 1-Bromobut-2-yne.

To a solution of 2-butyn-1-ol (2.5 g, 40 mmol) in 30 mL of ether and 0.22 mL of pyridine was added dropwise a solution of phosphorus tribromide (2.6 mL) in 5 mL of ether at −20 to −30° C. The resulting solution was allowed to warm to room temperature and was refluxed for an additional 2 hr. After cooling to room temperature, the mixture was poured into ice-water (20 g). The mixture was extracted with ether (3×50 mL). The combined extract was washed with brine (20 mL) and was dried over Na$_2$SO$_4$. Evaporation of solvent gave the product (2 g, 38%): $^1$H NMR (CDCl$_3$) d 1.59 (s, 3 H), 3.56 (s, 2 H).

B) 4-Benzyl-1-(but-2-ynyl)piperdine.

A mixture of 1-bromobut-2-yne (1.19 g, 9.00 mmol), 4-benzylpiperidine (1.58 g, 9.00 mmol) and K$_2$CO$_3$ (2.5 g, 18 mmol) in 25 mL of CH$_3$CN was refluxed for 12 hr. The mixture was filtered and was washed with EtOAc (3×30 mL). The filtrate was evaporated in vacuo and was purified by flash chromatography to give the product as a colorless oil (0.9 g, 50%): $^1$H NMR (CDCl$_3$) d 1.31 (m, 2 H), 1.60 (m, 1 H), 1.63 (m, 2 H), 1.81 (s, 3 H), 2.04 (m, 2 H), 2.52 (d, J=9.9 Hz, 2 H), 2.88 (m, 2 H), 3.16 (s, 2 H), 7.15–7.27 (m, 5 H); HRMS calcd for C$_{16}$H$_{21}$N 227.1670, found 227.1670.

EXAMPLE 98

4-(4-Chlorobenzyl)-1-(tetralin-2-yl)piperidine hydrochloride

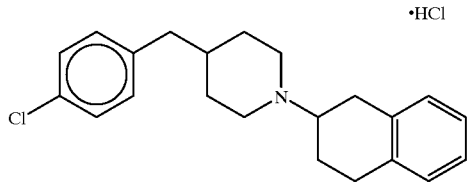

To a stirred solution of 4-(4-chlorobenzyl)piperidine (2.00 g, 9.54 mol) in MeOH (20 mL), 2-tetralone (1.39 g, 9.54 mmol) was added at 25° C. Upon addition, the solution turned deep blue. Solid NaCNBH$_3$ (1.19 g, 19.1 mmol) was added and the resulting deep blue solution was allowed to stir at 25° C. under N$_2$. After 7 days, the reaction mixture was added to a solution of 10% HCl (100 mL) to give a yellow gum. The gum was dissolved in EtOAc (50 mL). The aqueous portion was extracted with EtOAc (2×50 mL). The combined EtOAc portion was washed with a saturated solution of NaHCO$_3$ (2×50 mL) and water (50 mL). The EtOAc portion was filtered through cotton and the solvent was removed to give a brown oil (2.9 g). Initial purification was effected by chromatography on silica gel with CHCl$_3$ elution. More mobile impurities eluted initially and subsequently the product eluted as a mixture. The purest fractions (TLC) were combined and the solvent was removed to give a brown oil. The oil was dissolved in MeOH (10 mL), filtered through Celite and the solvent was removed to give a brown oil. The oil was dissolved in hexanes (10 mL, a dark gum didn't dissolve), filtered through Celite and the solvent was removed to give an amber oil. The oil was dissolved in MeOH (10 mL) and a solution of HCl in MeOH (≈1 M) was added until the amine solution was permanently acidic (pH paper red). The solvent was removed to give a beige solid. The solid was triturated with ether (30 mL) and was collected. The collected solid was crystallized from 2-butanone/MeOH. The collected solid was mostly dissolved in a boiling solution of 2-butanone (100 mL)/MeOH (6 mL). The resulting suspension was hot filtered and the filtrate was concentrated to approximately 70 mL at which point it turned cloudy. This was allowed to cool to 25° C. and was stored overnight at 4° C. The solid was collected from the resulting suspension, washed with 2-butanone (3×2 mL) and was dried in vacuo (100° C., 0.005 Torr) to yield the title compound as a colorless, fluffy solid (705 mg, 20%): mp 243–245° C. (dec); $^1$H NMR (CDCl$_3$ d 1.50–2.00 (m, 4 H), 2.15–2.35 (m, 2 H), 2.50–3.58 (m, 12 H) 6.96–7.20 (m, 6 H), 2.24 (d, J=7.5 Hz, 2 H), 12.40 (bs, 1 H); MS m/z 339 (M$^+$ ($^{35}$Cl), 100). Anal. Calcd. for C$_{22}$H$_{27}$Cl$_2$N: C, 70.21; H, 7.23; N, 3.72.

EXAMPLE 99

4-(4-chlorobenzyl)-1-(3-hydroxybutyl) piperidine hydrochloride

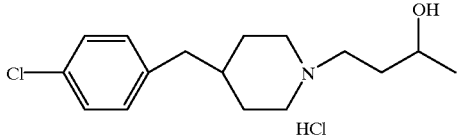

a) 2[1-(4-(4-chlorobenzyl)piperidin)] ethyl methyl ketone.

To a solution of 4-(4-chlorobenzyl)piperidine (1.0 g, 4.78 mmol) in methyl vinyl ketone (1.0 ml) was added H$_2$O (1 drop) and the resulting solution stirred at 110° C. for 2 h. The crude mixture was purified by filtration on silica gel using CH$_2$Cl$_2$/MeOH as eluant to afford the title compound (1.20 g, 90%) as a pale yellow oil: $^1$H NMR (CDCl$_3$) 1.35–1.55 (m, 5H), 1.63 (d, J =12.3, 2H), 2.055 (t, J=9.6, 2H), 2.154 (s, 2H), 2.40 (d, J=6.3, 2H), 2.748 (s, 2H), 2.972 (d, J=11.4, 2H), 7.034 (d, J=8.1, 2H), 7.218 (d, J=8.1, 2H).

b) 4-(4-chlorobenzyl)-1-(3-hydroxybutyl) piperidine hydrochloride.

To a solution of 2[1-(4-(4-chlorobenzyl)piperidin)]ethyl methyl ketone (1.10 g, 3.93 mmol) in ethanol (5 mL) was added NaBH$_4$. (0.22 g, 5.90 mmol). The resulting mixture was stirred at 25° C. for 2 h then, after quench of the excess reducing agent with water, the solution was concentrated under reduced pressure. The crude compound was dissolved in EtOAc (50 ml) and washed with NaHCO$_3$ (50 ml), dried and concentrated under reduced pressure. The crude compound was purified by filtration on silica gel using CH$_2$Cl$_2$/MeOH as eluant to give the free base (0.75 g, 70%) as a pale yellow oil: $^1$H NMR (CDCl$_3$) 1.170 (d, J=6.0), 1.10–1.40 (m, 2H), 1.4–1.55 (m, 2H), 1.55–1.70 (m, 3H), 1.765 (t, J=11.4, 1H), 2.047 (t, J=11.4, 1H), 2.473 (d, J=6.9, 2H), 2.45–2.70 (m, 2H), 2.937 (d, J=10.2, 1H), 3.159 (d, J=10.8, 1H), 3.86–4.0 (m, 1H), 6.4 (bs, 1H), 7.034 (d, J=8.1, 2H), 7.223 (d, J=8.1, 2H). The HCl salt as a white solid: mp 96–101° C. Anal. Calcd for $C_{16}H_{25}Cl_2NO$: C 60.38, H 7.92, N 4.40, found C 60.06, H 7.88, N 4.41.

EXAMPLE 100

4-benzyl-1-(3-hydroxy-butyl) piperidine hydrochloride

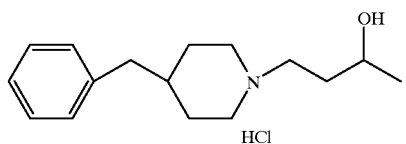

The title compound was prepared from 4-benzylpiperidine (2.00 g, 11.41 mmol) and methyl vinyl ketone (3.80 ml) in two steps (0.80 g) as a white solid: mp 133–135° C.; $^1$H NMR (CD$_3$OD) 1.20 (d, J=6.0, 3H), 1.40–1.60 (m, 2H), 1.70–1.95 (m, 6H), 2.59 (d, J=6.3, 2H), 2.80–2.95 (m, 2H), 3.05–3.25 (m, 2H), 3.25–3.35 (m, 2H), 3.50–3.62 (m, 2H), 3.75–3.90 (m, 1H), 7.12–7.22 (m, 3H), 7.22–7.30 (m, 2H); Anal calcd for $C_{16}H_{26}ClNO$: C 67.70, H 9.23, N 4.94, found C 67.57, H 9.10, 4.93.

EXAMPLE 101

4-(4-nitrobenzyl)-1-(3-hydroxybutyl) piperidine hydrochloride

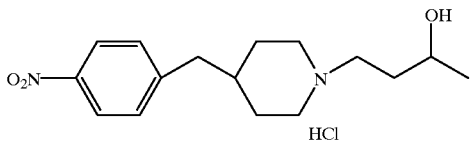

The title compound was prepared from 4-(4-nitrobenzyl)-piperidine (3.50 g, 15.81 mmol) and methyl vinyl ketone (5.00 ml) in two steps as a white solid: mp 105–107° C.; $^1$H NMR (CD$_3$OD) 1,20 (d, J=6.0, 3H), 1.40–1.63 (m, 2H), 1.63–2.05 (m, 6H), 2.74 (d, J=6.9, 2H), 2.80–3.00 (m, 2H), 3.05–3.25 (m, 2H), 3.50–3.65 (m, 2H), 3.75–3.90 (m, 1H), 7.44 (d, J=8.4, 2H), 8.16 (d, J=8.4, 2H); Anal calcd for $C_{16}H_{25}ClN_2O_3$ 1/2 $H_2O$: C 57.0, H 7.78, N 8.32, found C 56.24, H 7.69, N 8.07.

EXAMPLE 102

4-benzyl-1-(3-hydroxy-3-methylbutyl) piperidine hydrochloride

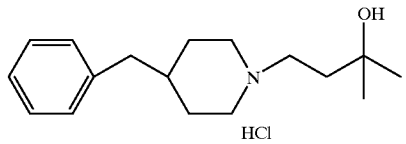

To a solution of 2[1-(4-benzylpiperidin)]ethyl methyl ketone (0.50 g, 2.04 mmol) in dry THF (10 mL) was added dropwise at –60° C. a solution 1.4 M of methyl magnesium bromide in toluene/THF. The resulting solution was stirred at –60° C. for 2 h then warmed up to 25° C. for 1 h. After this period the reaction solution was diluted with NaHCO$_3$ (50 mL) and extracted with EtOAc (2×30 mL). The collected organic phase is washed with brine (50 mL), dried and concentrated under reduced pressure. The crude mixture is purified by flash-chromatography using CH$_2$Cl$_2$/MeOH as eluant to give the free base (0.31 g) as a colorless oil, which was converted to the Hcl salt to afford the title compound (0.14 g) as a white solid: mp 136–138° C.; $^1$H NMR (CD$_3$OD) 1.25 (s, 6H), 1.40–1.58 (m, 2H), 1.80–1.98 (m, 5H), 2.62 (d, J=6.6, 2H), 2.91 (t, J=11.7, 2H), 3.16–3.24 (m, 2H), 3.52–3.63 (m, 2H), 4.89 (bs, 2H), 7.15–7.38 (m, 5H); HRMS Calcd. for $C_{17}H_{27}NO$: 261.2093; Found: 261.2099.

EXAMPLE 103

2-[2-(4-Hydroyphenyl)ethylamino]-5-benzyl-1,3-diazacyclohexene

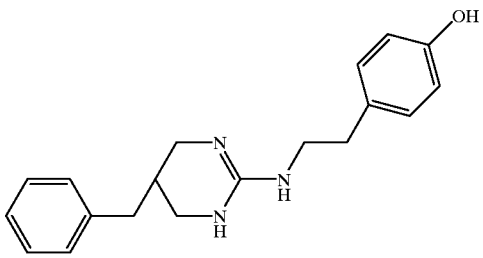

a) Benzyl malonamide.

To a solution of diethyl benzylmalonate (50 g, 0.2 mol) in 150 mL of methanol was added 72 mL of 30% ammonium hydroxide. The resulting solution was allowed to stir for 2 days. A white solid was filtered off and dried in vacuo to give 23 g (60%) of the title product. mp 221–223° C. $^1$H NMR (CDCl$_3$) 2.934 (d, J=7.5, 2 H), 3.232 (t, J=7.5, 1 H), 7.186 (m, 5 H).

b) 2-Benzyl-1,3-diaminopropane.

To a suspension of benzyl malonamide (18.2 g, 95 mmol) in 200 mL of tetrahydrofuran was added dropwise 1 M solution of B$_2$H$_6$.THF (416 mL) at 0° C. After addition, the solution was brought to reflux for 3 hrs. The reaction mixture was allowed to cool to rt, and the excess of diborane was destroyed by very cautious dropwise addition of distilled water (100 mL). The solution was evaporated to dryness on a rotary evaporator to yield a dry, white solid mess, which was slowly treated with 6 N HCl aqueous solution (350 mL). The resulting mixture was heated at reflux for 1 hr and then again taken to dryness on a rotary evaporator. The residue was dissolved into 150 mL of water and then 6 N NaOH aqueous solution was added. The solution was extracted with chloroform (4×200 mL). The combined extracts were dried over sodium sulfate and evaporated to give 12.6 g (81%) of the product as a clear oil. $^1$H NMR (CDCl$_3$) 1.75 (m, 1H), 2.625 (d, J=7.2 Hz, 2 H), 2.728 (m, 4 H), 7.191–7.260 (m, 5 H).

c) 5-Benzylhexahydropyrimidine-2-thione.

To a solution of 2-benzyl-1,3-diaminopropane (1.64 g, 10 mmol) in 10 mL of 95% ethanol was added dropwise a solution of 4 mL of carbon disufide in 10 mL of 95% ethanol at 0° C. A gummy solid formed. The resulting mixture was heated under reflux for 2 hrs and cooled to rt. To this mixture was added 0.5 mL of concnetrated HCl aqueous solution and heated to reflux again for 24 h. A white solid was collected by filtration to give 1.2 g (58%) of the product: mp 162–163° C. $^1$H NMR (DMSO-d$_6$) 2.0 (m, 1H), 2.536 (d, J=7.2, 2 H), 2.787 (m, 2 H), 2.988 (m, 2 H), 7.155–7.269 (m, 5 H), 7.845 (s, 2 H).

d) 5-Benzyl-2-methylmercaptotetrahydropyrimidinium Iodide.

To a solution of 5-benzylhexahydropyrimidine-2-thione (0.657 g, 3.19 mmol) in 5 mL of ethanol was added a solution of methyl iodide (0.453 g, 3.19 mmol) in 2 mL of ethanol at 50° C. The resulting solution was allowed to stir at rt for 24 hrs. Ethanol was evaporated in vacuo to give an oil, to which was added 10 mL of ether. A white solid was collected by filtration and dried to give 0.65 g (63%) of the product. mp 138–140° C. $^1$H NMR (CDCl$_3$) 2.25 (m, 1H), 2.669(s, 3 H), 2.780 (d, J=5.0, 2 H), 3.170 (m, 2 H), 3.612 (m, 2 H), 7.131–7.306 (m, 5 H), 8.810 (s, 2 H).

e) 2-[2-(4-Hydroyphenyl)ethylamino]-5-benzyl-1,3-diazacyclohexene.

A solution of 5-benzyl-2-methylmercapto-2-tetrahydropyrimidinium iodide (0.348 g, 1.0 mmol), tyramine (0.206 g, 1.5 mmol) in 10 mL of ethanol was allowed to stir at reflux for 24 hrs. After cooling down, ethanol was evaporated to give a residue, which was purified by flash chromatography (10% methanol in chloroform), giving 150 mg (49%) of the title compound as white-off solid. mp 153–155° C. $^1$H NMR (CDCl$_3$) 1.980 (s, 2 H), 2.245 (m, 1H), 2.659(m, 2 H), 3.046 (m, 2 H), 3.276 (m, 2 H), 5.010 (s, 2 H), 7.131–7.306 (m, 9 H). HRMS Calcd for $C_{19}H_{23}N_3O$: 309.1831; Found: 309.1836.

EXAMPLE 104

4-(4-methylbenzyl)-1-(3-hydroxy-butyl) piperidine hydrochloride

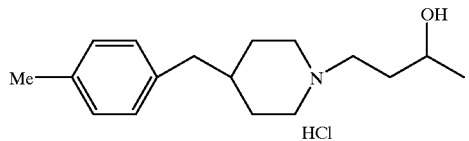

The title compound was prepared from 4-(4-methylbenzyl)piperidine (0.61 g) and methyl vinyl ketone (2.00 ml) in two steps (0.62 g) as a white solid: mp 134–136° C.; $^1$H NMR (DMSO) 1.07 (d, J=6.3, 3H), 1.36–1.56 (m, 2H), 1.58–1.80 (m, 5H), 2.42–2.52 (m, 6H), 2.68–2.88 (m, 2H), 2.89–3.10 (m, 2H), 3.34–3.46 (m, 1H), 3.56–3.71 (m, 1H), 4.77 (bs, 1H), 7.04 (d, J=7.5, 2H), 7.09 (d, J=7.8, 2H), 9.75 (bs, 1H); Anal calcd for $C_{17}H_{28}ClNO$: C 68.55, H 9.48, N 4.70, found C 68.36, H 9.55, N 4.65.

EXAMPLE 105

4-(4-aminobenzyl)-1-(3-hydroxy-butyl) piperidine hydrochloride

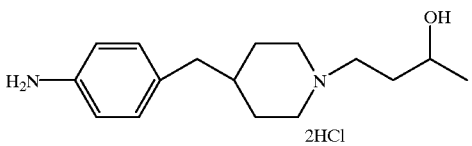

A mixture of 4-(4-nitrobenzyl)-1-(3-hydroxy-butyl) piperidine hydrochloride (0.17 g, 0.53 mmol) in methanol (10 mL) with Pd/C 10% (0.06 g) was hydrogenated at 1 atm and 25° C. for 18 h then, after filtration through a celite pad and concentration under reduced pressure, the crude compound was triturated with EtOAc (10 mL) for 15 h to afford the title compound (0.13 g, 80%) as a pale pink solid: mp 155–160° C.; $^1$H NMR (D$_2$O) 1.038 (d, J=6.0, 3H), 1.28–1.36 (m, 2H), 1.58–1.82 (m, 5H), 2.342 (d, J=6.3, 2H), 2.65–2.80 (m, 2H), 2.90–3.10 (m, 2H), 3.32–3.43 (m, 2H), 3.65–3.80 (m, 1H), 6.64 (d, J=8.7, 2H), 6.909 (d, J=8.4, 2H) ; Anal calcd for $C_{16}H_{27}ClN_2O \cdot H_2O$: C 60.65, H 9.22, N 8.84, found C 61.45, H 8.76, N 8.81.

EXAMPLE 106

4-(4-Chlorobenzyl)-1-(N-(2-(4-fluorophenoxy)ethyl) amino)piperidine hydrobromide

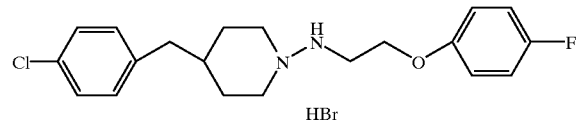

a) 4-(4-Chlorobenzyl)-1-nitrosopiperidine A stirred solution of 4-(4-chlorobenzyl)piperidine (1.60 gm, 7.63 mmol) in H$_2$O (3 mL) containing concd HCl (0.8 mL) was warmed to 65–70° C. A solution of NaNO$_2$(658 mg, 9.54 mmol) in H$_2$O (1 mL) was added dropwise so as to maintain the above temperature. After addition, the reaction was allowed to stir at the above temperature for 10 min. The reaction was allowed to cool to 25° C. and was extracted with toluene (5 mL and 2 mL). The yellow extract was dried over Na$_2$SO$_4$, filtered, and the solvent removed to give a yellow liquid. The liquid was dried further (25° C., 0.005 Torr) to give a yellow liquid (1.69 g, 93%): $^1$H NMR (CDCl$_3$) 1.00–1.15 (m, 1H), 1.30–1.47 (m, 1H), 1.68–1.98 (m, 3H), 2.42–2.60 (m, 3H), 3.60 (dt, J=12 and 3.0 Hz, 1H), 4.75 (dp, J=14, 2.1 Hz, 1H), 5.04 (dp, J=14 and 2.1 Hz, 1H), 7.08 (d, J=8.4 Hz, 2H), 7.28 (d, J=8.4 Hz, 2H)

b) 1-Amino-4-(4-chlorobenzyl)piperidine

A suspension of LiAlH$_4$ (535 mg, 14.1 mmol) in dry THF (10 mL) was heated to refux with stirring. The mixture was removed from the heat source and a solution of 4-(4-chlorobenzyl)-1-nitrosopiperidine (1.68 g, 7.04 mmol) in dry THF (10 mL) was added with stirring so as to maintain a gentle reflux. After addition, the reaction was allowed to stir at reflux for 10 min. The reaction was allowed to cool to 25° C. and ether (60 mL) was added. Water (10 mL) was slowly added with stirring so as to destroy the excess hydride. The ether layer was separated and the aqueous portion was washed with ether. The combined ether portion was dried over Na$_2$SO$_4$ and the solvent was removed to give a near colorless liquid. This was filtered through a column of silica gel (2.5×10 cm) with 2% EtOH/98% CHCl$_3$ elution to remove a low TLC R$_f$ impurity. Solvent removal and drying in vacuo (0.005 Torr, 25° C.) gave a colorless liquid that solidified with scratching (1.20 g, 76%): mp 49–51° C.; $^1$H NMR (CDCl$_3$) 1.24–1.52 (m, 3H), 1.56–1.68 (m, 2H), 2.00 (t, J=10, 2H), 2.48 (d, J=6.6, 2H), 2.86 (bs, 2H), 3.08 (d, J=11, 2H), 7.05 (d, J=8.4, 2H), 7.23 (d, J=8.4, 2H).

c) 4-(4-Chlorobenzyl)-1-(N-(2-(4-fluorophenoxy)ethyl) amino)piperidine hydrobromide From a mixture of 1-amino-4-(4-chlorobenzyl)piperidine (500 mg, 2.22 mmol), 2-(4-fluorophenoxy)ethyl bromide (511 mg, 2.33 mmol) and K$_2$CO$_3$ (322 mg, 2.33 mmol) in CH$_3$CN (10 mL) was obtained the title compound as colorless flakes (165 mg, 17%): mp 214–215° C. (dec). $^1$H NMR (CD$_3$OD) 1.75–2.05 (m, 5H), 2.70 (d, J=6.9, 2H), 3.40–3.52 (m, 2H), 3.83 (d, J=13, 2H), 4.00 (t, J=4.5, 2H), 4.52 (t, J=4.5, 2H), 6.96–7.10 (m, 4H), 7.22 (d, J=8.7, 2H), 7.30 (d, J=8.7, 2H); Anal Calcd for $C_{20}H_{25}BrClFN_2O$: C, 54.13; H 5.68; N, 6.31. Found: C, 54.23; H, 5.59; N, 6.23.

EXAMPLE 107

4-(1-Adamantylmethyl)-1-(2-(4-hydroxyphenoxy) ethyl)piperidine

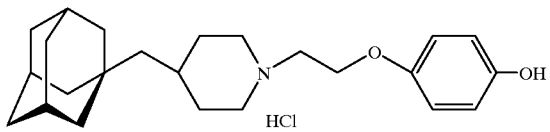

HCl a) 4-(1-Adamantylmethyl)piperidine hydrochloride

A mixture of 4-(1-adamantylmethyl)pyridine (500 mg, 2.20 mmol) and PtO$_2$ (15 mg) in MeOH (20 mL) containing concd HCl (1 mL) was allowed to shake under H$_2$ (25–30 psi) for 24 h. NMR analysis showed only about 45% reaction. An additional portion of catalyst was added and the reaction was allowed to proceed as above for an additional 24 h. The analysis now showed about 70% reaction. The reaction was allowed to proceed at 50 psi for a final 24 h (72 h total). A crystalline solid was observed in the reaction mixture. The addition of CH$_2$Cl$_2$ and warming dissolved this material. The analysis now showed ~95% reaction. The catalyst was removed by filtration (Celite) and the solvent was removed to give a yellow solid. The solid was dissolved in boiling MeOH (12 mL) and the solution was hot filtered. The filtrate was concd to 8 mL and was cooled in an ice bath to give a suspension. The solid was collected, was washed with ice cold MeOH (3×1 mL) and was dried in vacuo (100° C., 0.005 Torr) to give the title compound as a pale yellow crystalline solid (365 mg, 62%): mp >300° C.; $^1$H NMR (DMSO-d$_6$) 0.95 (d, J =4.5, 2H), 1.22–1.78 (m, 17H), 1.90 (s, 3H), 2.81 (dd, J=22 and 11, 2H), 3.13 (d, J=12, 2H), 8.68 (bs, 1H), 8.89 (bs, 1H).

b)The title compound was prepared from 4-(1-adamantylmethyl)piperidine hydrochloride (350 mg, 1.30 mmol) and 2-(4-hydroxyphenoxy)ethyl bromide (295 mg, 1.36 mmol) as a beige crystalline solid (387 mg, 81%): mp 178–179° C.; $^1$H NMR (DMSO-d$_6$) 0.93 (d, J=5.1, 2H), 1.05–1.70 (m, 17H), 1.85–2.07 (m, 5H), 2.56 (t, J=6.0, 2H), 2.72–2.88 (m, 2H), 3.90 (t, J=6.0, 2H), 6.63 (d, J=9.0, 2H), 6.71 (d, J=9.0, 2H), 8.88 (bs, 1H); Anal. calcd for C$_{24}$H$_{35}$NO$_2$: C, 78.00; H, 9.55; N, 3.79. Found: C, 78.03; H, 9.44; N, 3.77.

EXAMPLE 108

N-(3-(2-oxobenzimidazol-5-oxy)propyl)-1,2,3,4-tetrahydroisoquinoline

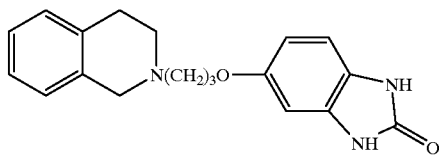

a) From a mixture of 1,2,3,4-tetrahydroisoquinoline (285 mg, 2.14 mmol), 3-(4-amino-3-nitrophenoxy)propyl chloride(231 mg, 1.0 mmol) and NaI (103 mg) in toluene (15 mL) was obtained 250 mg (76%) of N-[3-(4-amino-3-nitrophenoxy)propyl]-1,2,3,4-tetrahydroisoquinoline as a yellow powder. $^1$H NMR (CDCl$_3$): 2.05–2.18 (m, 2H), 2.779 (t, 2H, J=7), 2.83–2.88 (m, 2H), 2.93–2.97 (m, 2H), 3.753 (s, 2H), 4.049 (t, 2H, J=6), 6.752 (d,1H, J=9), 7.03–7.15 (m, 5H), 7.556 (d, 1H, J=3).

b) From a mixture of N-[3-(4-amino-3-nitrophenoxy)propyl]isoquinoline (250 mg, 0.76 mmol) and stannous dihydrate (860 mg, 3.8 mmol) in EtOH (50 mL) was obtained 220 mg (97%) of N-[(3,4-diaminophenoxy)propyl]-1,2,3,4-tetrahydroisoquinoline as a yellow viscous oil. $^1$H NMR (CDCl$_3$): 2.00–2.08 (m, 2H), 2.686 (t, 2H, J=7), 2.761 (t, 2H, J=5.5), 2.916 (t, 2H, J=5.5), 3.063 (s, 2H), 3.496 (s, 2H), 3.650 (s, 2H), 3.995 (t, 2H, J=7), 6.267 (dd, 1H, J=8.5; 2.5), 6.340 (d, 1H, J=2.5), 6.670 (d, 1H, J=8.5), 7.01–7.12 (m, 4H).

c) A mixture of N-[(3,4-diaminophenoxy)propyl]-1,2,3,4-tetrahydroisoquinoline (200 mg, 0.67 mmol) and CDI (162 mg, 1.0 mmol) in toluene (15 mL) was refluxed for 16 h, then evaporated. The residual solid was washed with EtOAc (2×5 mL) and CHCl$_3$ (5 mL), then dried to give 107 mg (48%) of the title compound as a yellow powder. $^1$H NMR (DMSO-d$_6$): 1.90–1.96 (m, 2H), 2.591 (d, 2H, J=7), 2.662 (t, 2H, J=5), 2.803 (t, 2H, J=5), 3.560 (s, 2H), 3.967 (t, 2H, J=6), 6.50–6.52 (m, 2H), 6.76–6.80 (m, 1H), 7.05–7.10 (m, 4H), 10.359 (s, 1H), 10.483 (s, 1H). The hydrochloride, mp. 210–5° C. (dec). Analysis, Calcd. for (C$_{19}$H$_{22}$ClN$_3$O$_2$+0.3 HCl): C 61.55, H 6.06, N 11.33; Found: C 61.57, H 6.14, N 11.05.

EXAMPLE 109

N-(2-(2-oxobenzimidazol-5-oxy)ethyl)-1,2,3,4-tetrahydroisoquinoline

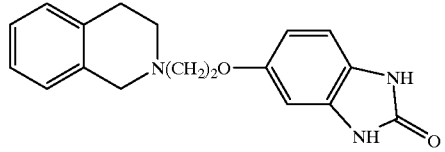

a) From a mixture of 1,2,3,4-tetrahydroisoquinoline (400 mg, 3.0 mmol), (4-amino-3-nitrophenoxy)ethyl bromide (390 mg, 1.5 mmol) and NaI (56 mg) in toluene (15 mL) was obtained 282 mg (60%) of N-[(4-amino-3-nitrophenoxy)ethyl]-1,2,3,4-tetrahydroisoquinoline as a yellow powder. $^1$H NMR (CDCl$_3$): 2.87–3.00 (m, 6H), 3.781 (s, 2H), 4.173 (t, 2H, J=6), 5.889 (bs, 2H), 6.762 (d, 1H, J=9), 7.02–7.04 (m, 1H), 7.11–7.14 (m, 4H), 7.602 (d, 1H, J=3).

b) A mixture of N-[(4-amino-3-nitrophenoxy)ethyl]-1,2,3,4-tetrahydroisoquinoline (250 mg, 0.8 mmol) and Raney Ni (about 200 mg) in MeOH (15 mL) was shaken under H$_2$ (25 parr) for 4 h, then filtered. The filtrate was evapoated, and the residue was purified by chromatography over silica gel (CHCl$_3$-EtOH-NH$_4$OH, 60:40:0.5) to give 218 mg (96%) of N-[(3,4-diaminophenoxy)ethyl]-1,2,3,4-tetrahydroisoquinoline as a brown viscous oil. $^1$H NMR (CDCl$_3$): 2.87–2.96 (m, 10H), 3.764 (s, 2H), 4.122 (t, 2H, J=5), 6.545 (dd, 1H, J=8; 2), 6.362 (d, 1H, J=2), 6.633 (d, 1H, J=8), 7.01–7.20 (m, 5H).

c) From a mixture of N-[(3,4-diaminophenoxy)ethyl]-1,2,3,4-tetrahydroisoquinoline (218 mg, 0.77 mmol) and CDI (190 mg, 1.17 mmol) in toluene (15 mL) was obtained 218 mg (70%) of the title compound as a white powder, mp 210–212° C. $^1$H NMR (DMSO-d$_6$): 2.76–2.85 (m, 6H), 3.654 (s, 2H), 4.087 (t, 2H, J=5.5), 6.51–6.54 (m, 2H), 6.780 (d, 1H, J=9), 7.02–7.09 (m, 4H), 10.360 (s, 1H), 10.496 (s, 1H). The hydrochloride, mp 234–6° C.

The Xenopus oocyte expression system. Mature female Xenopus laevis were anaesthetized (20–40 min) using 0.15% 3-aminobenzoic acid ethyl ester (MS-222) and 2–4 ovarian lobes were surgically removed. Oocytes at developmental stages IV-VI (Dumont, J. N., *J. Morphol.* 136:153–180 (1972)), were dissected from the ovary still surrounded by enveloping ovarian tissues. Follicle-enclosed oocytes were micro-injected with 1:1 mixtures of cRNA:NR1A+NR2A, 2B, 2C or 2D; injecting ~2, 5, or 20 ng of RNA encoding each receptor subunit. NR1A encoding cRNA was injected alone at ~20 ng. Oocytes were stored in Barth's medium containing (in mM): NaCl, 88; KCl, 1; CaCl$_2$, 0.41; Ca(NO$_3$)$_2$, 0.33; MgSO$_4$, 0.82; NaHCO$_3$, 2.4; HEPES 5; pH 7.4, with 0.1 mg/mL gentamycin sulphate. While oocytes were still surrounded by enveloping ovarian tissues the Barth's medium was supplemented with 0.1% bovine serum. Oocytes were defolliculated 1–2 days following injections by treatment with collagenase (0.5 mg/mL Sigma Type I for 0.5–1 hr) (Miledi and Woodward, *J. Physiol.* (Lond.) 416:601–621 (1989)) and subsequently stored in serum-free medium.

Electrical recordings were made using a conventional two-electrode voltage clamp (Dagan TEV-200) over periods ranging between 3–21 days following injection. Oocytes were placed in a 0.1 mL recording chamber continuously perfused (5–15 mL min$^{-1}$) with frog Ringer's solution containing (in mM): NaCl, 115; KCl, 2; CaCl$_2$, 1.8; HEPES, 5; pH 7.4. Drugs were applied by bath perfusion. When using the more rapid flow rates, half-times for mid-chamber solution changes were between 2–3 sec, however, exchange rates for drug solutions at the oocyte surface (i.e. beneath the vitelline envelope and among the tangles of microvilli) were probably considerably longer (Woodward et al., *Mol. Pharmacol.* 41:89–103 (1992)). Zero-Ca$^{2+}$/Ba$^{2+}$ Ringer had the composition (in mM): NaCl, 115; KCl, 2; BaCl$_2$, 1.8; HEPES, 5; pH 7.4. Intraoocyte injections were made by pneumatic pressure-pulse ejection from micropipettes (Miledi and Parker, *J. Physiol.* (Lond.) 357:173–183 (1984)). Injection solutions of EGTA (40–400 mM) and BAPTA (50–500 mM) were made up in H$_2$O, pH adjusted to 7.4 with KOH or HCl, and filtered to minimize plugging (Acrodisc-13, 0.2 $\mu$M). Pressure was set between 200–400 kPa. The volume of injections was regulated by adjusting the time of pulses (0.1–1 sec) and was estimated by measuring the diameters of ejected droplets.

Data Analysis. The logistic equation (equation 1) was fit to the data for individual concentration-response relations by adjusting the slope factor, n, and the parameter pEC$_{50}$; pEC$_{50}$=–log EC$_{50}$ where EC$_{50}$ is the agonist concentration that produces half the maximum response (De Lean et al., *Am. J. Physiol.* 235:E97-E102 (1978)) (Origin: Microcal Software).

$$I/I_{max}=1/(1+(10^{-PEC50}[\text{agonist}])^n) \quad \text{Eq. 1}$$

Concentration-inhibition curves were fit with equation 2.

$$I/I_{control}=1/(1+([\text{antagonist}]/10^{-pIC50})^n) \quad \text{Eq. 2}$$

in which I$_{control}$ is the current evoked by agonists alone, pIC$_{50}$=–log IC$_{50}$, TC$_{50}$ is the concentration of antagonist that produces half maximal inhibition, and n is the slope factor. For incomplete curves analysis by fitting was unreliable and IC$_{50}$ values were calculated by simple regression over linear portions of the curves (Origin: Microcal Software).

Drugs. The drugs were synthesized as described in the Examples above.

Drugs were initially dissolved at concentrations of 10–100 mM in DMSO. Dilutions were then made to generate a series of DMSO stock solutions over the range 10 $\mu$M to 100 mM. Working solutions were made by 1000–3000 fold dilution of stocks into Ringer. At these dilutions DMSO alone had no measurable effects on membrane current responses. DMSO stock solutions were stored for up to two weeks in the dark at 4° C. without apparent reductions in potency. Ringer solutions of drugs were made up fresh each day of use.

Maximal Electroshock-induced Seizures. Seizures were induced by application of current (50 mA, 60 pulses/sec, 0.8 sec pulse width, 1 sec duration, d.c.) through saline-coated corneal electrodes using a Ugo Basile ECT device (Model 7801). Mice were restrained by gripping the loose skin on their dorsal surface, electrodes were held lightly against the two cornea, then current was applied and mice were observed for a period of up to 30 sec for the occurrence of a tonic hindlimb extensor response. A tonic seizure was defined as a hindlimb extension in excess of 90 degrees from the plane of the body. Results were treated in a quantal manner.

Results

The results from the in vitro and in vivo assays are shown in Table 1.

TABLE 1

| Example # (Compound) | 1A/2A IC$_{50}$ $\mu$M | 1A/2B IC$_{50}$, $\mu$M | 1A/2C IC$_{50}$, $\mu$M | Mes. ED$_{50}$ mg/kg |
|---|---|---|---|---|
| Ex. 2 | >300 | 1.6 | >300 | |
| Ex. 3 | >300 | 4.0 | >300 | |
| Ex. 6 | >300 | 2.3 | >300 | |
| Ex. 7 | >300 | 65 | >300 | |
| Ex. 8 | >300 | 65 | >300 | |
| Ex. 9 | 240 | 14 | >300 | |
| Ex. 13 | 80.0 | 53.0 | 140 | |
| Ex. 15 | 60 | 5.5 | 230 | |
| Ex. 16 | 20.0 | 17.0 | 80.0 | |
| Ex. 18 | 140 | 35.0 | >100 | |
| Ex. 19 | 75 | 10 | 275 | |
| Ex. 25 | 60.0 | 9.0 | 175 | |
| Ex. 26 | 30 | 15 | 105 | |
| Ex. 27 | >300 | 50 | >300 | |
| Ex. 30 | 95 | 8.0 | >100 | |
| Ex. 34 | >300 | 240 | >300 | |
| Ex. 35 | >300 | 150 | >300 | |
| Ex. 38(A) | 25 | 72 | 65 | |
| Ex. 38(B) | 28 | 50 | 50 | |
| Ex. 41 | >300 | >300 | >300 | |
| Ex. 47 | 270 | 40 | >300 | |
| Ex. 82 | 290 | 3.3 | >300 | |
| Ex. 83 | 224 | 1.8 | >300 | 3.5 |
| Ex. 84 | 270 | 6 | >300 | |
| Ex. 85 | >300 | 6 | >300 | |
| Ex. 86 | >300 | 12 | >300 | |
| Ex. 87 | >300 | 7 | >300 | |
| Ex. 88 | >300 | 5 | >300 | |
| Ex. 89 | 150 | 0.3 | >100 | 5.0 |
| Ex. 90 | >300 | 1.3 | >300 | |
| Ex. 91 | 230 | 2.5 | >300 | 6.0 |
| Ex. 92 | >300 | 8 | >300 | |
| Ex. 93 | >300 | 9 | >300 | 8.0 |
| Ex. 99 | >300 | 1.6 | >300 | 6.0 |
| Ex. 100 | >300 | 3.0 | >300 | 3.5 |
| Ex. 101 | 260 | 280 | 300 | |
| Ex. 102 | >300 | 3.5 | >300 | |
| Ex. 103 | 3.5 | 0.2 | 58 | |
| Ex. 104 | 110 | 0.8 | >300 | 2.0 |
| Ex. 105 | 120 | 17 | >300 | |
| Ex. 106 | 8.5 | 5.0 | 23 | |
| Ex. 107 | 250 | 160 | 75 | |
| Ex. 108 | 24 | 7.5 | >300 | |
| Ex. 109 | 190 | 140 | >300 | |
| (A) | >300 | 5.0 | >300 | |
| (B) | >300 | 25.0 | >300 | |
| (C) | >300 | 10.0 | >300 | |

Notes:
Cmp. A is 4-benzyl-1-hexylpiperidine
Cmp. B is 4-benzyl-1-butylpiperidine
Cmp. C is 4-(3'-fluorobenzoyl)-1-(4"-phenylbutyl)piperidine

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A compound having the Formula (I):

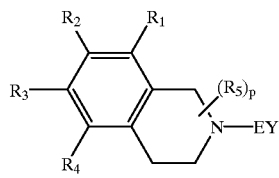

or a pharmaceutically acceptable salt thereof; wherein
$R_1$–$R_4$ are independently hydrogen, halo, haloalkyl, aryl, fused aryl, a heterocyclic group, a heteroaryl group, alkyl, alkenyl, alkynyl, arylalkyl, arylalkenyl, arylalkynyl, hydroxyalkyl, nitro, amino, cyano, cyanamido, $N(CN)_2$, guanidino, amidino, acylamido, hydroxy, thiol, acyloxy, azido, alkoxy, carboxy, carbonylamido, or alkylthiol;

E is $(CR_aR_b)_r$—$G_s$—, wherein $R_a$ and $R_b$ are independently selected from the group consisting of hydrogen, alkyl, aryl, hydroxy or carboxy; G is oxygen, sulfur, sulfone, or sulfoxide; r is independently 1, 2, 3, 4, or 5; and s is 1;

$R_5$ is hydrogen, hydroxy, alkylcarboxy, optionally substituted aryl, optionally substituted aralkyl, optionally substituted aryloxyalkyl, optionally substituted benzyloxyalkyl, a heterocyclic group, a heterocyclic substituted alkyl group, heteroaryl, or a heteroaryl substituted alkyl group;

p is 0, 1, 2 or 3;

Y is an optionally substituted heterocyclic group, or an optionally substituted heteroaryl group; and providing that Y is not a dibenz-[b,e]oxepine, a quinolinone, a benzimidazol, a 1,2,4-triazole-[4,3-a]-pyridine, a pyran, or a phthalimide, or a substituted benzopyran, piperidine, pyridine, indole, quinolizine, benzofuran, oxadiazol or triazine.

2. A quaternary ammonium salt of a compound of claim 1.

3. A pharmaceutical composition comprising a compound of claim 1 and a pharmaceutically acceptable carrier.

4. A pharmaceutical composition comprising the compound of claim 2 and a pharmaceutically acceptable carrier.

5. A method of treating or preventing neuronal loss associated with stroke, ischemia, CNS trauma, hypoglycemia or surgery, or treating a neurodegenerative disease, or treating or preventing the adverse consequences of the overstimulation of the excitatory amino acids, or treating anxiety, psychosis, glaucoma, CMV retinitis, urinary incontinence, migraine headache, convulsions, aminoglycoside antibiotics-induced hearing loss, Parkinson's disease, chronic pain or inducing anesthesia, opioid tolerance or withdrawal, or enhancing cognition, comprising administering to an animal in need of such treatment an effective amount of a compound of claim 1.

6. A method of treating or preventing neuronal loss associated with stroke, ischemia, CNS trauma, hypoglycemia or surgery, or treating a neurodegenerative disease, or treating or preventing the adverse consequences of the overstimulation of the excitatory amino acids, or treating anxiety, psychosis, glaucoma, CMV retinitis, urinary incontinence, migraine headache, convulsions, aminoglycoside antibiotics-induced hearing loss, Parkinson's disease, chronic pain or inducing anesthesia, opioid tolerance or withdrawal, or enhancing cognition, comprising administering to an animal in need of such treatment an effective amount of a compound of claim 2.

7. The method of claim 5, wherein said compound is administered as part of a pharmaceutical composition comprising a pharmaceutically acceptable carrier.

8. The method of claim 6, wherein said compound is administered as part of a pharmaceutical composition comprising a pharmaceutically acceptable carrier.

* * * * *

UNITED STATES PATENT AND TRADEMARK OFFICE
CERTIFICATE OF CORRECTION

PATENT NO. : 6,534,522 B2
DATED : March 18, 2003
INVENTOR(S) : Christopher F. Bigge et al.

It is certified that error appears in the above-identified patent and that said Letters Patent is hereby corrected as shown below:

<u>Title page,</u>
Item [56], References Cited, FOREIGN PATENT DOCUMENTS,
"04217945" should read -- 4-217945 --;
OTHER PUBLICATIONS, "Annu. Rev. Neurosci" should read -- Annu. Rev. Neurosci. --;
"Chemical Abstract," should read -- Chemical Abstracts, --;
"Rojas et al." should read -- Rojas et al., --;
"after A.A.P.J. Leaó,; ""(1994)." should read -- (1944). --;
"S.R. Skilling et al," should read -- S.R. Skilling et al., --;
"Curtis), et al., should read -- Curtis et al., -- and
"Moriyoshi, et al." should read -- Moriyoshi, et al., --.
Item [75], Inventors, "Foothill, CA" should read -- Irvine, CA --

<u>Column 1,</u>
Line 29, "Aspartate" should read -- aspartate --; and
Line 63, "with" should read -- which --.

<u>Column 4,</u>
Line 14, "or 4." should read -- or 4, --.

<u>Column 5,</u>
Line 36, "$(CH_2)_M$" should read -- $(CH_2)_m$, --.

<u>Column 10,</u>
Line 15, "subtype selective" should read -- subtype-selective --.

<u>Column 11,</u>
Line 4, " 2-butnyyl" should read -- 2-butynyl --.

<u>Column 12,</u>
Line 36, "Formulae" should read -- formulae --; and
Line 47, "a" should read -- α, --.

<u>Column 13,</u>
Line 3, "g-bromo" should read -- β-bromo --.

UNITED STATES PATENT AND TRADEMARK OFFICE
CERTIFICATE OF CORRECTION

PATENT NO. : 6,534,522 B2
DATED : March 18, 2003
INVENTOR(S) : Christopher F. Bigge et al.

It is certified that error appears in the above-identified patent and that said Letters Patent is hereby corrected as shown below:

Column 26,
Ex. 21,

Ex. 21, " 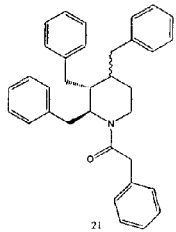 should read -- 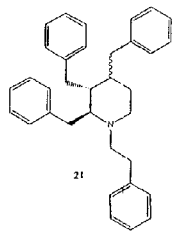 --

Column 28,
Line 61, "transformation" should read -- transformations --.

Column 29,
Line 13, "where in" should read -- wherein --.

Column 38,
Line 64, "group" should read -- group; --.

Column 44,
Line 37, "Ned." should read -- Med. --.

Column 46,
Lines 7 thru 10,

' 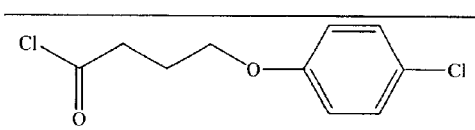 "

should read

-- 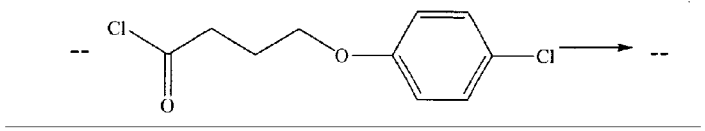 --

UNITED STATES PATENT AND TRADEMARK OFFICE
CERTIFICATE OF CORRECTION

PATENT NO. : 6,534,522 B2
DATED : March 18, 2003
INVENTOR(S) : Christopher F. Bigge et al.

It is certified that error appears in the above-identified patent and that said Letters Patent is hereby corrected as shown below:

Column 50,
Line 46, "are" should read -- are: --.

Column 51,
Line 23, "or 3" should read -- or 3; --.

Column 53,
Line 41, "Leao," should read -- Leaó, --; and
Line 53, "Subtype selective" should read -- Subtype-selective --.

Column 54,
Line 4, "rat" should read -- rats --.

Column 55,
Line 19, "(1995).)" should read -- (1995)). --; and
Line 54, "C02." should read -- $CO_2$. --.

Column 56,
Line 32, "NMDA induced" should read -- NMDA-induced --.

Column 62,
Line 33, "include," should read -- including, --.

Column 64,
Line 18, "mixutre" should read -- mixture --.

Column 68,
Line 23, "tetyrahydro-" should read -- tetrahydro- --.

Column 69,
Line 12, "P-" should read -- β- --;
Line 59, "-1.5 $H_2O$:" should read -- 1.5 $H_2O$: --; and
Line 64, "benzylpiperidine" should read -- benzylpiperidine. --.

Column 72,
Line 13, "(8, 3H);" should read -- (s, 3H); --; and
Line 14, "(d, J=7.2, 11);" should read -- (d, J= 7.2, 1 H); --.

UNITED STATES PATENT AND TRADEMARK OFFICE
CERTIFICATE OF CORRECTION

PATENT NO. : 6,534,522 B2
DATED : March 18, 2003
INVENTOR(S) : Christopher F. Bigge et al.

It is certified that error appears in the above-identified patent and that said Letters Patent is hereby corrected as shown below:

Column 74,
Line 56, "D$_2$O):" should read -- (D$_2$O): --.

Column 75,
Line 12, "J 7.2Hz," should read -- J= 7.2 Hz --; and
Line 29, "J 11.4," should read -- J= 11.4, --.

Column 76,
Line 34, "1H NMR", should read -- $^1$H NMR --.

Column 77,
Line 28, "(m, 10H). The" should read -- )m$_1$ 10H). ¶ The--; and
Line 46, "Hbr" should read -- The Hbr --.

Column 78,
Line 67, "tertbutoxycarbonyl" should read -- tertbutoxycarbonyl- --.

Column 79,
Line 27, "J-7.2Hz," should read -- J=7.2Hz, --; and
Line 60, "as as" should read -- as --.

Column 80,
Line 19, "1H NMR" should read -- $^1$H NMR --.

Column 81,
Line 49, "J 12.3Hz," should read -- J=12.3Hz, --; and
Line 65, "2H)" should read -- 2H). --.

Column 83,
Line 42, "(m, SH)," should read -- (m, 5H), --.

Column 84,
Line 6, "80%-0):" should read -- 80%): --;
Line 6, "-d6)" should read -- -d$_6$) --; and
Line 16, "53%)" should read -- 53%): --.

UNITED STATES PATENT AND TRADEMARK OFFICE
CERTIFICATE OF CORRECTION

PATENT NO. : 6,534,522 B2
DATED : March 18, 2003
INVENTOR(S) : Christopher F. Bigge et al.

It is certified that error appears in the above-identified patent and that said Letters Patent is hereby corrected as shown below:

Column 85,
Line 40, "added" should read -- added in a --.

Column 87,
Line 10, "NH4C1" should read -- $NH_4Cl$ --;
Line 38, "(5w," should read -- (5%, --; and
Line 39, "Vacuo" should read -- vacuo --.

Column 88,
Line 7, "2H;" should read -- 2H); --.

Column 90,
Line 38, "98%) 1H NMR" should read -- 98%): $^1$H NMR --;
Line 40, "-H)," should read -- 1H), --;
Line 53, "JH)," should read -- 1H), --;
Line 54, "SH)," should read -- 5H), --; and
Line 67, "3-one" should read -- 3-one. --.

Column 92,
Line 54, "g)" should read -- g): --.

Column 93,
Line 48, "64%)" should read -- 64%): --.

Column 100,
Line 19, "nitrosopiporidine A" should read -- nitrosopiperidine ¶ A --;
Line 34, "2H)" should read -- 2H). --; and
Line 37, "refux" should read -- reflux --.

Column 103,
Line 48, "$I/I_{max} = 1/(1+(10^{-PEC50}[agoinst])")$" should read -- $I/I_{max} = 1/(1+(10^{-pEC50}/[agonist])")$ --; and
Line 54, "$TC_{50}$" should read -- $IC_{50}$ --.

UNITED STATES PATENT AND TRADEMARK OFFICE
CERTIFICATE OF CORRECTION

PATENT NO. : 6,534,522 B2
DATED : March 18, 2003
INVENTOR(S) : Christopher F. Bigge et al.

It is certified that error appears in the above-identified patent and that said Letters Patent is hereby corrected as shown below:

Column 104,
Table I, "1A/2A" 1A/2A
$IC_{50}$ μM should read -- $IC_{50}$, μ M --.

Column 105,
Line 37, "group," should read -- group --.

Signed and Sealed this

Ninth Day of March, 2004

JON W. DUDAS
*Acting Director of the United States Patent and Trademark Office*